United States Patent
Davis et al.

(10) Patent No.: US 6,479,267 B1
(45) Date of Patent: Nov. 12, 2002

(54) FY7 POLYMERASE

(75) Inventors: Maria Cuozzo Davis, Princeton, NJ (US); Carl W. Fuller, Berkeley Heights, NJ (US); Lin Huang, Bridgewater, NJ (US); Joseph Anthony Mamone, Greenbrook, NJ (US)

(73) Assignee: Amersham Pharmacia Biotech, Inc., Piscataway, NJ (US)

( * ) Notice: Subject to any disclaimer, the term of this patent is extended or adjusted under 35 U.S.C. 154(b) by 0 days.

(21) Appl. No.: 09/334,818

(22) Filed: Jun. 17, 1999

Related U.S. Application Data

(60) Provisional application No. 60/089,556, filed on Jun. 17, 1998.

(51) Int. Cl.[7] .............................. C12N 9/12; C12N 9/00
(52) U.S. Cl. ..................... 435/194; 435/183; 435/193; 435/6; 435/91.2; 530/350; 530/358
(58) Field of Search .................... 435/6, 91.2, 91.1, 435/183, 193, 194; 530/358, 350

(56) References Cited

U.S. PATENT DOCUMENTS

| | | | |
|---|---|---|---|
| 5,192,674 A | * 3/1993 | Oshima et al. | 435/194 |
| 5,593,840 A | 1/1997 | Bhatnagar et al. | 435/6 |
| 5,610,066 A | 3/1997 | Fuller et al. | 435/320.1 |
| 5,618,711 A | 4/1997 | Gelfand et al. | 435/194 |
| 5,633,138 A | 5/1997 | Davis et al. | 435/6 |
| 5,744,312 A | 4/1998 | Mamone et al. | 435/6 |
| 5,789,224 A | 8/1998 | Gelfand et al. | 435/194 |
| 5,795,762 A | 8/1998 | Abramson et al. | 435/194 |
| 5,804,375 A | 9/1998 | Gelfand et al. | 435/6 |
| 5,885,813 A | 3/1999 | Davis et al. | 435/182 |
| 5,948,614 A | * 9/1999 | Chatterjee | 435/6 |

FOREIGN PATENT DOCUMENTS

| | | |
|---|---|---|
| EP | 0 745 676 A1 | 12/1996 |
| WO | WO 91/09950 | 7/1991 |
| WO | WO 98/01562 | 1/1998 |

OTHER PUBLICATIONS

Takagi et al. Characterization of DNA Polymerase from Pyrococcus sp. Strain KOD1 and its Application to PCR, Applied and Enviromental Microbiology 63(11): 4504–4510, Nov. 1997.*

Gutman, Pablo and Minton, Kenneth; Conserved Sites in the 5'–3' Exonuclease Domain of *Escherichia coli* DNA Polymerase; Nucleic Acids Research, 1993, vol. 21, No. 18, pp. 4406–4407.

Reeve, Michael and Fuller, Carl; A Novel Thermostable Polymerase for DNA Sequencing; Nature, vol. 376, Aug. 31, 1995, pp. 796–797.

* cited by examiner

*Primary Examiner*—Rebecca E. Prouty
*Assistant Examiner*—Richard Hutson
(74) *Attorney, Agent, or Firm*—Royal N. Ronning, Jr.; Stephen G. Ryan

(57) ABSTRACT

A purified recombinant thermostable DNA polymerase polymerase which exhibits at least about 80% activity at salt concentrations of 50 mM and greater, at least about 70% activity at salt concentrations of 25 mM and greater, and having a processivity of about 30 nucleotides per binding event. An isolated nucleic acid that encodes the thermostable DNA polymerase, as well as a recombinant DNA vector comprising the nucleic acid and a recombinant host cell transformed with the vector, are also disclosed. A method of sequencing DNA using the DNA polymerase as well as a kit for sequencing DNA is also disclosed.

2 Claims, 51 Drawing Sheets

```
/1                                       31/11
ATG GAA GCG ATG CTG CCG CTG TTC GAA CCC AAA GGC CGT GTC CTC CTG GTG GCC GGC CAC
 M   E   A   M   L   P   L   F   E   P   K   G   R   V   L   L   V   A   G   H
61/21                                    91/31
CAC CTG GCC TAC CGC ACC TTC TTC GCC CTG AAG GGC CTC ACC ACG AGC CGG GGC GAA CCG
 H   L   A   Y   R   T   F   F   A   L   K   G   L   T   T   S   R   G   E   P
121/41                                   151/51
GTG CAG GCG GTC TAC GGC TTC GCC AAG AGC CTC CTC AAG GCC CTG AAG GAG GAC GGG TAC
 V   Q   A   V   Y   G   F   A   K   S   L   L   K   A   L   K   E   D   G   Y
181/61                                   211/71
AAG GCC GTC TTC GTG GTC TTT GAC GCC AAG GCC CCC TCC TTC CGC CAC GAG GCC TAC GAG
 K   A   V   F   V   V   F   D   A   K   A   P   S   F   R   H   E   A   Y   E
241/81                                   271/91
GCC TAC AAG GCG GGG AGG GCC CCG ACC CCC GAG GAC TTC CCC CGG CAG CTC GCC CTC ATC
 A   Y   K   A   G   R   A   P   T   P   E   D   F   P   R   Q   L   A   L   I
301/101                                  331/111
AAG GAG CTG GTG GAC CTC CTG GGG TTT ACC CGC CTC GAG GTC CCC GGC TAC GAG GCG GAC
 K   E   L   V   D   L   L   G   F   T   R   L   E   V   P   G   Y   E   A   D
361/121                                  391/131
GAC GTT CTC GCC ACC CTG GCC AAG AAG GCG GAA AAG GAG GGG TAC GAG GTG CGC ATC CTC
 D   V   L   A   T   L   A   K   K   A   E   K   E   G   Y   E   V   R   I   L
421/141                                  451/151
ACC GCC GAC CGC GAC CTC TAC CAA CTC GTC TCC GAC CGC GTC GCC GTC CTC CAC CCC GAG
 T   A   D   R   D   L   Y   Q   L   V   S   D   R   V   A   V   L   H   P   E
481/161                                  511/171
GGC CAC CTC ATC ACC CCG GAG TGG CTT TGG GAG AAG TAC GGC CTC AGG CCG GAG CAG TGG
 G   H   L   I   T   P   E   W   L   W   E   K   Y   G   L   R   P   E   Q   W
541/181                                  571/191
GTG GAC TTC CGC GCC CTC GTG GGG GAC CCC TCC GAC AAC CTC CCC GGG GTC AAG GGC ATC
 V   D   F   R   A   L   V   G   D   P   S   D   N   L   P   G   V   K   G   I
601/201                                  631/211
GGG GAG AAG ACC GCC CTC AAG CTC CTC AAG GAG TGG GGA AGC CTG GAA AAC CTC CTC AAG
 G   E   K   T   A   L   K   L   L   K   E   W   G   S   L   E   N   L   L   K
661/221                                  691/231
AAC CTG GAC CGG GTA AAG CCA GAA AAC GTC CGG GAG AAG ATC AAG GCC CAC CTG GAA GAC
 N   L   D   R   V   K   P   E   N   V   R   E   K   I   K   A   H   L   E   D
721/241                                  751/251
CTC AGG CTC TCC TTG GAG CTC TCC CGG GTG CGC ACC GAC CTC CCC CTG GAG GTG GAC CTC
 L   R   L   S   L   E   L   S   R   V   R   T   D   L   P   L   E   V   D   L
781/261                                  811/271
GCC CAG GGG CGG GAG CCC GAC CGG GAG GGG CTT AGG GCC TTC CTG GAG AGG CTG GAA TTC
 A   Q   G   R   E   P   D   R   E   G   L   R   A   F   L   E   R   L   E   F
841/281                                  871/291
GGC AGC CTC CTC CAC GAG TTC GGC CTC CTG GAG GCC CCC GCC CCC CTG GAG GAG GCC CCC
 G   S   L   L   H   E   F   G   L   L   E   A   P   A   P   L   E   E   A   P
901/301                                  931/311
TGG CCC CCG CCG GAA GGG GCC TTC GTG GGC TTC GTC CTC TCC CGC CCC GAG CCC ATG TGG
 W   P   P   P   E   G   A   F   V   G   F   V   L   S   R   P   E   P   M   W
961/321                                  991/331
GCG GAG CTT AAA GCC CTG GCC GCC TGC AGG GAC GGC CGG GTG CAC CGG GCA GCA GAC CCC
 A   E   L   K   A   L   A   A   C   R   D   G   R   V   H   R   A   A   D   P
1021/341                                 1051/351
TTG GCG GGG CTA AAG GAC CTC AAG GAG GTC CGG GGC CTC CTC GCC AAG GAC CTC GCC GTC
 L   A   G   L   K   D   L   K   E   V   R   G   L   L   A   K   D   L   A   V
```

FIG.1A

```
1081/361                                          1111/371
TTG GCC TCG AGG GAG GGG CTA GAC CTC GTG  CCC GGG GAC GAC CCC ATG CTC CTC GCC TAC
 L   A   S   R   E   G   L   D   L   V    P   G   D   D   P   M   L   L   A   Y
1141/381                                          1171/391
CTC CTG GAC CCC TCC AAC ACC ACC CCC GAG  GGG GTG GCG CGG CGC TAC GGG GGG GAG TGG
 L   L   D   P   S   N   T   T   P   E    G   V   A   R   R   Y   G   G   E   W
1201/401                                          1231/411
ACG GAG GAC GCC GCC CAC CGG GCC CTC CTC  TCG GAG AGG CTC CAT CGG AAC CTC CTT AAG
 T   E   D   A   A   H   R   A   L   L    S   E   R   L   H   R   N   L   L   K
1261/421                                          1291/431
CGC CTC GAG GGG GAG GAG AAG CTC CTT TGG  CTC TAC CAC GAG GTG GAA AAG CCC CTC TCC
 R   L   E   G   E   E   K   L   L   W    L   Y   H   E   V   E   K   P   L   S
1321/441                                          1351/451
CGG GTC CTG GCC CAC ATG GAG GCC ACC GGG  GTA CGG CTG GAC GTG GCC TAC CTT CAG GCC
 R   V   L   A   H   M   E   A   T   G    V   R   L   D   V   A   Y   L   Q   A
1381/461                                          1411/471
CTT TCC CTG GAG CTT GCG GAG GAG ATC CGC  CGC CTC GAG GAG GAG GTC TTC CGC TTG GCG
 L   S   L   E   L   A   E   E   I   R    R   L   E   E   E   V   F   R   L   A
1441/481                                          1471/491
GGC CAC CCC TTC AAC CTC AAC TCC CGG GAC  CAG CTG GAA AGG GTG CTC TTT GAC GAG CTT
 G   H   P   F   N   L   N   S   R   D    Q   L   E   R   V   L   F   D   E   L
1501/501                                          1531/511
AGG CTT CCC GCC TTG GGG AAG ACG CAA AAG  ACA GGC AAG CGC TCC ACC AGC GCC GCG GTG
 R   L   P   A   L   G   K   T   Q   K    T   G   K   R   S   T   S   A   A   V
1561/521                                          1591/531
CTG GAG GCC CTA CGG GAG GCC CAC CCC ATC  GTG GAG AAG ATC CTC CAG CAC CGG GAG CTC
 L   E   A   L   R   E   A   H   P   I    V   E   K   I   L   Q   H   R   E   L
1621/541                                          1651/551
ACC AAG CTC AAG AAC ACC TAC GTG GAC CCC  CTC CCA AGC CTC GTC CAC CCG AGG ACG GGC
 T   K   L   K   N   T   Y   V   D   P    L   P   S   L   V   H   P   R   T   G
1681/561                                          1711/571
CGC CTC CAC ACC CGC TTC AAC CAG ACG GCC  ACG GCC ACG GGG AGG CTT AGT AGC TCC GAC
 R   L   H   T   R   F   N   Q   T   A    T   A   T   G   R   L   S   S   S   D
1741/581                                          1771/591
CCC AAC CTG CAG AAC ATC CCC GTC CGC ACC  CCC TTG GGC CAG AGG ATC CGC CGG GCC TTC
 P   N   L   Q   N   I   P   V   R   T    P   L   G   Q   R   I   R   R   A   F
1801/601                                          1831/611
GTG GCC GAG GCG GGT TGG GCG TTG GTG GCC  CTG GAC TAT AGC CAG ATA GAG CTC CGC GTC
 V   A   E   A   G   W   A   L   V   A    L   D   Y   S   Q   I   E   L   R   V
1861/621                                          1891/631
CTC GCC CAC CTC TCC GGG GAC GAA AAC CTG  ATC AGG GTC TTC CAG GAG GGG AAG GAC ATC
 L   A   H   L   S   G   D   E   N   L    I   R   V   F   Q   E   G   K   D   I
1921/641                                          1951/651
CAC ACC CAG ACC GCA AGC TGG ATG TTC GGC  GTC CCC CCG GAG GCC GTG GAC CCC CTG ATG
 H   T   Q   T   A   S   W   M   F   G    V   P   P   E   A   V   D   P   L   M
1981/661                                          2011/671
CGC CGG GCG GCC AAG ACG GTG AAC TAC GGC  GTC CTC TAC GGC ATG TCC GCC CAT AGG CTC
 R   R   A   A   K   T   V   N   Y   G    V   L   Y   G   M   S   A   H   R   L
2041/681                                          2071/691
TCC CAG GAG CTA GCC ATC CCC TAC GAA GAA  GCG GTG GCC TTT ATA GAG CGC TAC TTC CAA
 S   Q   E   L   A   I   P   Y   E   E    A   V   A   F   I   E   R   Y   F   Q
2101/701                                          2131/711
AGC TTC CCC AAG GTG CGG GCC TGG ATA GAA  AAG ACC CTG GAG GAG GGG AGG AAG CGG GGC
 S   F   P   K   V   R   A   W   I   E    K   T   L   E   E   G   R   K   R   G
```

FIG.1B

```
2161/721                                    2191/731
TAC GTG AAA ACC CTC TTC GGA AGA AGG CGC TAC GTG CCC GAC CTC AAC GCC CGG GTG AAG
 Y   V   E   T   L   F   G   R   R   R   Y   V   P   D   L   N   A   R   V   K

2221/741                                    2251/751
AGC GTC AGG GAG GCC GCG GAG CGC ATG GCC TTC AAC ATG CCC GTC CAG GGC ACC GCC GCC
 S   V   R   E   A   A   E   R   M   A   F   N   M   P   V   Q   G   T   A   A

2281/761                                    2311/771
GAC CTC ATG AAG CTC GCC ATG GTG AAG CTC TTC CCC CGC CTC CGG GAG ATG GGG GCC CGC
 D   L   M   K   L   A   M   V   K   L   F   P   R   L   R   E   M   G   A   R

2341/781                                    2371/791
ATG CTC CTC CAG GTC CAC GAC GAG CTC CTC CTG GAG GCC CCC CAA GCG CGG GCC GAG GAG
 M   L   L   Q   V   H   D   E   L   L   L   E   A   P   Q   A   R   A   E   E

2401/801                                    2431/811
GTG GCG GCT TTG GCC AAG GAG GCS ATG GAG AAG GCC TAT CCC CTC GCC GTG CCC CTG GAG
 V   A   A   L   A   K   E   A   M   E   K   A   Y   P   L   A   V   P   L   E

2461/821                                    2491/831
GTG GAG GTG GGG ATG GGG GAG GAC TGG CTT TCC GCC AAG GGT TAG
 V   E   V   G   M   G   E   D   W   L   S   A   K   G   *
```

FIG.1C

| POLYMERASE | PROCESSIVITY NUMBER OF NUCLEOTIDES |
|---|---|
| THERMO SEQUENASE | 4 |
| AMPLITAQ FS | 15 |
| FY7 | 30 |

FIG.16

SEQUENCE LISTING

<160> NUMBER OF SEQ ID NOS: 27

<210> SEQ ID NO 1
<211> LENGTH: 2505
<212> TYPE: DNA
<213> ORGANISM: Thermus thermophilus
<220> FEATURE:
<221> NAME/KEY: CDS
<222> LOCATION: (1)..(2502)

<400> SEQUENCE: 1

```
atg gaa gcg atg ctg ccg ctg ttc gaa ccc aaa ggc cgt gtc ctc ctg        48
Met Glu Ala Met Leu Pro Leu Phe Glu Pro Lys Gly Arg Val Leu Leu
 1               5                  10                  15 gtg gcc ggc cac cac ctg gcc tac cgc acc ttc ttc gcc ctg aag ggc        96
Val Ala Gly His His Leu Ala Tyr Arg Thr Phe Phe Ala Leu Lys Gly
             20                  25                  30 ctc acc acg agc cgg ggc gaa ccg gtg cag gcg gtc tac ggc ttc gcc       144
Leu Thr Thr Ser Arg Gly Glu Pro Val Gln Ala Val Tyr Gly Phe Ala
         35                  40                  45 aag agc ctc ctc aag gcc ctg aag gag gac ggg tac aag gcc gtc ttc       192
Lys Ser Leu Leu Lys Ala Leu Lys Glu Asp Gly Tyr Lys Ala Val Phe
     50                  55                  60 gtg gtc ttt gac gcc aag gcc ccc tcc ttc cgc cac gag gcc tac gag       240
Val Val Phe Asp Ala Lys Ala Pro Ser Phe Arg His Glu Ala Tyr Glu
 65                  70                  75                  80 gcc tac aag gcg ggg agg gcc ccg acc ccc gag gac ttc ccc cgg cag       288
Ala Tyr Lys Ala Gly Arg Ala Pro Thr Pro Glu Asp Phe Pro Arg Gln
                 85                  90                  95 ctc gcc ctc atc aag gag ctg gtg gac ctc ctg ggg ttt acc cgc ctc       336
Leu Ala Leu Ile Lys Glu Leu Val Asp Leu Leu Gly Phe Thr Arg Leu
            100                 105                 110
```

-continued

```
gag gtc ccc ggc tac gag gcg gac gac gtt ctc gcc acc ctg gcc aag    384
Glu Val Pro Gly Tyr Glu Ala Asp Asp Val Leu Ala Thr Leu Ala Lys
        115                 120                 125 aag gcg gaa aag gag ggg tac gag gtg cgc atc ctc acc gcc gac cgc    432
Lys Ala Glu Lys Glu Gly Tyr Glu Val Arg Ile Leu Thr Ala Asp Arg
130                 135                 140 gac ctc tac caa ctc gtc tcc gac cgc gtc gcc gtc ctc cac ccc gag    480
Asp Leu Tyr Gln Leu Val Ser Asp Arg Val Ala Val Leu His Pro Glu
145                 150                 155                 160 acc gcc gac cgc gac ctc tac caa ctc gtc tcc gac cgc gtc gcc gtc    528
Thr Ala Asp Arg Asp Leu Tyr Gln Leu Val Ser Asp Arg Val Ala Val
            165                 170                 175 ctc cac ccc gag ggc cac ctc atc acc ccg gag tgg ctt tgg gag aag    576
Leu His Pro Glu Gly His Leu Ile Thr Pro Glu Trp Leu Trp Glu Lys
        180                 185                 190 tac ggc ctc agg ccg gag cag tgg gtg gac ttc cgc gcc ctc gtg ggg    624
Tyr Gly Leu Arg Pro Glu Gln Trp Val Asp Phe Arg Ala Leu Val Gly
        195                 200                 205 gac ccc tcc gac aac ctc ccc ggg gtc aag ggc atc ggg gag aag acc    672
Asp Pro Ser Asp Asn Leu Pro Gly Val Lys Gly Ile Gly Glu Lys Thr
210                 215                 220 gcc ctc aag ctc ctc aag gag tgg gga agc ctg gaa aac ctc ctc aag    720
Ala Leu Lys Leu Leu Lys Glu Trp Gly Ser Leu Glu Asn Leu Leu Lys
225                 230                 235                 240 ctc agg ctc tcc ttg gag ctc tcc cgg gtg cgc acc gac ctc ccc ctg    768
Leu Arg Leu Ser Leu Glu Leu Ser Arg Val Arg Thr Asp Leu Pro Leu
            245                 250                 255 gag gtg gac ctc gcc cag ggg cgg gag ccc gac cgg gag ggg ctt agg    816
Glu Val Asp Leu Ala Gln Gly Arg Glu Pro Asp Arg Glu Gly Leu Arg
        260                 265                 270 gcc ttc ctg gag agg ctg gaa ttc ggc agc ctc ctc cac gag ttc ggc    864
Ala Phe Leu Glu Arg Leu Glu Phe Gly Ser Leu Leu His Glu Phe Gly
275                 280                 285 ctc ctg gag gcc ccc gcc ccc ctg gag gag gcc ccc tgg ccc ccg ccg    912
Leu Leu Glu Ala Pro Ala Pro Leu Glu Glu Ala Pro Trp Pro Pro Pro
        290                 295                 300 gaa ggg gcc ttc gtg ggc ttc gtc ctc tcc cgc ccc gag ccc atg tgg    960
Glu Gly Ala Phe Val Gly Phe Val Leu Ser Arg Pro Glu Pro Met Trp
305                 310                 315                 320 gcg gag ctt aaa gcc ctg gcc gcc tgc agg gac ggc cgg gtg cac cgg   1008
Ala Glu Leu Lys Ala Leu Ala Ala Cys Arg Asp Gly Arg Val His Arg
            325                 330                 335 gca gca gac ccc ttg gcg ggg cta aag gac ctc aag gag gtc cgg ggc   1056
Ala Ala Asp Pro Leu Ala Gly Leu Lys Asp Leu Lys Glu Val Arg Gly
        340                 345                 350 ctc ctc gcc aag gac ctc gcc gtc ttg gcc tcg agg gag ggg cta gac   1104
Leu Leu Ala Lys Asp Leu Ala Val Leu Ala Ser Arg Glu Gly Leu Asp
            355                 360                 365 ctc gtg ccc ggg gac gac ccc atg ctc ctc gcc tac ctc ctg gac ccc   1152
Leu Val Pro Gly Asp Asp Pro Met Leu Leu Ala Tyr Leu Leu Asp Pro
370                 375                 380 tcc aac acc acc ccc gag ggg gtg gcg cgg cgc tac ggg ggg gag tgg   1200
Ser Asn Thr Thr Pro Glu Gly Val Ala Arg Arg Tyr Gly Gly Glu Trp
385                 390                 395                 400 acg gag gac gcc gcc cac cgg gcc ctc ctc tcg gag agg ctc cat cgg   1248
Thr Glu Asp Ala Ala His Arg Ala Leu Leu Ser Glu Arg Leu His Arg
            405                 410                 415 aac ctc ctt aag cgc ctc gag ggg gag gag aag ctc ctt tgg ctc tac   1296
Asn Leu Leu Lys Arg Leu Glu Gly Glu Glu Lys Leu Leu Trp Leu Tyr
        420                 425                 430
```

```
cac gag gtg gaa aag ccc ctc tcc cgg gtc ctg gcc cac atg gag gcc    1344
His Glu Val Glu Lys Pro Leu Ser Arg Val Leu Ala His Met Glu Ala
            435                 440                 445 acc ggg gta cgg ctg gac gtg gcc tac ctt cag gcc ctt tcc ctg gag    1392
Thr Gly Val Arg Leu Asp Val Ala Tyr Leu Gln Ala Leu Ser Leu Glu
        450                 455                 460 ctt gcg gag gag atc cgc cgc ctc gag gag gtc ttc cgc ttg gcg        1440
Leu Ala Glu Glu Ile Arg Arg Leu Glu Glu Val Phe Arg Leu Ala
465                 470                 475                 480 ggc cac ccc ttc aac ctc aac tcc cgg gac cag ctg gaa agg gtg ctc    1488
Gly His Pro Phe Asn Leu Asn Ser Arg Asp Gln Leu Glu Arg Val Leu
                    485                 490                 495 ttt gac gag ctt agg ctt ccc gcc ttg ggg aag acg caa aag aca ggc    1536
Phe Asp Glu Leu Arg Leu Pro Ala Leu Gly Lys Thr Gln Lys Thr Gly
            500                 505                 510 aag cgc tcc acc agc gcc gcg gtg ctg gag gcc cta cgg gag gcc cac    1584
Lys Arg Ser Thr Ser Ala Ala Val Leu Glu Ala Leu Arg Glu Ala His
        515                 520                 525 ccc atc gtg gag aag atc ctc cag cac cgg gag ctc acc aag ctc aag    1632
Pro Ile Val Glu Lys Ile Leu Gln His Arg Glu Leu Thr Lys Leu Lys
    530                 535                 540 aac acc tac gtg gac ccc ctc cca agc ctc gtc cac ccg agg acg ggc    1680
Asn Thr Tyr Val Asp Pro Leu Pro Ser Leu Val His Pro Arg Thr Gly
545                 550                 555                 560 cgc ctc cac acc cgc ttc aac cag acg gcc acg gcc acg ggg agg ctt    1728
Arg Leu His Thr Arg Phe Asn Gln Thr Ala Thr Ala Thr Gly Arg Leu
                565                 570                 575 agt agc tcc gac ccc aac ctg cag aac atc ccc gtc cgc acc ccc ttg    1776
Ser Ser Ser Asp Pro Asn Leu Gln Asn Ile Pro Val Arg Thr Pro Leu
            580                 585                 590 ggc cag agg atc cgc cgg gcc ttc gtg gcc gag gcg ggt tgg gcg ttg    1824
Gly Gln Arg Ile Arg Arg Ala Phe Val Ala Glu Ala Gly Trp Ala Leu
        595                 600                 605 gtg gcc ctg gac tat agc cag ata gag ctc cgc gtc ctc gcc cac ctc    1872
Val Ala Leu Asp Tyr Ser Gln Ile Glu Leu Arg Val Leu Ala His Leu
    610                 615                 620 tcc ggg gac gaa aac ctg atc agg gtc ttc cag gag ggg aag gac atc    1920
Ser Gly Asp Glu Asn Leu Ile Arg Val Phe Gln Glu Gly Lys Asp Ile
625                 630                 635                 640 cac acc cag acc gca agc tgg atg ttc ggc gtc ccc ccg gag gcc gtg    1968
His Thr Gln Thr Ala Ser Trp Met Phe Gly Val Pro Pro Glu Ala Val
                645                 650                 655 gac ccc ctg atg cgc cgg gcg gcc aag acg gtg aac tac ggc gtc ctc    2016
Asp Pro Leu Met Arg Arg Ala Ala Lys Thr Val Asn Tyr Gly Val Leu
            660                 665                 670 tac ggc atg tcc gcc cat agg ctc tcc cag gag cta gcc atc ccc tac    2064
Tyr Gly Met Ser Ala His Arg Leu Ser Gln Glu Leu Ala Ile Pro Tyr
        675                 680                 685 gaa gaa gcg gtg gcc ttt ata gag cgc tac ttc caa agc ttc ccc aag    2112
Glu Glu Ala Val Ala Phe Ile Glu Arg Tyr Phe Gln Ser Phe Pro Lys
    690                 695                 700 gtg cgg gcc tgg ata gaa aag acc ctg gag gag ggg agg aag cgg ggc    2160
Val Arg Ala Trp Ile Glu Lys Thr Leu Glu Glu Gly Arg Lys Arg Gly
705                 710                 715                 720 tac gtg gaa acc ctc ttc gga aga agg cgc tac gtg ccc gac ctc aac    2208
Tyr Val Glu Thr Leu Phe Gly Arg Arg Arg Tyr Val Pro Asp Leu Asn
                725                 730                 735 gcc cgg gtg aag agc gtc agg gag gcc gcg gag cgc atg gcc ttc aac    2256
Ala Arg Val Lys Ser Val Arg Glu Ala Ala Glu Arg Met Ala Phe Asn
```

```
                    740                 745                 750
atg ccc gtc cag ggc acc gcc gcc gac ctc atg aag ctc gcc atg gtg    2304
Met Pro Val Gln Gly Thr Ala Ala Asp Leu Met Lys Leu Ala Met Val
        755                 760                 765 aag ctc ttc ccc cgc ctc cgg gag atg ggg gcc cgc atg ctc ctc cag    2352
Lys Leu Phe Pro Arg Leu Arg Glu Met Gly Ala Arg Met Leu Leu Gln
    770                 775                 780 gtc cac gac gag ctc ctc ctg gag gcc ccc caa gcg cgg gcc gag gag    2400
Val His Asp Glu Leu Leu Leu Glu Ala Pro Gln Ala Arg Ala Glu Glu
785                 790                 795                 800 gtg gcg gct ttg gcc aac gag gcc atg gag aag gcc tat ccc ctc gcc    2448
Val Ala Ala Leu Ala Asn Glu Ala Met Glu Lys Ala Tyr Pro Leu Ala
                805                 810                 815 gtg ccc ctg gag gtg gag gtg ggg atg ggg gag gac tgg ctt tcc gcc    2496
Val Pro Leu Glu Val Glu Val Gly Met Gly Glu Asp Trp Leu Ser Ala
            820                 825                 830 aag ggt tag                                                        2505
Lys Gly
```

<210> SEQ ID NO 2
<211> LENGTH: 834
<212> TYPE: PRT
<213> ORGANISM: Thermus thermophilus

<400> SEQUENCE: 2

```
Met Glu Ala Met Leu Pro Leu Phe Glu Pro Lys Gly Arg Val Leu Leu
1               5                   10                  15

Val Ala Gly His His Leu Ala Tyr Arg Thr Phe Phe Ala Leu Lys Gly
                20                  25                  30

Leu Thr Thr Ser Arg Gly Glu Pro Val Gln Ala Val Tyr Gly Phe Ala
            35                  40                  45

Lys Ser Leu Leu Lys Ala Leu Lys Glu Asp Gly Tyr Lys Ala Val Phe
        50                  55                  60

Val Val Phe Asp Ala Lys Ala Pro Ser Phe Arg His Glu Ala Tyr Glu
65                  70                  75                  80

Ala Tyr Lys Ala Gly Arg Ala Pro Thr Pro Glu Asp Phe Pro Arg Gln
                85                  90                  95

Leu Ala Leu Ile Lys Glu Leu Val Asp Leu Leu Gly Phe Thr Arg Leu
            100                 105                 110

Glu Val Pro Gly Tyr Glu Ala Asp Asp Val Leu Ala Thr Leu Ala Lys
        115                 120                 125

Lys Ala Glu Lys Glu Gly Tyr Glu Val Arg Ile Leu Thr Ala Asp Arg
    130                 135                 140

Asp Leu Tyr Gln Leu Val Ser Asp Arg Val Ala Val Leu His Pro Glu
145                 150                 155                 160

Thr Ala Asp Arg Asp Leu Tyr Gln Leu Val Ser Asp Arg Val Ala Val
                165                 170                 175

Leu His Pro Glu Gly His Leu Ile Thr Pro Glu Trp Leu Trp Glu Lys
            180                 185                 190

Tyr Gly Leu Arg Pro Glu Gln Trp Val Asp Phe Arg Ala Leu Val Gly
        195                 200                 205

Asp Pro Ser Asp Asn Leu Pro Gly Val Lys Gly Ile Gly Glu Lys Thr
    210                 215                 220

Ala Leu Lys Leu Leu Lys Glu Trp Gly Ser Leu Glu Asn Leu Leu Lys
225                 230                 235                 240

Leu Arg Leu Ser Leu Glu Leu Ser Arg Val Arg Thr Asp Leu Pro Leu
```

```
                245                 250                 255
Glu Val Asp Leu Ala Gln Gly Arg Glu Pro Asp Arg Glu Gly Leu Arg
                260                 265                 270

Ala Phe Leu Glu Arg Leu Glu Phe Gly Ser Leu Leu His Glu Phe Gly
            275                 280                 285

Leu Leu Glu Ala Pro Ala Pro Leu Glu Glu Ala Pro Trp Pro Pro Pro
            290                 295                 300

Glu Gly Ala Phe Val Gly Phe Val Leu Ser Arg Pro Glu Pro Met Trp
305                 310                 315                 320

Ala Glu Leu Lys Ala Leu Ala Ala Cys Arg Asp Gly Arg Val His Arg
                325                 330                 335

Ala Ala Asp Pro Leu Ala Gly Leu Lys Asp Leu Lys Glu Val Arg Gly
            340                 345                 350

Leu Leu Ala Lys Asp Leu Ala Val Leu Ala Ser Arg Glu Gly Leu Asp
            355                 360                 365

Leu Val Pro Gly Asp Asp Pro Met Leu Leu Ala Tyr Leu Leu Asp Pro
            370                 375                 380

Ser Asn Thr Thr Pro Glu Gly Val Ala Arg Arg Tyr Gly Gly Glu Trp
385                 390                 395                 400

Thr Glu Asp Ala Ala His Arg Ala Leu Leu Ser Glu Arg Leu His Arg
                405                 410                 415

Asn Leu Leu Lys Arg Leu Glu Gly Glu Glu Lys Leu Leu Trp Leu Tyr
            420                 425                 430

His Glu Val Glu Lys Pro Leu Ser Arg Val Leu Ala His Met Glu Ala
            435                 440                 445

Thr Gly Val Arg Leu Asp Val Ala Tyr Leu Gln Ala Leu Ser Leu Glu
            450                 455                 460

Leu Ala Glu Glu Ile Arg Arg Leu Glu Glu Val Phe Arg Leu Ala
465                 470                 475                 480

Gly His Pro Phe Asn Leu Asn Ser Arg Asp Gln Leu Glu Arg Val Leu
                485                 490                 495

Phe Asp Glu Leu Arg Leu Pro Ala Leu Gly Lys Thr Gln Lys Thr Gly
            500                 505                 510

Lys Arg Ser Thr Ser Ala Ala Val Leu Glu Ala Leu Arg Glu Ala His
            515                 520                 525

Pro Ile Val Glu Lys Ile Leu Gln His Arg Glu Leu Thr Lys Leu Lys
            530                 535                 540

Asn Thr Tyr Val Asp Pro Leu Pro Ser Leu Val His Pro Arg Thr Gly
545                 550                 555                 560

Arg Leu His Thr Arg Phe Asn Gln Thr Ala Thr Ala Thr Gly Arg Leu
                565                 570                 575

Ser Ser Ser Asp Pro Asn Leu Gln Asn Ile Pro Val Arg Thr Pro Leu
            580                 585                 590

Gly Gln Arg Ile Arg Arg Ala Phe Val Ala Glu Ala Gly Trp Ala Leu
            595                 600                 605

Val Ala Leu Asp Tyr Ser Gln Ile Glu Leu Arg Val Leu Ala His Leu
            610                 615                 620

Ser Gly Asp Glu Asn Leu Ile Arg Val Phe Gln Glu Gly Lys Asp Ile
625                 630                 635                 640

His Thr Gln Thr Ala Ser Trp Met Phe Gly Val Pro Pro Glu Ala Val
                645                 650                 655

Asp Pro Leu Met Arg Arg Ala Ala Lys Thr Val Asn Tyr Gly Val Leu
            660                 665                 670
```

Tyr Gly Met Ser Ala His Arg Leu Ser Gln Glu Leu Ala Ile Pro Tyr
            675                 680                 685

Glu Glu Ala Val Ala Phe Ile Glu Arg Tyr Phe Gln Ser Phe Pro Lys
    690                 695                 700

Val Arg Ala Trp Ile Glu Lys Thr Leu Glu Glu Gly Arg Lys Arg Gly
705                 710                 715                 720

Tyr Val Glu Thr Leu Phe Gly Arg Arg Tyr Val Pro Asp Leu Asn
                725                 730                 735

Ala Arg Val Lys Ser Val Arg Glu Ala Ala Glu Arg Met Ala Phe Asn
            740                 745                 750

Met Pro Val Gln Gly Thr Ala Ala Asp Leu Met Lys Leu Ala Met Val
            755                 760                 765

Lys Leu Phe Pro Arg Leu Arg Glu Met Gly Ala Arg Met Leu Leu Gln
            770                 775                 780

Val His Asp Glu Leu Leu Leu Glu Ala Pro Gln Ala Arg Ala Glu Glu
785                 790                 795                 800

Val Ala Ala Leu Ala Asn Glu Ala Met Glu Lys Ala Tyr Pro Leu Ala
            805                 810                 815

Val Pro Leu Glu Val Glu Val Gly Met Gly Glu Asp Trp Leu Ser Ala
            820                 825                 830

Lys Gly

<210> SEQ ID NO 3
<211> LENGTH: 591
<212> TYPE: DNA
<213> ORGANISM: Thermus sp.
<220> FEATURE:
<221> NAME/KEY: modified_base
<222> LOCATION: (4)
<223> OTHER INFORMATION: a, t, c or g
<220> FEATURE:
<221> NAME/KEY: modified_base
<222> LOCATION: (30)
<223> OTHER INFORMATION: a, t, c or g
<220> FEATURE:
<221> NAME/KEY: modified_base
<222> LOCATION: (36)
<223> OTHER INFORMATION: a, t, c or g
<220> FEATURE:
<221> NAME/KEY: modified_base
<222> LOCATION: (38)..(39)
<223> OTHER INFORMATION: a, t, c or g
<220> FEATURE:
<221> NAME/KEY: modified_base
<222> LOCATION: (43)..(46)
<223> OTHER INFORMATION: a, t, c or g
<220> FEATURE:
<221> NAME/KEY: modified_base
<222> LOCATION: (53)..(57)
<223> OTHER INFORMATION: a, t, c or g
<220> FEATURE:
<221> NAME/KEY: modified_base
<222> LOCATION: (59)
<223> OTHER INFORMATION: a, t, c or g
<220> FEATURE:
<221> NAME/KEY: modified_base
<222> LOCATION: (63)
<223> OTHER INFORMATION: a, t, c or g

<400> SEQUENCE: 3
attngacggc cagtggggat cttgcatgcn tgcagntnng ggnnnngggc ccnnnnntnc      60
ccnggtacct gagccgaatt cgtaatcatg gtcatagctg tttcctgtgt gaaattgtta    120
tccgctcaca attccacaca acatacgagc cggaagcata aagtgtaaag cctggggtgc    180

```
ctaatgagtg agctaactca cattaattgc gttgcgctca ctgcccgctt tccagtcggg      240
aaacctgtcg tgccagctgc attaatgaat cggccaacgc gcggggagag gcggtttgcg      300
tattgggcgc cagggtggtt tttcttttca ccagtgagac gggcaacagc tgattgccct      360
tcaccgcctg gccctgagag agttgcagca agcggtccac gctggtttgc cccagcaggc      420
gaaaatcctg tttgatggtg gttccgaaat cggcaaaatc ccttataaat caaaagaata      480
gcccgagatg ggttgagtgt tgttccagtt tggaacaaga gtccactatt aaagaacgtg      540
gactccaacg tcaaagggcg aaaaaccgtc tatcagggcg ataggcccac t              591
```

<210> SEQ ID NO 4
<211> LENGTH: 605
<212> TYPE: DNA
<213> ORGANISM: Thermus sp.
<220> FEATURE:
<221> NAME/KEY: modified_base
<222> LOCATION: (1)
<223> OTHER INFORMATION: a, t, c or g
<220> FEATURE:
<221> NAME/KEY: modified_base
<222> LOCATION: (512)
<223> OTHER INFORMATION: a, t, c or g

<400> SEQUENCE: 4

```
ngacggccag tgccaagctt gcatgcctgc aggtcgactc tagaggatcc ccgggtaccg       60
agctcgaatt cgtaatcatg gtcatagctg tttcctgtgt gaaattgtta tccgctcaca      120
attccacaca acatacgagc cggaagcata agtgtaaag  cctggggtgc ctaatgagtg      180
agctaactca cattaattgc gttgcgctca ctgcccgctt tccagtcggg aaacctgtcg      240
tgccagctgc attaatgaat cggccaacgc gcggggagag gcggtttgcg tattgggcgc      300
cagggtggtt tttcttttca ccagtgagac gggcaacagc tgattgccct tcaccgcctg      360
gccctgagag agttgcagca agcggtccac gctggtttgc cccagcaggc gaaaatcctg      420
tttgatggtg gttccgaaat cggcaaaatc ccttataaat caaaagaata gcccgagata      480
gggttgagtg ttgttccagt ttggaacaag antccactat taaagaacgt ggactccaac      540
gtcaaagggc gaaaaaccgt ctatcagggc gatggcccac tacgtgaacc atcacccaaa      600 tcaas                                                                 605
```

<210> SEQ ID NO 5
<211> LENGTH: 595
<212> TYPE: DNA
<213> ORGANISM: Thermus sp.
<220> FEATURE:
<221> NAME/KEY: modified_base
<222> LOCATION: (509)
<223> OTHER INFORMATION: a, t, c or g

<400> SEQUENCE: 5

```
cgacggcagt gccaaccttg catgcctgca ggtcgactct agaggacccc gggtaccgag       60
ctcgaattcg taatcatggt catagctgtt tcctgtgtga aattgttatc cgctcacaat      120
tccacacaac atacgagccg gaagcataaa gtgtaaagcc tggggtgcct aatgagtgag      180
ctaactcaca ttaattgcgt tcgctcactg cccgctttcc agtcgggaaa cctgtcgtgc      240
cagctgcatt aatgaatcgg ccaacgcgcg ggagaggcg  gtttgcgtat tgggcgccag      300
ggtgcttttt cttttcacca gtgagacggg caacagctga ttgcccttca ccgcctggcc      360
ctgagagagt tgcagcaagc ggtccacgct ggtttgcccc agcaggcgaa aatcctgttt      420
gatggtggtt ccgaaatcgg caaaatccct tataaatcaa agaatagcc  cgagataggg      480
```

```
ttgagtgttg ttccagtttg gaacaagant ccactattaa agaacgtgga ctccaacgtc      540
aaaggcgaaa aaccgtcta tcagggcgat ggcccactac gtgaaccatc accca            595
```

<210> SEQ ID NO 6
<211> LENGTH: 599
<212> TYPE: DNA
<213> ORGANISM: Thermus sp.
<220> FEATURE:
<221> NAME/KEY: modified_base
<222> LOCATION: (6)
<223> OTHER INFORMATION: a, t, c or g
<220> FEATURE:
<221> NAME/KEY: modified_base
<222> LOCATION: (437)
<223> OTHER INFORMATION: a, t, c or g
<220> FEATURE:
<221> NAME/KEY: modified_base
<222> LOCATION: (494)
<223> OTHER INFORMATION: a, t, c or g
<220> FEATURE:
<221> NAME/KEY: modified_base
<222> LOCATION: (532)
<223> OTHER INFORMATION: a, t, c or g
<220> FEATURE:
<221> NAME/KEY: modified_base
<222> LOCATION: (535)
<223> OTHER INFORMATION: a, t, c or g
<220> FEATURE:
<221> NAME/KEY: modified_base
<222> LOCATION: (553)
<223> OTHER INFORMATION: a, t, c or g
<220> FEATURE:
<221> NAME/KEY: modified_base
<222> LOCATION: (561)
<223> OTHER INFORMATION: a, t, c or g
<220> FEATURE:
<221> NAME/KEY: modified_base
<222> LOCATION: (573)
<223> OTHER INFORMATION: a, t, c or g
<220> FEATURE:
<221> NAME/KEY: modified_base
<222> LOCATION: (576)
<223> OTHER INFORMATION: a, t, c or g
<220> FEATURE:
<221> NAME/KEY: modified_base
<222> LOCATION: (578)
<223> OTHER INFORMATION: a, t, c or g
<220> FEATURE:
<221> NAME/KEY: modified_base
<222> LOCATION: (584)..(585)
<223> OTHER INFORMATION: a, t, c or g
<220> FEATURE:
<221> NAME/KEY: modified_base
<222> LOCATION: (587)
<223> OTHER INFORMATION: a, t, c or g
<220> FEATURE:
<221> NAME/KEY: modified_base
<222> LOCATION: (590)..(591)
<223> OTHER INFORMATION: a, t, c or g
<220> FEATURE:
<221> NAME/KEY: modified_base
<222> LOCATION: (595)..(597)
<223> OTHER INFORMATION: a, t, c or g

<400> SEQUENCE: 6

```
cggcantgcc aaccttgcat gcctgcaggt cgactctaga aggaccccgg gtaccgagct      60
cgaattcgta atcatggtca tagctgtttc ctgtgtgaaa ttgttatccg ctcacaatcc      120
acacaacata cgagccggaa gcataaagtg taaagcctgg ggtgcctaat gagtgagcta      180
actcacatta attgcgttgc gctcactgcc cgctttccag tcgggaaacc tgtcgtgcca      240
gctgcattaa tgaatcggcc aacgcgcggg gagaggcggt ttgcgtattg ggcgccaggg      300
```

```
tggtttttct tttcaccagt gagacgggca acagctgatt gcccttcacc gcctggccct    360
gagagagttg cagcaagcgg tccacgctgg tttgcccag caggcgaaaa tcctgtttga    420
tggtggttcc gaaatcngca aaatcccctta taaatcaaaa gaatagcccg agatagggtt    480
gagtgttgtt ccantttgga acaagatcca ctattaaaga acgtggactc cnacntccaa    540
aggcgaaaaa ccntctatca ngggcaaagg ccnctncntt aacnncnccn natcnnntt    599
```

```
<210> SEQ ID NO 7
<211> LENGTH: 585
<212> TYPE: DNA
<213> ORGANISM: Thermus sp.
<220> FEATURE:
<221> NAME/KEY: modified_base
<222> LOCATION: (2)
<223> OTHER INFORMATION: a, t, c or g
<220> FEATURE:
<221> NAME/KEY: modified_base
<222> LOCATION: (11)
<223> OTHER INFORMATION: a, t, c or g
<220> FEATURE:
<221> NAME/KEY: modified_base
<222> LOCATION: (372)
<223> OTHER INFORMATION: a, t, c or g
<220> FEATURE:
<221> NAME/KEY: modified_base
<222> LOCATION: (385)
<223> OTHER INFORMATION: a, t, c or g
<220> FEATURE:
<221> NAME/KEY: modified_base
<222> LOCATION: (399)
<223> OTHER INFORMATION: a, t, c or g
<220> FEATURE:
<221> NAME/KEY: modified_base
<222> LOCATION: (401)
<223> OTHER INFORMATION: a, t, c or g
<220> FEATURE:
<221> NAME/KEY: modified_base
<222> LOCATION: (416)
<223> OTHER INFORMATION: a, t, c or g
<220> FEATURE:
<221> NAME/KEY: modified_base
<222> LOCATION: (421)
<223> OTHER INFORMATION: a, t, c or g
<220> FEATURE:
<221> NAME/KEY: modified_base
<222> LOCATION: (429)
<223> OTHER INFORMATION: a, t, c or g
<220> FEATURE:
<221> NAME/KEY: modified_base
<222> LOCATION: (435)
<223> OTHER INFORMATION: a, t, c or g
<220> FEATURE:
<221> NAME/KEY: modified_base
<222> LOCATION: (438)
<223> OTHER INFORMATION: a, t, c or g
<220> FEATURE:
<221> NAME/KEY: modified_base
<222> LOCATION: (446)
<223> OTHER INFORMATION: a, t, c or g
<220> FEATURE:
<221> NAME/KEY: modified_base
<222> LOCATION: (448)
<223> OTHER INFORMATION: a, t, c or g
<220> FEATURE:
<221> NAME/KEY: modified_base
<222> LOCATION: (450)..(452)
<223> OTHER INFORMATION: a, t, c or g
<220> FEATURE:
<221> NAME/KEY: modified_base
<222> LOCATION: (455)..(456)
<223> OTHER INFORMATION: a, t, c or g
<220> FEATURE:
<221> NAME/KEY: modified_base
<222> LOCATION: (459)
<223> OTHER INFORMATION: a, t, c or g
```

```
<220> FEATURE:
<221> NAME/KEY: modified_base
<222> LOCATION: (463)..(464)
<223> OTHER INFORMATION: a, t, c or g
<220> FEATURE:
<221> NAME/KEY: modified_base
<222> LOCATION: (468)
<223> OTHER INFORMATION: a, t, c or g
<220> FEATURE:
<221> NAME/KEY: modified_base
<222> LOCATION: (470)
<223> OTHER INFORMATION: a, t, c or g
<220> FEATURE:
<221> NAME/KEY: modified_base
<222> LOCATION: (473)..(474)
<223> OTHER INFORMATION: a, t, c or g
<220> FEATURE:
<221> NAME/KEY: modified_base
<222> LOCATION: (484)..(485)
<223> OTHER INFORMATION: a, t, c or g
<220> FEATURE:
<221> NAME/KEY: modified_base
<222> LOCATION: (487)
<223> OTHER INFORMATION: a, t, c or g
<220> FEATURE:
<221> NAME/KEY: modified_base
<222> LOCATION: (489)..(490)
<223> OTHER INFORMATION: a, t, c or g
<220> FEATURE:
<221> NAME/KEY: modified_base
<222> LOCATION: (492)
<223> OTHER INFORMATION: a, t, c or g
<220> FEATURE:
<221> NAME/KEY: modified_base
<222> LOCATION: (496)..(499)
<223> OTHER INFORMATION: a, t, c or g
<220> FEATURE:
<221> NAME/KEY: modified_base
<222> LOCATION: (501)
<223> OTHER INFORMATION: a, t, c or g
<220> FEATURE:
<221> NAME/KEY: modified_base
<222> LOCATION: (503)
<223> OTHER INFORMATION: a, t, c or g
<220> FEATURE:
<221> NAME/KEY: modified_base
<222> LOCATION: (505)
<223> OTHER INFORMATION: a, t, c or g
<220> FEATURE:
<221> NAME/KEY: modified_base
<222> LOCATION: (507)..(514)
<223> OTHER INFORMATION: a, t, c or g
<220> FEATURE:
<221> NAME/KEY: modified_base
<222> LOCATION: (516)..(518)
<223> OTHER INFORMATION: a, t, c or g
<220> FEATURE:
<221> NAME/KEY: modified_base
<222> LOCATION: (520)..(521)
<223> OTHER INFORMATION: a, t, c or g
<220> FEATURE:
<221> NAME/KEY: modified_base
<222> LOCATION: (524)
<223> OTHER INFORMATION: a, t, c or g
<220> FEATURE:
<221> NAME/KEY: modified_base
<222> LOCATION: (526)..(528)
<223> OTHER INFORMATION: a, t, c or g
<220> FEATURE:
<221> NAME/KEY: modified_base
<222> LOCATION: (530)
<223> OTHER INFORMATION: a, t, c or g
<220> FEATURE:
<221> NAME/KEY: modified_base
<222> LOCATION: (532)..(536)
<223> OTHER INFORMATION: a, t, c or g
<220> FEATURE:
<221> NAME/KEY: modified_base
<222> LOCATION: (539)..(540)
```

```
<223> OTHER INFORMATION: a, t, c or g
<220> FEATURE:
<221> NAME/KEY: modified_base
<222> LOCATION: (542)..(549)
<223> OTHER INFORMATION: a, t, c or g
<220> FEATURE:
<221> NAME/KEY: modified_base
<222> LOCATION: (551)..(555)
<223> OTHER INFORMATION: a, t, c or g
<220> FEATURE:
<221> NAME/KEY: modified_base
<222> LOCATION: (557)..(585)
<223> OTHER INFORMATION: a, t, c or g

<400> SEQUENCE: 7
cngcagtgcg nccttgcatg cctgcaggtc gactctagag gaccccgggt accgagctcg     60
aattcgtaat catggtcata gctgtttcct gtgtgaaatt gttatccgct cacaattcca    120
cacaacatac gagccggaag cataaagtgt aaagcctggg gtgcctaatg agtgagctaa    180
ctcacattaa ttgcgttgcg ctcactgccc gctttccagt cgggaaacct gtcgtgccag    240
ctgcattaat gaatcggcca acgcgcgggg agaggcggtt tgcgtattgg gcgccagggt    300
ggttttcctt ttcaccagtg gacgggcaa cagctgattg cccttcaccg cctggccctg    360
agagagttgc ancaagcggt ccacnctggt ttgccccanc angcgaaaat cctgtntgat    420
ngtggtccna aatcngcnaa atcccntntn nntcnnaana atnncccnan atnnggttga    480
gttnntncnn cnggannnna ntncncnnnn nnnnannntn nacncnnncn tnnnnnggnn    540
annnnnnnnt nnnnngnnnn nnnnnnnnnn nnnnnnnnnn nnnnn                    585

<210> SEQ ID NO 8
<211> LENGTH: 604
<212> TYPE: DNA
<213> ORGANISM: Thermus sp.
<220> FEATURE:
<221> NAME/KEY: modified_base
<222> LOCATION: (1)
<223> OTHER INFORMATION: a, t, c or g
<220> FEATURE:
<221> NAME/KEY: modified_base
<222> LOCATION: (266)
<223> OTHER INFORMATION: a, t, c or g
<220> FEATURE:
<221> NAME/KEY: modified_base
<222> LOCATION: (293)
<223> OTHER INFORMATION: a, t, c or g
<220> FEATURE:
<221> NAME/KEY: modified_base
<222> LOCATION: (299)
<223> OTHER INFORMATION: a, t, c or g
<220> FEATURE:
<221> NAME/KEY: modified_base
<222> LOCATION: (301)
<223> OTHER INFORMATION: a, t, c or g
<220> FEATURE:
<221> NAME/KEY: modified_base
<222> LOCATION: (304)
<223> OTHER INFORMATION: a, t, c or g
<220> FEATURE:
<221> NAME/KEY: modified_base
<222> LOCATION: (312)
<223> OTHER INFORMATION: a, t, c or g
<220> FEATURE:
<221> NAME/KEY: modified_base
<222> LOCATION: (332)
<223> OTHER INFORMATION: a, t, c or g
<220> FEATURE:
<221> NAME/KEY: modified_base
<222> LOCATION: (335)..(338)
<223> OTHER INFORMATION: a, t, c or g
<220> FEATURE:
```

```
<221> NAME/KEY: modified_base
<222> LOCATION: (341)
<223> OTHER INFORMATION: a, t, c or g
<220> FEATURE:
<221> NAME/KEY: modified_base
<222> LOCATION: (343)..(346)
<223> OTHER INFORMATION: a, t, c or g
<220> FEATURE:
<221> NAME/KEY: modified_base
<222> LOCATION: (349)..(350)
<223> OTHER INFORMATION: a, t, c or g
<220> FEATURE:
<221> NAME/KEY: modified_base
<222> LOCATION: (352)
<223> OTHER INFORMATION: a, t, c or g
<220> FEATURE:
<221> NAME/KEY: modified_base
<222> LOCATION: (358)
<223> OTHER INFORMATION: a, t, c or g
<220> FEATURE:
<221> NAME/KEY: modified_base
<222> LOCATION: (363)
<223> OTHER INFORMATION: a, t, c or g
<220> FEATURE:
<221> NAME/KEY: modified_base
<222> LOCATION: (366)
<223> OTHER INFORMATION: a, t, c or g
<220> FEATURE:
<221> NAME/KEY: modified_base
<222> LOCATION: (370)
<223> OTHER INFORMATION: a, t, c or g
<220> FEATURE:
<221> NAME/KEY: modified_base
<222> LOCATION: (372)..(375)
<223> OTHER INFORMATION: a, t, c or g
<220> FEATURE:
<221> NAME/KEY: modified_base
<222> LOCATION: (379)
<223> OTHER INFORMATION: a, t, c or g
<220> FEATURE:
<221> NAME/KEY: modified_base
<222> LOCATION: (385)
<223> OTHER INFORMATION: a, t, c or g
<220> FEATURE:
<221> NAME/KEY: modified_base
<222> LOCATION: (391)
<223> OTHER INFORMATION: a, t, c or g
<220> FEATURE:
<221> NAME/KEY: modified_base
<222> LOCATION: (393)..(395)
<223> OTHER INFORMATION: a, t, c or g
<220> FEATURE:
<221> NAME/KEY: modified_base
<222> LOCATION: (400)
<223> OTHER INFORMATION: a, t, c or g
<220> FEATURE:
<221> NAME/KEY: modified_base
<222> LOCATION: (403)
<223> OTHER INFORMATION: a, t, c or g
<220> FEATURE:
<221> NAME/KEY: modified_base
<222> LOCATION: (406)..(408)
<223> OTHER INFORMATION: a, t, c or g
<220> FEATURE:
<221> NAME/KEY: modified_base
<222> LOCATION: (422)
<223> OTHER INFORMATION: a, t, c or g
<220> FEATURE:
<221> NAME/KEY: modified_base
<222> LOCATION: (428)
<223> OTHER INFORMATION: a, t, c or g
<220> FEATURE:
<221> NAME/KEY: modified_base
<222> LOCATION: (432)
<223> OTHER INFORMATION: a, t, c or g
<220> FEATURE:
<221> NAME/KEY: modified_base
<222> LOCATION: (434)
<223> OTHER INFORMATION: a, t, c or g
```

```
<220> FEATURE:
<221> NAME/KEY: modified_base
<222> LOCATION: (436)..(438)
<223> OTHER INFORMATION: a, t, c or g
<220> FEATURE:
<221> NAME/KEY: modified_base
<222> LOCATION: (440)
<223> OTHER INFORMATION: a, t, c or g
<220> FEATURE:
<221> NAME/KEY: modified_base
<222> LOCATION: (442)
<223> OTHER INFORMATION: a, t, c or g
<220> FEATURE:
<221> NAME/KEY: modified_base
<222> LOCATION: (448)
<223> OTHER INFORMATION: a, t, c or g
<220> FEATURE:
<221> NAME/KEY: modified_base
<222> LOCATION: (455)
<223> OTHER INFORMATION: a, t, c or g
<220> FEATURE:
<221> NAME/KEY: modified_base
<222> LOCATION: (458)
<223> OTHER INFORMATION: a, t, c or g
<220> FEATURE:
<221> NAME/KEY: modified_base
<222> LOCATION: (469)
<223> OTHER INFORMATION: a, t, c or g
<220> FEATURE:
<221> NAME/KEY: modified_base
<222> LOCATION: (479)
<223> OTHER INFORMATION: a, t, c or g
<220> FEATURE:
<221> NAME/KEY: modified_base
<222> LOCATION: (484)
<223> OTHER INFORMATION: a, t, c or g
<220> FEATURE:
<221> NAME/KEY: modified_base
<222> LOCATION: (487)
<223> OTHER INFORMATION: a, t, c or g
<220> FEATURE:
<221> NAME/KEY: modified_base
<222> LOCATION: (491)
<223> OTHER INFORMATION: a, t, c or g
<220> FEATURE:
<221> NAME/KEY: modified_base
<222> LOCATION: (493)..(494)
<223> OTHER INFORMATION: a, t, c or g
<220> FEATURE:
<221> NAME/KEY: modified_base
<222> LOCATION: (528)
<223> OTHER INFORMATION: a, t, c or g
<220> FEATURE:
<221> NAME/KEY: modified_base
<222> LOCATION: (535)..(537)
<223> OTHER INFORMATION: a, t, c or g
<220> FEATURE:
<221> NAME/KEY: modified_base
<222> LOCATION: (539)
<223> OTHER INFORMATION: a, t, c or g
<220> FEATURE:
<221> NAME/KEY: modified_base
<222> LOCATION: (551)..(552)
<223> OTHER INFORMATION: a, t, c or g
<220> FEATURE:
<221> NAME/KEY: modified_base
<222> LOCATION: (568)
<223> OTHER INFORMATION: a, t, c or g
<220> FEATURE:
<221> NAME/KEY: modified_base
<222> LOCATION: (580)
<223> OTHER INFORMATION: a, t, c or g
<220> FEATURE:
<221> NAME/KEY: modified_base
<222> LOCATION: (582)..(584)
<223> OTHER INFORMATION: a, t, c or g
<220> FEATURE:
<221> NAME/KEY: modified_base
<222> LOCATION: (587)
```

<223> OTHER INFORMATION: a, t, c or g
<220> FEATURE:
<221> NAME/KEY: modified_base
<222> LOCATION: (589)
<223> OTHER INFORMATION: a, t, c or g
<220> FEATURE:
<221> NAME/KEY: modified_base
<222> LOCATION: (594)
<223> OTHER INFORMATION: a, t, c or g
<220> FEATURE:
<221> NAME/KEY: modified_base
<222> LOCATION: (602)..(603)
<223> OTHER INFORMATION: a, t, c or g

<400> SEQUENCE: 8

```
ngacgggcag tgccaagctt gcatgcctgc aggtcgactc tagaggatcc ccggggtacc      60
gagctcgaat tcgtaatcat ggtcatagct gtttcctgtg tgaaattgtt atccgctcac     120
aattccacac aacatacgag ccggaagcat aaagtgtaaa gcctggggtg cctaatgagt    180
gagctaactc acattaattg cgttgcgctc actgcccgct ttccagtcgg gaaacctgtc    240
gtgccagctg cattaatgaa tcggcnaacg cgcggggaga ggcggtttgt gtntttggnt    300
ncanggtggc cnttttttttt tttttttttt tntcnnnntc ncnnnnctnn anttttttntt  360
ctnttntttn tnnnntttnt ttttntttttt ntnnntatcn ctnccnnntt tttttttttt   420
tntttccncc tncntnnntn tnattttntt ttttntantt tttcctttnt tttttttttnt   480
tttntanttt ntnnccctc cccccctttcc cccccccccc cccccccncc ccccnnntnt    540
tttttttctt nnttttccat cccctccncc cccccttcn tnnnctntnt tttntttttt    600
tnnt                                                                  604
```

<210> SEQ ID NO 9
<211> LENGTH: 634
<212> TYPE: DNA
<213> ORGANISM: Thermus sp.
<220> FEATURE:
<221> NAME/KEY: modified_base
<222> LOCATION: (3)
<223> OTHER INFORMATION: a, t, c or g
<220> FEATURE:
<221> NAME/KEY: modified_base
<222> LOCATION: (114)
<223> OTHER INFORMATION: a, t, c or g
<220> FEATURE:
<221> NAME/KEY: modified_base
<222> LOCATION: (140)..(141)
<223> OTHER INFORMATION: a, t, c or g
<220> FEATURE:
<221> NAME/KEY: modified_base
<222> LOCATION: (156)
<223> OTHER INFORMATION: a, t, c or g
<220> FEATURE:
<221> NAME/KEY: modified_base
<222> LOCATION: (182)
<223> OTHER INFORMATION: a, t, c or g
<220> FEATURE:
<221> NAME/KEY: modified_base
<222> LOCATION: (184)
<223> OTHER INFORMATION: a, t, c or g
<220> FEATURE:
<221> NAME/KEY: modified_base
<222> LOCATION: (186)
<223> OTHER INFORMATION: a, t, c or g
<220> FEATURE:
<221> NAME/KEY: modified_base
<222> LOCATION: (194)
<223> OTHER INFORMATION: a, t, c or g
<220> FEATURE:
<221> NAME/KEY: modified_base
<222> LOCATION: (217)
<223> OTHER INFORMATION: a, t, c or g

```
<220> FEATURE:
<221> NAME/KEY: modified_base
<222> LOCATION: (226)
<223> OTHER INFORMATION: a, t, c or g
<220> FEATURE:
<221> NAME/KEY: modified_base
<222> LOCATION: (232)
<223> OTHER INFORMATION: a, t, c or g
<220> FEATURE:
<221> NAME/KEY: modified_base
<222> LOCATION: (239)
<223> OTHER INFORMATION: a, t, c or g
<220> FEATURE:
<221> NAME/KEY: modified_base
<222> LOCATION: (250)
<223> OTHER INFORMATION: a, t, c or g
<220> FEATURE:
<221> NAME/KEY: modified_base
<222> LOCATION: (255)
<223> OTHER INFORMATION: a, t, c or g
<220> FEATURE:
<221> NAME/KEY: modified_base
<222> LOCATION: (261)
<223> OTHER INFORMATION: a, t, c or g
<220> FEATURE:
<221> NAME/KEY: modified_base
<222> LOCATION: (271)
<223> OTHER INFORMATION: a, t, c or g
<220> FEATURE:
<221> NAME/KEY: modified_base
<222> LOCATION: (274)..(275)
<223> OTHER INFORMATION: a, t, c or g
<220> FEATURE:
<221> NAME/KEY: modified_base
<222> LOCATION: (277)..(278)
<223> OTHER INFORMATION: a, t, c or g
<220> FEATURE:
<221> NAME/KEY: modified_base
<222> LOCATION: (291)
<223> OTHER INFORMATION: a, t, c or g
<220> FEATURE:
<221> NAME/KEY: modified_base
<222> LOCATION: (301)
<223> OTHER INFORMATION: a, t, c or g
<220> FEATURE:
<221> NAME/KEY: modified_base
<222> LOCATION: (311)
<223> OTHER INFORMATION: a, t, c or g
<220> FEATURE:
<221> NAME/KEY: modified_base
<222> LOCATION: (321)..(322)
<223> OTHER INFORMATION: a, t, c or g
<220> FEATURE:
<221> NAME/KEY: modified_base
<222> LOCATION: (324)
<223> OTHER INFORMATION: a, t, c or g
<220> FEATURE:
<221> NAME/KEY: modified_base
<222> LOCATION: (329)
<223> OTHER INFORMATION: a, t, c or g
<220> FEATURE:
<221> NAME/KEY: modified_base
<222> LOCATION: (345)
<223> OTHER INFORMATION: a, t, c or g
<220> FEATURE:
<221> NAME/KEY: modified_base
<222> LOCATION: (350)..(351)
<223> OTHER INFORMATION: a, t, c or g
<220> FEATURE:
<221> NAME/KEY: modified_base
<222> LOCATION: (354)
<223> OTHER INFORMATION: a, t, c or g
<220> FEATURE:
<221> NAME/KEY: modified_base
<222> LOCATION: (363)
<223> OTHER INFORMATION: a, t, c or g
<220> FEATURE:
<221> NAME/KEY: modified_base
<222> LOCATION: (373)
```

```
<223> OTHER INFORMATION: a, t, c or g
<220> FEATURE:
<221> NAME/KEY: modified_base
<222> LOCATION: (382)
<223> OTHER INFORMATION: a, t, c or g
<220> FEATURE:
<221> NAME/KEY: modified_base
<222> LOCATION: (384)
<223> OTHER INFORMATION: a, t, c or g
<220> FEATURE:
<221> NAME/KEY: modified_base
<222> LOCATION: (396)
<223> OTHER INFORMATION: a, t, c or g
<220> FEATURE:
<221> NAME/KEY: modified_base
<222> LOCATION: (402)
<223> OTHER INFORMATION: a, t, c or g
<220> FEATURE:
<221> NAME/KEY: modified_base
<222> LOCATION: (405)..(406)
<223> OTHER INFORMATION: a, t, c or g
<220> FEATURE:
<221> NAME/KEY: modified_base
<222> LOCATION: (414)
<223> OTHER INFORMATION: a, t, c or g
<220> FEATURE:
<221> NAME/KEY: modified_base
<222> LOCATION: (417)
<223> OTHER INFORMATION: a, t, c or g
<220> FEATURE:
<221> NAME/KEY: modified_base
<222> LOCATION: (431)
<223> OTHER INFORMATION: a, t, c or g
<220> FEATURE:
<221> NAME/KEY: modified_base
<222> LOCATION: (438)
<223> OTHER INFORMATION: a, t, c or g
<220> FEATURE:
<221> NAME/KEY: modified_base
<222> LOCATION: (452)
<223> OTHER INFORMATION: a, t, c or g
<220> FEATURE:
<221> NAME/KEY: modified_base
<222> LOCATION: (461)
<223> OTHER INFORMATION: a, t, c or g
<220> FEATURE:
<221> NAME/KEY: modified_base
<222> LOCATION: (464)
<223> OTHER INFORMATION: a, t, c or g
<220> FEATURE:
<221> NAME/KEY: modified_base
<222> LOCATION: (468)
<223> OTHER INFORMATION: a, t, c or g
<220> FEATURE:
<221> NAME/KEY: modified_base
<222> LOCATION: (491)
<223> OTHER INFORMATION: a, t, c or g
<220> FEATURE:
<221> NAME/KEY: modified_base
<222> LOCATION: (507)
<223> OTHER INFORMATION: a, t, c or g
<220> FEATURE:
<221> NAME/KEY: modified_base
<222> LOCATION: (510)
<223> OTHER INFORMATION: a, t, c or g
<220> FEATURE:
<221> NAME/KEY: modified_base
<222> LOCATION: (526)
<223> OTHER INFORMATION: a, t, c or g
<220> FEATURE:
<221> NAME/KEY: modified_base
<222> LOCATION: (531)
<223> OTHER INFORMATION: a, t, c or g
<220> FEATURE:
<221> NAME/KEY: modified_base
<222> LOCATION: (533)
<223> OTHER INFORMATION: a, t, c or g
<220> FEATURE:
<221> NAME/KEY: modified_base
```

<222> LOCATION: (540)
<223> OTHER INFORMATION: a, t, c or g
<220> FEATURE:
<221> NAME/KEY: modified_base
<222> LOCATION: (544)
<223> OTHER INFORMATION: a, t, c or g
<220> FEATURE:
<221> NAME/KEY: modified_base
<222> LOCATION: (564)
<223> OTHER INFORMATION: a, t, c or g
<220> FEATURE:
<221> NAME/KEY: modified_base
<222> LOCATION: (571)
<223> OTHER INFORMATION: a, t, c or g
<220> FEATURE:
<221> NAME/KEY: modified_base
<222> LOCATION: (574)
<223> OTHER INFORMATION: a, t, c or g
<220> FEATURE:
<221> NAME/KEY: modified_base
<222> LOCATION: (583)
<223> OTHER INFORMATION: a, t, c or g
<220> FEATURE:
<221> NAME/KEY: modified_base
<222> LOCATION: (594)
<223> OTHER INFORMATION: a, t, c or g
<220> FEATURE:
<221> NAME/KEY: modified_base
<222> LOCATION: (604)
<223> OTHER INFORMATION: a, t, c or g
<220> FEATURE:
<221> NAME/KEY: modified_base
<222> LOCATION: (608)..(609)
<223> OTHER INFORMATION: a, t, c or g
<220> FEATURE:
<221> NAME/KEY: modified_base
<222> LOCATION: (615)
<223> OTHER INFORMATION: a, t, c or g
<220> FEATURE:
<221> NAME/KEY: modified_base
<222> LOCATION: (617)
<223> OTHER INFORMATION: a, t, c or g
<220> FEATURE:
<221> NAME/KEY: modified_base
<222> LOCATION: (629)
<223> OTHER INFORMATION: a, t, c or g

<400> SEQUENCE: 9

| | | | | | |
|---|---|---|---|---|---|
| atngaacggg | cagtgccaag | cttgcatgcc | tgcaggtcga | actctagagg | atccccgggg | 60 |
| taccgagctc | gaattcgtaa | tcatggtcat | agctgtttcc | tgtgtgaaat | tgtnatccgc | 120 |
| tcacaattcc | acacaacatn | nagccggaag | cataangtgt | taagcctggg | gtgcctattg | 180 |
| antnancaat | ctcncatttt | tttatctctc | tctcacnttt | cttttntttc | cngcacatna | 240 |
| ccctcctcn | atttntattc | ntttccttaa | ncanncnncc | tccatcctta | ntccctcctt | 300 |
| nttttccttc | nttccctcc | nncncccnt | tttttttttt | ttcancccn | ntcnccttcc | 360 |
| ttnctccttc | ttntctttc | tntncccttc | ctattntttc | tnctnncttt | ctcntanccc | 420 |
| ctcccctaat | ntcttttnct | tctttctct | cnccccttt | nccnccntc | tctcttttct | 480 |
| tcttcccctc | ncattatttt | ttcttcnctn | ccattctctt | ctctcnttcc | ncntattatn | 540 |
| ctcnttcctc | tatcctttcc | cccnctcatt | nccncccatc | ctnatttatc | ttcncttttt | 600 |
| cccntttnnc | ttatncnttt | ccctctctnc | atcc | | | 634 |

<210> SEQ ID NO 10
<211> LENGTH: 597
<212> TYPE: DNA
<213> ORGANISM: Thermus sp.
<220> FEATURE:
<221> NAME/KEY: modified_base
<222> LOCATION: (12)

<223> OTHER INFORMATION: a, t, c or g
<220> FEATURE:
<221> NAME/KEY: modified_base
<222> LOCATION: (25)
<223> OTHER INFORMATION: a, t, c or g
<220> FEATURE:
<221> NAME/KEY: modified_base
<222> LOCATION: (30)
<223> OTHER INFORMATION: a, t, c or g
<220> FEATURE:
<221> NAME/KEY: modified_base
<222> LOCATION: (468)
<223> OTHER INFORMATION: a, t, c or g
<220> FEATURE:
<221> NAME/KEY: modified_base
<222> LOCATION: (475)
<223> OTHER INFORMATION: a, t, c or g
<220> FEATURE:
<221> NAME/KEY: modified_base
<222> LOCATION: (499)
<223> OTHER INFORMATION: a, t, c or g
<220> FEATURE:
<221> NAME/KEY: modified_base
<222> LOCATION: (560)
<223> OTHER INFORMATION: a, t, c or g

<400> SEQUENCE: 10

| | | | | | |
|---|---|---|---|---|---|
| gacggcatgc | cntgcttgca | tgtcnactcn | tcaggatccc | cgggtaccga | gctcgaattc | 60 |
| gtaatcatgg | tcatagctgt | ttcctgtgtg | aaattgttat | ccgctcacaa | ttccacaca | 120 |
| catacgagcc | ggaagcataa | agtgtaaagc | ctggggtgcc | taatgagtga | gctaactcac | 180 |
| attaattgcg | ttgcgctcac | tgcccgcttt | ccagtcggga | aacctgtcgt | gccagctgca | 240 |
| ttaatgaatc | ggccaacgcg | cggggagagg | cggtttgcgt | attgggcgcc | agggtggttt | 300 |
| ttcttttcac | cagtgagacg | ggcaacagct | gattgccctt | caccgcctgg | ccctgagaga | 360 |
| gttgcagcaa | gcggtccacg | ctggtttgcc | ccagcaggcg | aaaatcctgt | ttgatggtgg | 420 |
| ttccgaaatc | ggcaaaatcc | cttataaatc | aaaagaatac | cgagatangg | ttgantgttg | 480 |
| ttccagtttg | gaacaagant | ccactattaa | agaacgtgga | ctccaacgtc | aaagggcgaa | 540 |
| aaaccgtcta | tcagggcgan | ggcccactac | gtgaaccatc | accaaatcaa | ttttttts | 597 |

<210> SEQ ID NO 11
<211> LENGTH: 598
<212> TYPE: DNA
<213> ORGANISM: Thermus sp.
<220> FEATURE:
<221> NAME/KEY: modified_base
<222> LOCATION: (1)
<223> OTHER INFORMATION: a, t, c or g
<220> FEATURE:
<221> NAME/KEY: modified_base
<222> LOCATION: (15)
<223> OTHER INFORMATION: a, t, c or g
<220> FEATURE:
<221> NAME/KEY: modified_base
<222> LOCATION: (512)
<223> OTHER INFORMATION: a, t, c or g

<400> SEQUENCE: 11

| | | | | | |
|---|---|---|---|---|---|
| ngacggccag | tgccnagctt | gcatgcctgc | aggtcgactc | tagaggatcc | ccgggtaccg | 60 |
| agctcgaatt | cgtaatcatg | gtcatagctg | tttcctgtgt | gaaattgtta | tccgctcaca | 120 |
| attccacaca | acatacgagc | cggaagcata | aagtgtaaag | cctggggtgc | ctaatgagtg | 180 |
| agctaactca | cattaattgc | gttgcgctca | ctgcccgctt | tccagtcggg | aaacctgtcg | 240 |
| tgccagctgc | attaatgaat | cggccaacgc | gcggggagag | gcggtttgcg | tattgggcgc | 300 |

-continued

```
cagggtggtt tttcttttca ccagtgagac gggcaacagc tgattgccct tcaccgcctg    360
gccctgagag agttgcagca agcggtccac gctggtttgc cccagcaggc gaaaatcctg    420
tttgatggtg gttccgaaat cggcaaaatc ccttataaat caaaagaata gcccgagata    480
gggttgagtg ttgttccagt ttggaacaag antccactat taaagaacgt ggactccaac    540
gtcaaagggc gaaaaacgtc tatcagggcg atggcccact acgtgaacca tcacccaa      598
```

<210> SEQ ID NO 12
<211> LENGTH: 605
<212> TYPE: DNA
<213> ORGANISM: Thermus sp.
<220> FEATURE:
<221> NAME/KEY: modified_base
<222> LOCATION: (2)..(12)
<223> OTHER INFORMATION: a, t, c or g
<220> FEATURE:
<221> NAME/KEY: modified_base
<222> LOCATION: (27)
<223> OTHER INFORMATION: a, t, c or g
<220> FEATURE:
<221> NAME/KEY: modified_base
<222> LOCATION: (523)
<223> OTHER INFORMATION: a, t, c or g

<400> SEQUENCE: 12

```
tnnnnnnnnn nnattgacgg caatgcnact tgcatgcctg caggtcgact ctagaggatc    60
cccgggtacc gagctcgaat tcgtaatcat ggtcatagct gtttcctgtg tgaaattgtt    120
atccgctcac aattccacac aacatacgag ccggaagcat aaagtgtaaa gcctggggtg    180
cctaatgagt gagctaactc acattaattg cgttgcgctc actgcccgct ttcgagtcgg    240
gaaacctgtc gtgccagctg cattaatgaa tcggccaacg cgcggggaga ggcggtttgc    300
gtattgggcg ccaggtggt ttttcttttc accagtgaga cgggcaacag ctgattgccc    360
ttcaccgcct ggccctgaga gagttgcagc aagcggtcca gctggtttg ccccagcagg    420 cgaaaatcct gtttgatggt ggttccgaaa tcggcaaaat cccttataaa tcaaaagaat    480
agcccgagat agggttgagt gttgttccag tttggaacaa gantccacta ttaaagaacg    540
tggactccaa cgtcaaaggg cgaaaaaccg tctatcaggg cgatggccca ctacgtgaac    600
catca                                                                605
```

<210> SEQ ID NO 13
<211> LENGTH: 596
<212> TYPE: DNA
<213> ORGANISM: Thermus sp.
<220> FEATURE:
<221> NAME/KEY: modified_base
<222> LOCATION: (14)
<223> OTHER INFORMATION: a, t, c or g
<220> FEATURE:
<221> NAME/KEY: modified_base
<222> LOCATION: (508)
<223> OTHER INFORMATION: a, t, c or g

<400> SEQUENCE: 13

```
gacggccagt gccnagcttg catgcctgca ggtcgactct agaggacccc gggtaccgag    60
ctcgaattcg taatcatggt catagctgtt tcctgtgtga aattgttatc cgctcacaat    120
tccacacaac atacgagccg gaagcataaa gtgtaaagcc tggggtgcct aatgagtgag    180
ctaactcaca ttaattgcgt tgcgctcact gcccgctttc cagtcgggaaa cctgtcgtgc    240 cagctgcatt aatgaatcgg ccaacgcgcg gggagaggcg gtttgcgtat tgggcgccag    300
ggtggttttt cttttcacca gtgagacggg caacagctga ttgcccttca ccgcctggcc    360
```

```
ctgagagagt tgcagcaagc ggtccacgct ggtttgcccc agcaggcgaa aatcctgttt      420
gatggtggtt ccgaaatcgg caaaatccct tataaatcaa agaatagcc gagatagggt        480 tgagtgttgt tccagtttgg aacaagantc cactattaaa gaacgtggac tccaacgtca      540
aagggcgaaa aaccgtctat cagggcgatg gcccactacg tgaaccatca cccaaa          596
```

<210> SEQ ID NO 14
<211> LENGTH: 602
<212> TYPE: DNA
<213> ORGANISM: Thermus sp.
<220> FEATURE:
<221> NAME/KEY: modified_base
<222> LOCATION: (2)..(3)
<223> OTHER INFORMATION: a, t, c or g
<220> FEATURE:
<221> NAME/KEY: modified_base
<222> LOCATION: (5)..(10)
<223> OTHER INFORMATION: a, t, c or g
<220> FEATURE:
<221> NAME/KEY: modified_base
<222> LOCATION: (26)..(27)
<223> OTHER INFORMATION: a, t, c or g
<220> FEATURE:
<221> NAME/KEY: modified_base
<222> LOCATION: (381)
<223> OTHER INFORMATION: a, t, c or g
<220> FEATURE:
<221> NAME/KEY: modified_base
<222> LOCATION: (555)
<223> OTHER INFORMATION: a, t, c or g
<220> FEATURE:
<221> NAME/KEY: modified_base
<222> LOCATION: (574)
<223> OTHER INFORMATION: a, t, c or g
<220> FEATURE:
<221> NAME/KEY: modified_base
<222> LOCATION: (576)
<223> OTHER INFORMATION: a, t, c or g
<220> FEATURE:
<221> NAME/KEY: modified_base
<222> LOCATION: (582)
<223> OTHER INFORMATION: a, t, c or g

<400> SEQUENCE: 14

```
tnntnnnnnn atttgacggc agtgcnncct tgcatgcctg caggtcgact ctagaggacc       60
ccgggtaccg agctcgaatt cgtaatcatg gtcatagctg tttcctgtgt gaaattgtta      120
tccgctcaca attccacaca acatacgaag ccggaagcat aaagtgtaaa gcctggggtg     180
cctaatgagt gagctaactc acattaattg cgttgcgctc actgcccgct ttccagtcgg     240
gaaacctgtc gtgccagctg cattaatgaa tcggccaacg cgcggggaga ggcggtttgc     300
gtattgggcg ccaggtggt ttttctttc accagtgaga cgggcaacag ctgattgccc       360
ttcaccgcct ggccctgaga nagttgcagc aagccgtcca cgctggtttg ccccagcagg    420
cgaaaatcct gtttgatggt ggttccgaaa atcgcaaaat cccttataat caaaaaata     480 cccgaaatag ggttaatgtt gttccatttt ggaacaaaat ccatattaaa aaagtggact   540
ccacgtcaaa gggcnaaaaa ccgctatcag ggcnagggc cnctacttta accatcccca    600
aa                                                                    602
```

<210> SEQ ID NO 15
<211> LENGTH: 602
<212> TYPE: DNA
<213> ORGANISM: Thermus sp.
<220> FEATURE:
<221> NAME/KEY: modified_base
<222> LOCATION: (1)

```
-continued

<223> OTHER INFORMATION: a, t, c or g
<220> FEATURE:
<221> NAME/KEY: modified_base
<222> LOCATION: (324)
<223> OTHER INFORMATION: a, t, c or g
<220> FEATURE:
<221> NAME/KEY: modified_base
<222> LOCATION: (368)
<223> OTHER INFORMATION: a, t, c or g
<220> FEATURE:
<221> NAME/KEY: modified_base
<222> LOCATION: (378)
<223> OTHER INFORMATION: a, t, c or g
<220> FEATURE:
<221> NAME/KEY: modified_base
<222> LOCATION: (380)
<223> OTHER INFORMATION: a, t, c or g
<220> FEATURE:
<221> NAME/KEY: modified_base
<222> LOCATION: (382)
<223> OTHER INFORMATION: a, t, c or g
<220> FEATURE:
<221> NAME/KEY: modified_base
<222> LOCATION: (390)..(391)
<223> OTHER INFORMATION: a, t, c or g
<220> FEATURE:
<221> NAME/KEY: modified_base
<222> LOCATION: (393)..(394)
<223> OTHER INFORMATION: a, t, c or g
<220> FEATURE:
<221> NAME/KEY: modified_base
<222> LOCATION: (398)
<223> OTHER INFORMATION: a, t, c or g
<220> FEATURE:
<221> NAME/KEY: modified_base
<222> LOCATION: (402)
<223> OTHER INFORMATION: a, t, c or g
<220> FEATURE:
<221> NAME/KEY: modified_base
<222> LOCATION: (404)..(405)
<223> OTHER INFORMATION: a, t, c or g
<220> FEATURE:
<221> NAME/KEY: modified_base
<222> LOCATION: (407)..(408)
<223> OTHER INFORMATION: a, t, c or g
<220> FEATURE:
<221> NAME/KEY: modified_base
<222> LOCATION: (411)
<223> OTHER INFORMATION: a, t, c or g
<220> FEATURE:
<221> NAME/KEY: modified_base
<222> LOCATION: (414)..(416)
<223> OTHER INFORMATION: a, t, c or g
<220> FEATURE:
<221> NAME/KEY: modified_base
<222> LOCATION: (419)..(420)
<223> OTHER INFORMATION: a, t, c or g
<220> FEATURE:
<221> NAME/KEY: modified_base
<222> LOCATION: (422)..(424)
<223> OTHER INFORMATION: a, t, c or g
<220> FEATURE:
<221> NAME/KEY: modified_base
<222> LOCATION: (426)..(427)
<223> OTHER INFORMATION: a, t, c or g
<220> FEATURE:
<221> NAME/KEY: modified_base
<222> LOCATION: (430)
<223> OTHER INFORMATION: a, t, c or g
<220> FEATURE:
<221> NAME/KEY: modified_base
<222> LOCATION: (432)..(433)
<223> OTHER INFORMATION: a, t, c or g
<220> FEATURE:
<221> NAME/KEY: modified_base
<222> LOCATION: (435)..(436)
<223> OTHER INFORMATION: a, t, c or g
<220> FEATURE:
<221> NAME/KEY: modified_base
```

```
<222> LOCATION: (438)..(465)
<223> OTHER INFORMATION: a, t, c or g
<220> FEATURE:
<221> NAME/KEY: modified_base
<222> LOCATION: (467)..(473)
<223> OTHER INFORMATION: a, t, c or g
<220> FEATURE:
<221> NAME/KEY: modified_base
<222> LOCATION: (475)
<223> OTHER INFORMATION: a, t, c or g
<220> FEATURE:
<221> NAME/KEY: modified_base
<222> LOCATION: (477)..(479)
<223> OTHER INFORMATION: a, t, c or g
<220> FEATURE:
<221> NAME/KEY: modified_base
<222> LOCATION: (483)..(602)
<223> OTHER INFORMATION: a, t, c or g

<400> SEQUENCE: 15
ngacggccag tgccaagctt gcatgcctgc aggtcgactc tagaggatcc ccgggtaccg      60
agctcgaatt cgtaatcatg gtcatagctg tttcctgtgt gaaattgtta tccgctcaca     120
attccacaca acatacgagc cggaagcata agtgtaaag cctggggtgc ctaatgagtg      180
agctaactca cattaattgc gttgcgctca ctgcccgctt tccagtcggg aaacctgtcg     240
tgccagctgc attaatgaat cggccaacgc gcggggagag gcggtttgcg tattgggcgc     300
cagggtggtt tttcttttca ccantgagac gggcaacagc tgattgccct tcaccgcctg     360
gccctganag agttgcancn ancggtccan ncnngttngc cncnncnngc naanncccnn     420
tnnnanngtn gnncnnannn nnnnnnnnnn nnnnnnnnnn nnnnannnn nnnananng       480 gtnnnnnnnn nnnnnnnnnn nnnnnnnnnn nnnnnnnnnn nnnnnnnnnn nnnnnnnnnn     540
nnnnnnnnnn nnnnnnnnnn nnnnnnnnnn nnnnnnnnnn nnnnnnnnnn nnnnnnnnnn     600 nn                                                                    602

<210> SEQ ID NO 16
<211> LENGTH: 597
<212> TYPE: DNA
<213> ORGANISM: Thermus sp.
<220> FEATURE:
<221> NAME/KEY: modified_base
<222> LOCATION: (3)..(5)
<223> OTHER INFORMATION: a, t, c or g
<220> FEATURE:
<221> NAME/KEY: modified_base
<222> LOCATION: (8)
<223> OTHER INFORMATION: a, t, c or g
<220> FEATURE:
<221> NAME/KEY: modified_base
<222> LOCATION: (411)
<223> OTHER INFORMATION: a, t, c or g
<220> FEATURE:
<221> NAME/KEY: modified_base
<222> LOCATION: (445)
<223> OTHER INFORMATION: a, t, c or g
<220> FEATURE:
<221> NAME/KEY: modified_base
<222> LOCATION: (448)
<223> OTHER INFORMATION: a, t, c or g
<220> FEATURE:
<221> NAME/KEY: modified_base
<222> LOCATION: (460)
<223> OTHER INFORMATION: a, t, c or g
<220> FEATURE:
<221> NAME/KEY: modified_base
<222> LOCATION: (465)..(466)
<223> OTHER INFORMATION: a, t, c or g
<220> FEATURE:
<221> NAME/KEY: modified_base
<222> LOCATION: (469)
```

```
<223> OTHER INFORMATION: a, t, c or g
<220> FEATURE:
<221> NAME/KEY: modified_base
<222> LOCATION: (483)
<223> OTHER INFORMATION: a, t, c or g
<220> FEATURE:
<221> NAME/KEY: modified_base
<222> LOCATION: (494)..(495)
<223> OTHER INFORMATION: a, t, c or g
<220> FEATURE:
<221> NAME/KEY: modified_base
<222> LOCATION: (500)
<223> OTHER INFORMATION: a, t, c or g
<220> FEATURE:
<221> NAME/KEY: modified_base
<222> LOCATION: (502)..(503)
<223> OTHER INFORMATION: a, t, c or g
<220> FEATURE:
<221> NAME/KEY: modified_base
<222> LOCATION: (507)
<223> OTHER INFORMATION: a, t, c or g
<220> FEATURE:
<221> NAME/KEY: modified_base
<222> LOCATION: (509)..(511)
<223> OTHER INFORMATION: a, t, c or g
<220> FEATURE:
<221> NAME/KEY: modified_base
<222> LOCATION: (516)
<223> OTHER INFORMATION: a, t, c or g
<220> FEATURE:
<221> NAME/KEY: modified_base
<222> LOCATION: (518)
<223> OTHER INFORMATION: a, t, c or g
<220> FEATURE:
<221> NAME/KEY: modified_base
<222> LOCATION: (520)..(525)
<223> OTHER INFORMATION: a, t, c or g
<220> FEATURE:
<221> NAME/KEY: modified_base
<222> LOCATION: (528)
<223> OTHER INFORMATION: a, t, c or g
<220> FEATURE:
<221> NAME/KEY: modified_base
<222> LOCATION: (530)..(531)
<223> OTHER INFORMATION: a, t, c or g
<220> FEATURE:
<221> NAME/KEY: modified_base
<222> LOCATION: (533)
<223> OTHER INFORMATION: a, t, c or g
<220> FEATURE:
<221> NAME/KEY: modified_base
<222> LOCATION: (536)..(539)
<223> OTHER INFORMATION: a, t, c or g
<220> FEATURE:
<221> NAME/KEY: modified_base
<222> LOCATION: (542)
<223> OTHER INFORMATION: a, t, c or g
<220> FEATURE:
<221> NAME/KEY: modified_base
<222> LOCATION: (545)
<223> OTHER INFORMATION: a, t, c or g
<220> FEATURE:
<221> NAME/KEY: modified_base
<222> LOCATION: (549)
<223> OTHER INFORMATION: a, t, c or g
<220> FEATURE:
<221> NAME/KEY: modified_base
<222> LOCATION: (552)
<223> OTHER INFORMATION: a, t, c or g
<220> FEATURE:
<221> NAME/KEY: modified_base
<222> LOCATION: (554)
<223> OTHER INFORMATION: a, t, c or g
<220> FEATURE:
<221> NAME/KEY: modified_base
<222> LOCATION: (556)..(557)
<223> OTHER INFORMATION: a, t, c or g
<220> FEATURE:
<221> NAME/KEY: modified_base
```

<222> LOCATION: (560)..(565)
<223> OTHER INFORMATION: a, t, c or g
<220> FEATURE:
<221> NAME/KEY: modified_base
<222> LOCATION: (569)
<223> OTHER INFORMATION: a, t, c or g
<220> FEATURE:
<221> NAME/KEY: modified_base
<222> LOCATION: (571)
<223> OTHER INFORMATION: a, t, c or g
<220> FEATURE:
<221> NAME/KEY: modified_base
<222> LOCATION: (573)..(580)
<223> OTHER INFORMATION: a, t, c or g
<220> FEATURE:
<221> NAME/KEY: modified_base
<222> LOCATION: (582)..(597)
<223> OTHER INFORMATION: a, t, c or g

<400> SEQUENCE: 16

```
ttnnnacngc cagtgccaag cttgcatgcc tgcaggtcga ctctagagga tccccgggta    60
ccgagctcga attcgtaatc atggtcatag ctgtttcctg tgtgaaattg ttatccgctc   120
acaattccac acaacatacg agccggaagc ataaagtgta aagcctgggg tgcctaatga   180
gtgagctaac tcacattaat tgcgttgcgc tcactgcccg ctttccagtc gggaaacctg   240
tcgtgccagc tgcattaatg aatcggccaa cgcgcgggga gaggcggttt gcgtattggg   300
cgccagggtg ttttttcttt tcaccagtga cgggcaac agctgattgc ccttcaccgc     360
ctggccctga gagagttgca gcaagcggtc acgctggtt tgccccaaca ngcgaaaatc    420
ctgtttgatg gtggttccga aatcngcnaa atcccttatn aatcnnaana atacccgaga   480
tanggttgag tgtnntccan tnnggancnn natccncnan nnnnnacntn nanccnnnnt   540
cnaanggcna anancnngcn nnnnnggcna ngnnnnnnnn tnnnnnnnnn nnnnnnn      597
```

<210> SEQ ID NO 17
<211> LENGTH: 605
<212> TYPE: DNA
<213> ORGANISM: Thermus sp.
<220> FEATURE:
<221> NAME/KEY: modified_base
<222> LOCATION: (16)
<223> OTHER INFORMATION: a, t, c or g
<220> FEATURE:
<221> NAME/KEY: modified_base
<222> LOCATION: (511)
<223> OTHER INFORMATION: a, t, c or g
<220> FEATURE:
<221> NAME/KEY: modified_base
<222> LOCATION: (583)
<223> OTHER INFORMATION: a, t, c or g

<400> SEQUENCE: 17

```
cgacggccag taccgncttg catgcctgca ggtcgactct agaggatccc cgggtaccga    60
gctcgaattc gtaatcatgg tcatagctgt ttcctgtgtg aaattgttat ccgctcacaa   120
ttccacacaa catacgagcc ggaagcataa agtgtaaagc ctgggtgcc taatgagtga    180
gctaactcac attaattgcg ttgcgctcac tgcccgcttt ccagtcggga aacctgtcgt   240
gccagctgca ttaatgaatc ggccaacgcg cggggagagg cggtttgcgt attgggcgcc   300
aggtggtttt tcttttcac cagtgagacg ggcaacagct gattgcccctt caccgcctgg   360
ccctgagaga gttgcagcaa gcggtccacg ctggtttgcc ccagcaggcg aaaatcctgt   420
ttgatgtgtg ttccgaaatc ggcaaaatcc cttataaatc aaaagaatag cccgagatag   480
ggttgagtgt tgttccagtt tggaacaaga ntccactatt aaagaacgtg gactccaacg   540
```

```
tcaaagggcg aaaaaccgtc tatcagggc  gaaggccact acntgaacca tcacccaaat      600
caagt                                                                  605
```

<210> SEQ ID NO 18
<211> LENGTH: 601
<212> TYPE: DNA
<213> ORGANISM: Thermus sp.
<220> FEATURE:
<221> NAME/KEY: modified_base
<222> LOCATION: (1)
<223> OTHER INFORMATION: a, t, c or g
<220> FEATURE:
<221> NAME/KEY: modified_base
<222> LOCATION: (6)
<223> OTHER INFORMATION: a, t, c or g
<220> FEATURE:
<221> NAME/KEY: modified_base
<222> LOCATION: (14)
<223> OTHER INFORMATION: a, t, c or g
<220> FEATURE:
<221> NAME/KEY: modified_base
<222> LOCATION: (16)
<223> OTHER INFORMATION: a, t, c or g
<220> FEATURE:
<221> NAME/KEY: modified_base
<222> LOCATION: (405)
<223> OTHER INFORMATION: a, t, c or g
<220> FEATURE:
<221> NAME/KEY: modified_base
<222> LOCATION: (512)
<223> OTHER INFORMATION: a, t, c or g

<400> SEQUENCE: 18

```
nacggncatt gccnancttg catgccttgc aggtcgactc tagaggatcc ccgggtaccg       60
agctcgaatt cgtaatcatg gtcatagctg tttcctgtgt gaaattgtta tccgctcaca     120
attccacaca acatacgagc cggaagcata agtgtaaag  cctggggtgc ctaatgagtg     180
agctaactca cattaattgc gttgcgctca ctgcccgctt ccagtcggg  aaacctgtcg     240 tgccagctgc attaatgaat cggccaacgc gcggggagag gcggtttgcg tattgggcgc     300
cagggtggtt tttcttttca ccagtgagac gggcaacagc tgattgccct tcaccgcctg     360
gccctgagag agttgcagca agcggtccac gctggtttgc cccancaggc gaaaatcctg     420
tttgatggtg gttccgaaat cggcaaaatc ccttataaat caaagaata  gcccgagata     480 gggttgagtg ttgttccagt ttggaacaag antccactat taagaacgt  ggactccaac     540 gtcaaagggc gaaaaccgt  ctatcagggc gatgcccact acgtgaacca tcacccaaat     600
c                                                                     601
```

<210> SEQ ID NO 19
<211> LENGTH: 601
<212> TYPE: DNA
<213> ORGANISM: Thermus sp.
<220> FEATURE:
<221> NAME/KEY: modified_base
<222> LOCATION: (2)
<223> OTHER INFORMATION: a, t, c or g
<220> FEATURE:
<221> NAME/KEY: modified_base
<222> LOCATION: (580)
<223> OTHER INFORMATION: a, t, c or g

<400> SEQUENCE: 19

```
cngtcatacc gagcttgcat gcctgcaggt cgactctaga ggatcccggg gtaccgagct      60
cgaattcgta atcatggtca tagctgtttc ctgtgtgaaa ttgttatccg ctcacaattc     120
cacacaacat acgagccgga agcataaagt gtaaagcctg ggtgcctaa  tgagtgagct     180
```

```
aactcacatt aattgcgttg cgctcactgc ccgctttcca gtcgggaaac ctgtcgtgcc      240
agctgcatta atgaatcggc caacgcgcgg ggagaggcgg tttgcgtatt gggcgccagg      300
gtggtttttc ttttcaccag tgagacgggc aacagctgat tgcccttcac cgcctggccc      360
tgagagagtt gcagcaagcg gtccacgctg gtttgcccca gcaggcgaaa atcctgtttg      420
atggtggttc cgaaatcggc aaaatccctt ataaatcaaa agaatagccc gagatagggt      480
tgagtgttgt tccagtttgg aacaagagtc cactattaaa gaacgtggac tccaacgtca      540
aagggcgaaa aaccgtctat cagggcgatg gcccactacn tgaaccatca cccaaatcaa      600
g                                                                    601
```

<210> SEQ ID NO 20
<211> LENGTH: 619
<212> TYPE: DNA
<213> ORGANISM: Thermus sp.
<220> FEATURE:
<221> NAME/KEY: modified_base
<222> LOCATION: (1)
<223> OTHER INFORMATION: a, t, c or g
<220> FEATURE:
<221> NAME/KEY: modified_base
<222> LOCATION: (3)
<223> OTHER INFORMATION: a, t, c or g
<220> FEATURE:
<221> NAME/KEY: modified_base
<222> LOCATION: (373)
<223> OTHER INFORMATION: a, t, c or g
<220> FEATURE:
<221> NAME/KEY: modified_base
<222> LOCATION: (502)
<223> OTHER INFORMATION: a, t, c or g
<220> FEATURE:
<221> NAME/KEY: modified_base
<222> LOCATION: (514)
<223> OTHER INFORMATION: a, t, c or g
<220> FEATURE:
<221> NAME/KEY: modified_base
<222> LOCATION: (540)
<223> OTHER INFORMATION: a, t, c or g
<220> FEATURE:
<221> NAME/KEY: modified_base
<222> LOCATION: (573)
<223> OTHER INFORMATION: a, t, c or g
<220> FEATURE:
<221> NAME/KEY: modified_base
<222> LOCATION: (584)
<223> OTHER INFORMATION: a, t, c or g
<220> FEATURE:
<221> NAME/KEY: modified_base
<222> LOCATION: (590)
<223> OTHER INFORMATION: a, t, c or g
<220> FEATURE:
<221> NAME/KEY: modified_base
<222> LOCATION: (593)
<223> OTHER INFORMATION: a, t, c or g
<220> FEATURE:
<221> NAME/KEY: modified_base
<222> LOCATION: (595)
<223> OTHER INFORMATION: a, t, c or g
<220> FEATURE:
<221> NAME/KEY: modified_base
<222> LOCATION: (602)..(603)
<223> OTHER INFORMATION: a, t, c or g
<220> FEATURE:
<221> NAME/KEY: modified_base
<222> LOCATION: (606)
<223> OTHER INFORMATION: a, t, c or g

<400> SEQUENCE: 20

```
nangacggca gtgccaagct tgcatgcctg caggtcgact ctagaggatc cccgggtacc       60
```

-continued

| | |
|---|---|
| gagctcgaat tcgtaatcat ggtcatagct gtttcctgtg tgaaattgtt atccgctcac | 120 |
| aattccacac aacatacgag ccggaagcat aaagtgtaaa gcctggggtg cctaatgagt | 180 |
| gagctaactc acattaattg cgttgcgctc actgcccgct ttccagtcgg gaaacctgtc | 240 |
| gtgccagctg cattaatgaa tcggccaacg cgcggggaga ggcggtttgc gtattgggcg | 300 |
| ccagggtggt ttttcttttc accagtgaga cgggcaacag ctgattgccc ttcaccgcct | 360 |
| ggccctgaga ganttgcagc aagcggtcca cgctggtttg ccccagcagg cgaaaatcct | 420 |
| gtttgatggt ggttccgaaa tcggcaaaat cccttataaa tcaaaaagaa tagcccgaga | 480 |
| tagggttgag tgttgttccc antttgggaa caanaatccc acttattaaa gaaactggan | 540 |
| tcccaacgtc aaagggcgaa aaaaccgtc tancaggggc gaanggcccn ctncntgaac | 600 |
| cnnccnccccc aaatcaaat | 619 |

<210> SEQ ID NO 21
<211> LENGTH: 605
<212> TYPE: DNA
<213> ORGANISM: Thermus sp.
<220> FEATURE:
<221> NAME/KEY: modified_base
<222> LOCATION: (1)
<223> OTHER INFORMATION: a, t, c or g
<220> FEATURE:
<221> NAME/KEY: modified_base
<222> LOCATION: (5)
<223> OTHER INFORMATION: a, t, c or g
<220> FEATURE:
<221> NAME/KEY: modified_base
<222> LOCATION: (18)
<223> OTHER INFORMATION: a, t, c or g
<220> FEATURE:
<221> NAME/KEY: modified_base
<222> LOCATION: (477)
<223> OTHER INFORMATION: a, t, c or g

<400> SEQUENCE: 21

| | |
|---|---|
| nttangacgg gccagtgnca atcttgcatg cctgcaggtc gactctagag gatccccggg | 60 |
| ttaccgagct cgaattcgta atcatggtca tagctgtttc ctgtgtgaaa ttgttatccg | 120 |
| ctcacaattc cacacaacat acgagccgga agcataaagt gtaaagcctg gggtgcctaa | 180 |
| tgagtgagct aactcacatt aattgcgttg cgctcactgc ccgctttcca gtcgggaaac | 240 |
| ctgtcgtgcc agctgcatta atgaatcggc caacgcgcgg ggagaggcgg tttgcgtatt | 300 |
| gggcgccagg gtggtttttc ttttcaccag tgagacgggc aacagctgat tgcccttcac | 360 |
| cgcctggccc tgagagagtt gcagcaagcg gtccacgctg gtttgcccca gcaggcgaaa | 420 |
| atcctgtttg atggtggttc cgaaatcggc aaaatccctt ataaatcaaa agaatagccc | 480 |
| gagatagggt tgagtgttgt tccagtttgg aacaagatcc actattaaag aacgtggact | 540 |
| ccaacgtcaa agggcgaaaa acgtctatca gggcganggc ccactacgtg aaccatcacc | 600 |
| caaat | 605 |

<210> SEQ ID NO 22
<211> LENGTH: 602
<212> TYPE: DNA
<213> ORGANISM: Thermus sp.
<220> FEATURE:
<221> NAME/KEY: modified_base
<222> LOCATION: (2)
<223> OTHER INFORMATION: a, t, c or g
<220> FEATURE:
<221> NAME/KEY: modified_base
<222> LOCATION: (569)
<223> OTHER INFORMATION: a, t, c or g
<220> FEATURE:
<221> NAME/KEY: modified_base
<222> LOCATION: (585)
<223> OTHER INFORMATION: a, t, c or g

<400> SEQUENCE: 22

| | | | | | |
|---|---|---|---|---|---|
| anttcattgc | caagcttgca | tgcctgcagg | tcgactctag | aggatcccg | ggtaccgagc | 60 |
| tcgaattcgt | aatcatggtc | atagctgttt | cctgtgtgaa | attgttatcc | gctcacaatt | 120 |
| ccacacaaca | tacgagccgg | aagcataaag | tgtaaagcct | ggggtgccta | atgagtgagc | 180 |
| taactcacat | taattgcgtt | gcgctcactg | cccgctttcc | agtcgggaaa | cctgtcgtgc | 240 |
| cagctgcatt | aatgaatcgg | ccaacgcgcg | gggagaggcg | gtttgcgtat | tgggcgccag | 300 |
| ggtggttttt | cttttcacca | gtgagacggg | caacagctga | ttgcccttca | ccgcctggcc | 360 |
| ctgagagagt | tgcagcaagc | ggtccacgct | ggtttgcccc | agcaggcgaa | atcctgtttt | 420 |
| gatggtggtt | ccgaaatcgg | caaatccct | tataaatcaa | agaatagcc | cgagataggg | 480 |
| ttgagtgttg | ttccagtttg | gaacaagatc | cactattaaa | gaacgtggac | tccaacgtca | 540 |
| aagggcgaaa | aaccgtctat | cagggcgang | gcccactacg | tgaancatca | ccaaatcaag | 600 |
| tt | | | | | | 602 |

<210> SEQ ID NO 23
<211> LENGTH: 605
<212> TYPE: DNA
<213> ORGANISM: Thermus sp.
<220> FEATURE:
<221> NAME/KEY: modified_base
<222> LOCATION: (1)
<223> OTHER INFORMATION: a, t, c or g
<220> FEATURE:
<221> NAME/KEY: modified_base
<222> LOCATION: (512)
<223> OTHER INFORMATION: a, t, c or g

<400> SEQUENCE: 23

| | | | | | |
|---|---|---|---|---|---|
| ngacggccag | tgccaagctt | gcatgcctgc | aggtcgactc | tagaggatcc | ccgggtaccg | 60 |
| agctcgaatt | cgtaatcatg | gtcatagctg | tttcctgtgt | gaaattgtta | tccgctcaca | 120 |
| attccacaca | acatacgagc | cggaagcata | aagtgtaaag | cctggggtgc | ctaatgagtg | 180 |
| agctaactca | cattaattgc | gttgcgctca | ctgcccgctt | tccagtcggg | aaacctgtcg | 240 |
| tgccagctgc | attaatgaat | cggccaacgc | gcggggagag | gcggtttgcg | tattgggcgc | 300 |
| cagggtggtt | tttcttttca | ccagtgagac | gggcaacagc | tgattgccct | tcaccgcctg | 360 |
| gccctgagag | agttgcagca | agcggtccac | gctggtttgc | cccagcaggc | gaaaatcctg | 420 |
| tttgatggtg | gttccgaaat | cggcaaaatc | ccttataaat | caaagaata | gcccgagata | 480 |
| gggttgagtg | ttgttccagt | ttggaacaag | antccactat | taaagaacgt | ggactccaac | 540 |
| gtcaagggc | gaaaaaccgt | ctatcagggc | gatggcccac | tacgtgaacc | atcacccaaa | 600 |
| tcaas | | | | | | 605 |

<210> SEQ ID NO 24
<211> LENGTH: 604
<212> TYPE: DNA
<213> ORGANISM: Thermus sp.
<220> FEATURE:
<221> NAME/KEY: modified_base
<222> LOCATION: (512)
<223> OTHER INFORMATION: a, t, c or g

<400> SEQUENCE: 24

```
cgacggccag tgccaagctt gcatgcctgc aggtcgactc tagaggatcc ccgggtaccg      60
agctcgaatt cgtaatcatg gtcatagctg tttcctgtgt gaaattgtta tccgctcaca     120
attccacaca acatacgagc cggaagcata aagtgtaaag cctggggtgc ctaatgagtg     180
agctaactca cattaattgc gttgcgctca ctgcccgctt tccagtcggg aaacctgtcg     240
tgccagctgc attaatgaat cggccaacgc gcggggagag gcggtttgcg tattgggcgc     300
cagggtggtt tttcttttca ccagtgagac gggcaacagc tgattgccct tcaccgcctg     360
gccctgagag agttgcagca agcggtccac gctggtttgc cccagcaggc gaaaatcctg     420
tttgatggtg gttccgaaat cggcaaaatc ccttataaat caaaagaata gcccgagata     480
gggttgagtg ttgttccagt ttggaacaag antccactat taaagaacgt ggactccaac     540
gtcaaagggc gaaaaacgtc tatcagggcg atggcccact acgtgaacca tcacccaaat     600
caag                                                                  604
```

```
<210> SEQ ID NO 25
<211> LENGTH: 45
<212> TYPE: DNA
<213> ORGANISM: Artificial Sequence
<220> FEATURE:
<223> OTHER INFORMATION: Description of Artificial Sequence: Primer

<400> SEQUENCE: 25
ctgttcgaac ccaaaggccg tgtcctcctg gtggccggcc accac                      45

<210> SEQ ID NO 26
<211> LENGTH: 24
<212> TYPE: DNA
<213> ORGANISM: Artificial Sequence
<220> FEATURE:
<223> OTHER INFORMATION: Description of Artificial Sequence: Primer

<400> SEQUENCE: 26
gaggctgccg aattccagcc tctc                                             24

<210> SEQ ID NO 27
<211> LENGTH: 23
<212> TYPE: DNA
<213> ORGANISM: Artificial Sequence
<220> FEATURE:
<223> OTHER INFORMATION: Description of Artificial Sequence: Primer

<400> SEQUENCE: 27
gttttcccag tcacgacgtt gta                                              23
```

FY7 POLYMERASE

CROSS-REFERENCE TO RELATED APPLICATIONS

This application claims priority to United States Provisional Application Serial No. 60/089,556, filed on Jun. 17, 1998, the entire disclosure of which is incorporated in its herein.

BACKGROUND OF THE INVENTION

1. Field of the Invention

The instant disclosure pertains to thermostable DNA polymerases which exhibit improved robustness and efficiency.

2. Background

DNA polymerases are enzymes which are useful in many recombinant DNA techniques such as nucleic acid amplification by the polymerase chain reaction ("PCR"), self-sustained sequence replication ("3SR"), and high temperature DNA sequencing. Thermostable polymerases are particularly useful. Because heat does not destroy the polymerase activity, there is no need to add additional polymerase after every denaturation step.

However, many thermostable polymerases have been found to display a 5' to 3' exonuclease or structure-dependent single-stranded endonuclease ("SDSSE") activity which may limit the amount of product produced or contribute to the plateau phenomenon in the normally exponential accumulation of product. Such 5' to 3' nuclease activity may contribute to an impaired ability to efficiently generate long PCR products greater than or equal to 10 kb, particularly for G+C rich targets. In DNA sequencing applications and cycle sequencing applications, the presence of 5' to 3' nuclease activity may contribute to a reduction in desired band intensities and/or generation of spurious or background bands.

Additionally, many of the enzymes presently available are sensitive to high salt environments and have low processing ability, that is, the number of nucleotides incorporated per DNA polymerase binding event. Furthermore, addition of dITP to the reaction mixture to address compression problems usually results in reduced activity of the enzyme.

Thus, a need continues to exist for an improved DNA polymerase having increased tolerance to high salt conditions, efficient utilization of dITP, high productivity, and improved performance on GC-rich templates.

BRIEF SUMMARY OF THE INVENTION

The instant disclosure teaches a purified recombinant thermostable DNA polymerase comprising the amino acid sequence set forth in FIG. 1, as well as a purified recombinant thermostable DNA polymerase which exhibits at least about 80% activity at salt concentrations of 50 mM and greater. The instant disclosure further teaches a purified recombinant thermostable DNA polymerase which exhibits at least about 70% activity at salt concentrations of 25 mM and greater, and a purified recombinant thermostable DNA polymerase having a processivity of about 30 nucleotides per binding event.

The instant disclosure also teaches an isolated nucleic acid that encodes a thermostable DNA polymerase, wherein said nucleic acid consists of the nucleotide sequence set forth in FIG. 1, as well as a recombinant DNA vector that comprises the nucleic acid, and a recombinant host cell transformed with the vector.

The instant disclosure also teaches a method of sequencing DNA comprising the step of generating chain terminated fragments from the DNA template to be sequenced with the DNA polymerase in the presence of at least one chain terminating agent and one or more nucleotide triphosphates, and determining the sequence of said DNA from the sizes of said fragments. The instant disclosure also teaches a kit for sequencing DNA comprising the DNA polymerase.

BRIEF DESCRIPTION OF THE SEVERAL VIEWS OF THE DRAWINGS

FIG. 1 depicts the amino acid sequence (SEQ ID No. 2) (and DNA sequence encoding therefor (SEQ ID No. 1)) for the FY7 polymerase.

FIG. 16 depicts the processivity measured for Thermo Sequenase DNA polymerase, AmpliTaq FS DNA polymerase, compared with the processivity measured for FY7 DNA polymerase.

DETAILED DESCRIPTION OF THE INVENTION

Figure 2A:
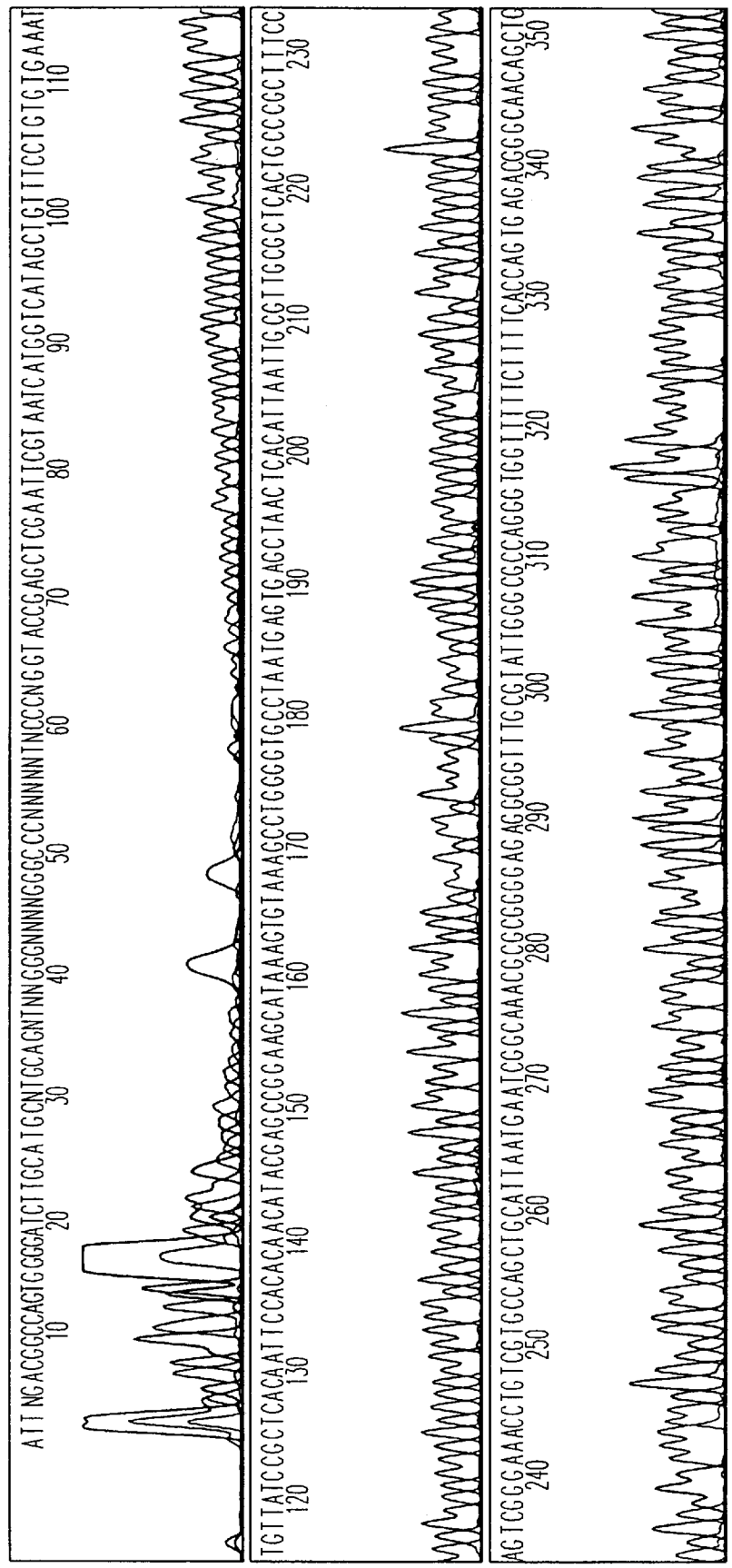
FIG. 2 depicts the DNA sequence (SEQ ID No. 3) of M13mp18 DNA sequenced using the FY7 polymerase formulated in Mn conditions, as shown by a print out from an ABI model 377 automated fluorescent DNA sequencing apparatus.

A series of polymerase mutants were constructed with the aim of obtaining an improved polymerase for DNA sequencing, by reducing the exonuclease activity found in full length *Thermus thermophilus* and *Thermus aquaticus* DNA polymerase I enzymes. Six conserved motifs (Gutman and Minton (1993) Nucleic Acids Research 21, 4406–4407) can be identified in the amino-terminal domain of pol I type polymerases, in which the 5' to 3' exonuclease activity has been shown to reside. Further, six carboxylate residues in these conserved regions have been shown in a crystal structure to be located at the active site of the exonuclease domain of *Thermus aquaticus* DNA pol I (Kim et al., (1995) Nature 376, 612–616). Point mutations were made by site-directed mutagenesis to carboxylates and other residues in three of six conserved motifs in Tth and Taq polymerases as follows: Taq D18A, Taq T140V, Taq D142N/D144N. All of these have the mutation F667Y outside of the exonuclease domain. Tth D18A, Tth T141V, Tth D143N/D145N. All of these have the mutation F669Y outside of the exonuclease domain.

All polymerases were evaluated for exonuclease activity, processivity, strand displacement, salt tolerance, thermostability, and sequencing quality. One FY7 polymerase, Tth D18A, F669Y, is described in further detail below.

EXAMPLES

Methods

In Vitro Mutagenesis

PCR was employed to introduce an aspartic acid to alanine amino acid change at codon 18 (D18A) of cloned full length F669Y Tth (plasmid pMR10). Mutagenic Primer 1 (CTGTTCGAACCCAAAGGCCGTGTCCTCCTGGT GGCCGGCCACCAC) (SEQ ID No. 25) spans nucleotides 19–60 of pMR10 including codon 18 and a BstBI restriction site. Oligonucleotide Primer 2 (GAGGCTGCCGAATTCCAGCCTCTC) (SEQ ID No. 26) spans an EcoRI site of pMR10. pMR10 was used as template DNA. The PCR product was digested with BstBI and EcoRI and ligated to two fragments of pMR10: a 5000 bp KpnI/BstBI and a 2057 bp EcoRI/KpnI, creating plasmid pMR12. Cells of *E. coli* strain DH1λ$^+$ were used for primary transformation, and strain M5248 (λ cI857) was used for protein expression, although any comparable pair of *E. coli* strains carrying the cI$^+$ and cI857 alleles could be utilized. Alternatively, any rec$^+$ cI$^+$ strain could be induced by chemical agents such as nalidixic acid to produce the polymerase.

Purification of Polymerase

M5248 containing plasmid pMR12 was grown in one liter of LB medium (1% tryptone, 0.5% yeast extract, 1% NaCl), preferably 2× LB medium, containing 100 mg/ml ampicillin at 30° C. When the OD$_{600}$ reached 1.0, the culture was induced at 42° C. for 1.5 hours. The cultures were then cooled to <20° C. and the cells harvested by centrifugation in a Sorvall RC-3B centrifuge at 5000 rpm at 4° C. for 15 to 30 minutes. Harvested cells were stored at –80° C.

The cell pellet was resuspended in 25 ml pre-warmed lysis buffer (50 mM Tris-HCl pH 8.0, 10 mM MgCl$_2$, 16 mM (NH$_4$)$_2$SO$_4$, 1 mM EDTA, 0.1%, preferably 0.2% Tween 20, 0.1%, preferably 0.2% NP40). Preferably, the lysis buffer contains 300 mM NaCl. Resuspended cells were incubated at 75–85° C. for 10–20 minutes, sonicated for 1 minute, and cleared by centrifugation. The cleared lysate was passed through a 300 ml column of diethylaminoethyl cellulose (Whatman DE 52) equilibrated in buffer A (50 mM Tris-HCl pH 8.0, 1 mM EDTA, 0.1% Tween 20, 0.1% NP40) containing 100 mM, preferably 300 mM NaCl. Fractions were assayed for polymerase activity, and those demonstrating peak polymerase activity were pooled, diluted to 50 mM NaCl with Buffer A, and loaded onto a heparin sepharose column (20 ml) equilibrated with 50 mM NaCl in buffer A. The polymerase was eluted from the column with a linear salt gradient from 50 mM to 700 mM NaCl in buffer A. Fractions were assayed for polymerase activity, and those demonstrating peak activity were pooled and dialyzed against final buffer (20 mM Tris-HCl pH8.5, 50% (v/v) glycerol, 0.1 mM EDTA, 0.5% Tween 20, 0.5% NP40, 1 mM DTT, 100 mM KCl). The purified protein is designated FY7. The amino acid sequence (and DNA sequence encoding therefor) are presented in FIG. 1. ps Bacterial Strains

*E. coli* strains: DH1λ$^+$ [gyrA96, recA1, relA1, endA1, thi-1, hsdR17, supE44, λ$^+$]; M5248 [λ(bio275, cI857, cIII+, N+, λ(H1))].

PCR

Plasmid DNA from *E. coli* DH1λ$^+$ (pMR10) was prepared by SDS alkaline lysis method (Sambrook et al., Molecular Cloning 2$^{nd}$ Ed. Cold Spring Harbor Press, 1989). Reaction conditions were as follows: 10 mM Tris-HCl pH 8.3, 50 mM KCl, 1.5 mM MgCl$_2$, 0.001% gelatin, 1 uM each primer, 2.5U Taq polymerase, per 100 µl reaction. Cycling conditions were 94° C. 2 minutes, then 35 cycles of 94° C. 30s, 55° C. 30s, 72° C. 3 minutes followed by 72° C. for 7 minutes.

Example 1

Formulation of the Enzyme in Mn Conditions

In the following "pre-mix" protocol, all the reagents are contained in two solutions; reagent mix A and reagent mix B.

Reagent Mix A

The following reagents were combined to make 10 ml of reagent mix A:

2.5 ml 1 M HEPPS N-(2-hydroxyethyl) piperazine-N'-(3-propanesulfonic acid), pH 8.0

500 µl 1 M tartaric acid, pH 8.0

50,000 units FY7 DNA polymerase 1 unit *Thermoplasma acidophilum* inorganic pyrophosphatase 100 µl 100 mM dATP 100 µl 100 mM dTTP 100 µl 100 mM dCTP 500 µl 100 mM dITP 9.375 µl 100 µM C-7-propargylamino-4-rhodamine-6-G-ddATP 90 µl 100 µM C-5-propargylamino-4-rhodamine-X-ddCTP 6.75 µl 100 µM C-7-propargylamino-4-rhodamine-110-ddGTP 165 µl 100 µM C-5-propargylamino-4-tetramethylrhodamine-ddUTP 10 µl 50 mM EDTA 1 ml glycerol The volume was made up to 10,000 μl with deionized H₂O.

Reagent Mix B

The following reagents were combined to make 10 ml of reagent mix B:

10 μl 1M MES 2-(N-morpholino)ethanesulfonic acid, pH 6.0

200 μl 1M MgCl₂

75 μl 1M MnSO₄

The volume was made up to 10,000 μl with deionized H₂O.

Example 2

Use of the Formulation From Example 1

Figure 2B:
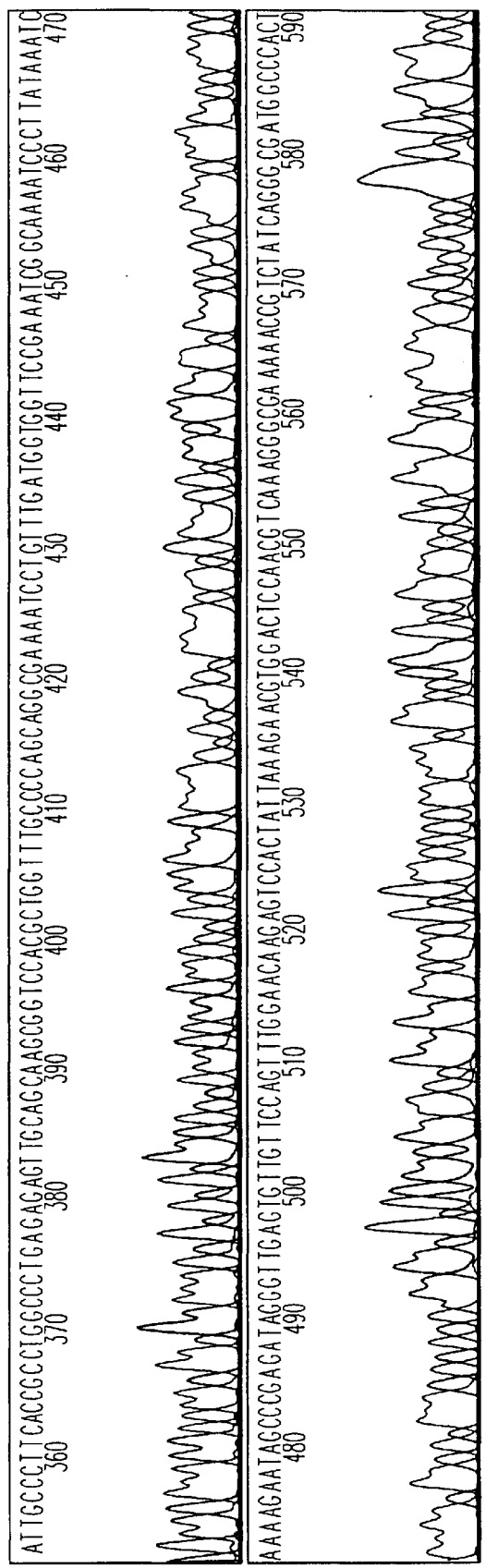

Two (2) μl reagent mix A, 2 μl reagent mix B, 200 ng M13mp18 DNA, 5 pmole of primer (M13–40 Forward 5'-GTTTTCCCAGTCACGACGTTGTA) (SEQ ID No. 27), and deionized water to a total volume of 20 μl were mixed together and subjected to 25 cycles of (95° C. 30 seconds, 60° C. 1 minute) in a thermal cycler. After cycling, 4 μl of a solution which contained 1.5 M sodium acetate, 250 mM EDTA was added. The solution was mixed and 4 volumes (100 μl) of ethanol added. The DNA was precipitated by incubation on ice for 15–20 minutes followed by centrifugation. The supernatant was removed and the pellet was washed with 70% ethanol, dried and resuspended in 4 μl of formamide containing loading dye. The resuspended DNA was then run on an automated fluorescent DNA sequencing apparatus (ABI model 377 instrument). The print out from the machine of the DNA sequence is shown as FIG. 2.

Example 3

Formulation of the Enzyme in Mg Conditions

In the following "pre-mix" protocol, all the reagents are contained in one solution.

Sequencing Premix

The following reagents were combined to make 800 μl of Sequencing premix 200 μl of 500 mM Tris-HCl pH 9.5, 20 mM MgCl₂

100 μl 40 units/μl FY7 DNA polymerase, 0.0008 units/μl *Thermoplasma acidophilum* inorganic pyrophosphatase 100 μl 10 mM dITP, 2 mM dATP, 2 mM dTTP, 2 mM dCTP 100 μl 0.125 μM C-7-propargylamino-4-rhodamine-6-G-ddATP 100 μl 1.2 μM C-5-propargylamino-4-rhodamine-X-ddCTP 100 μl 0.09 μM C-7-propargylamino-4-rhodamine-110-ddGTP 100 μl 2.2 μM C-5-propargylamino-4-tetramethylrhodamine-ddUTP Example 4

Use of the Formulation From Example 3

Figure 3A:
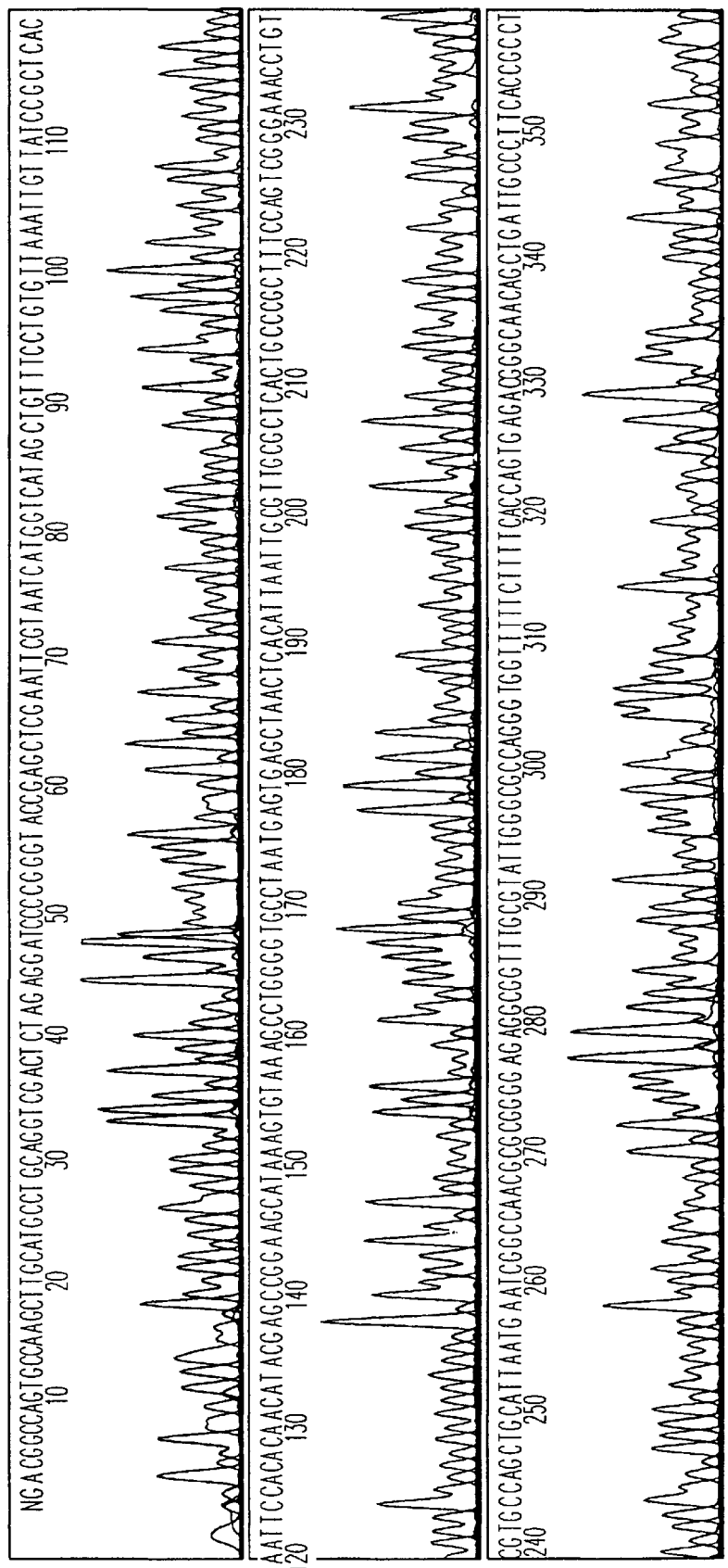
FIG. 3 depicts the DNA sequence (SEQ ID No. 4) of M13mp18 DNA sequenced using the FY7 polymerase formulated in Mg conditions, as shown by a print out from an ABI model 377 automated fluorescent DNA sequencing apparatus.
Figure 3B:
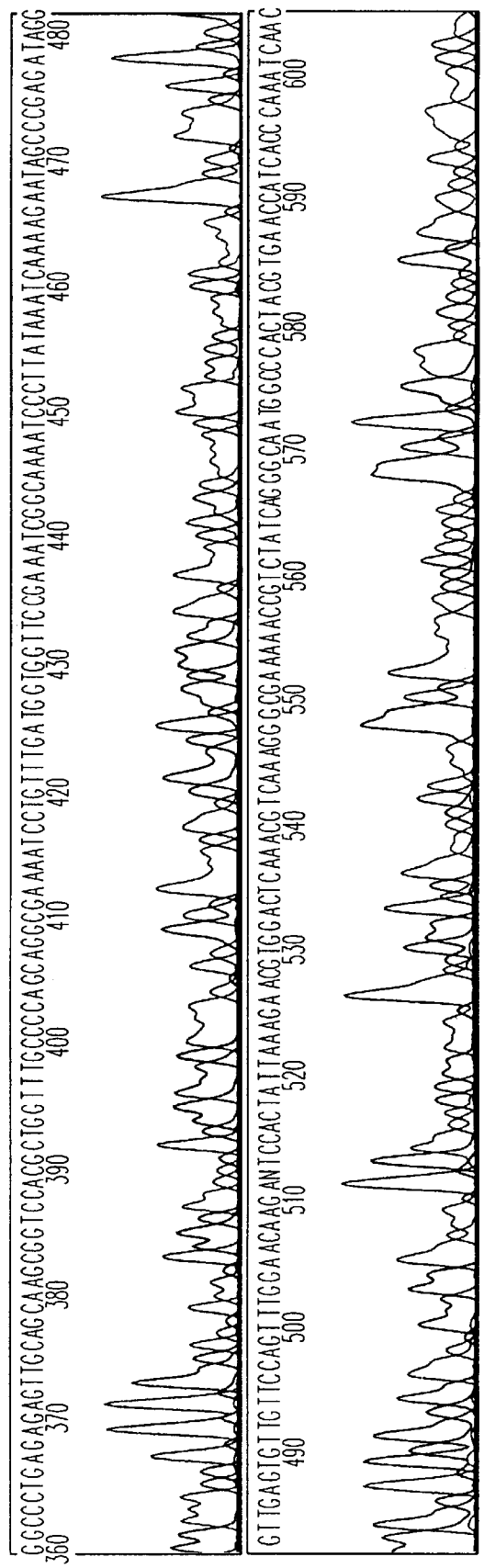

Four (4) μl of sequencing premix, 200 ng M13mp18 DNA, 5 pmole of primer (M13–40 Forward 5'-GTTTTCCCAGTCACGACGTTGTA) (SEQ ID No. 27), and deionized water to a total volume of 20 μl were mixed together and subjected to 25 cycles of (95° C. 30 seconds, 60° C. 2 minutes) in a thermal cycler. After cycling, 7 μl of 7.5 M ammonium acetate was added. The solution was mixed and 4 volumes (100 μl) of ethanol added. The DNA was precipitated by incubation on ice for 15–20 minutes followed by centrifugation. The supernatant was removed and the pellet was washed with 70% ethanol, dried and resuspended in 4 μl of formamide containing loading dye. The resuspended DNA was then run on an automated fluorescent DNA sequencing apparatus (ABI model 377 instrument). The print out from the machine of the DNA sequence is shown as FIG. 3.

Example 5

Figure 4:
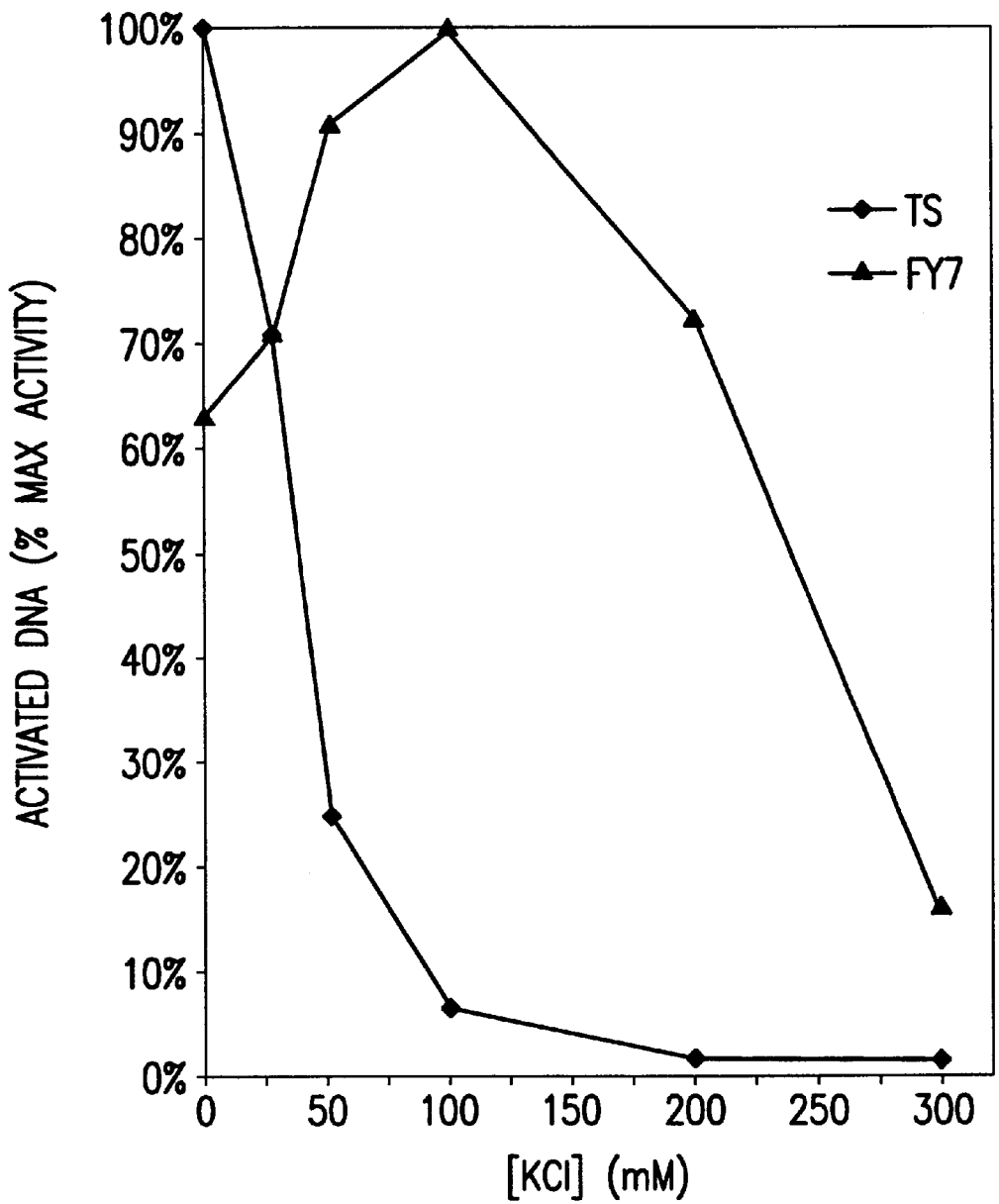
FIG. 4 depicts the percent of maximum polymerase activity for Thermo Sequenase™ enzyme DNA polymerase versus FY7 DNA polymerase under varying KCl concentrations.

Polymerase Activity Versus Salt Concentration (KCl) for Thermo Sequenase™ Enzyme and FY7 Enzyme The percent of maximum polymerase activity was measured for Thermo Sequenase™ enzyme DNA polymerase and FY7 DNA polymerase under varying KCl concentrations. The results are depicted in FIG. 4. The data indicate that FY7 has a much higher salt optimum as well as broader range of tolerance for salt in the reaction mixture than Thermo Sequenase™. The salt concentration which gives 50% activity is five-fold higher for FY7 than for Thermo Sequenase.

Figure 5:
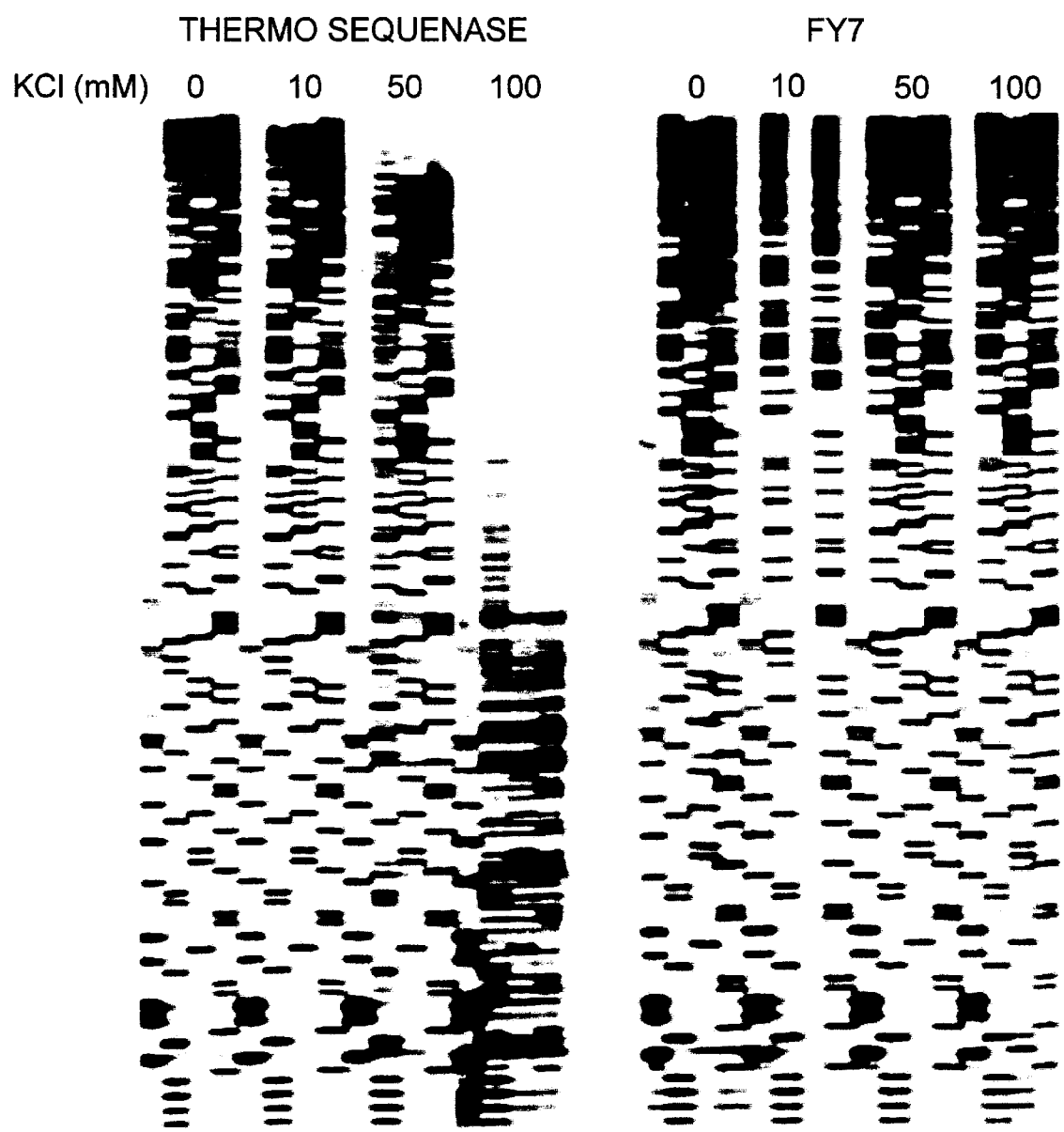
FIG. 5 depicts the effect of high salt concentrations on DNA sequencing ability in radioactively labeled DNA sequencing reactions using Thermo Sequenase™ enzyme DNA polymerase versus FY7 DNA polymerase.
Figure 6A:
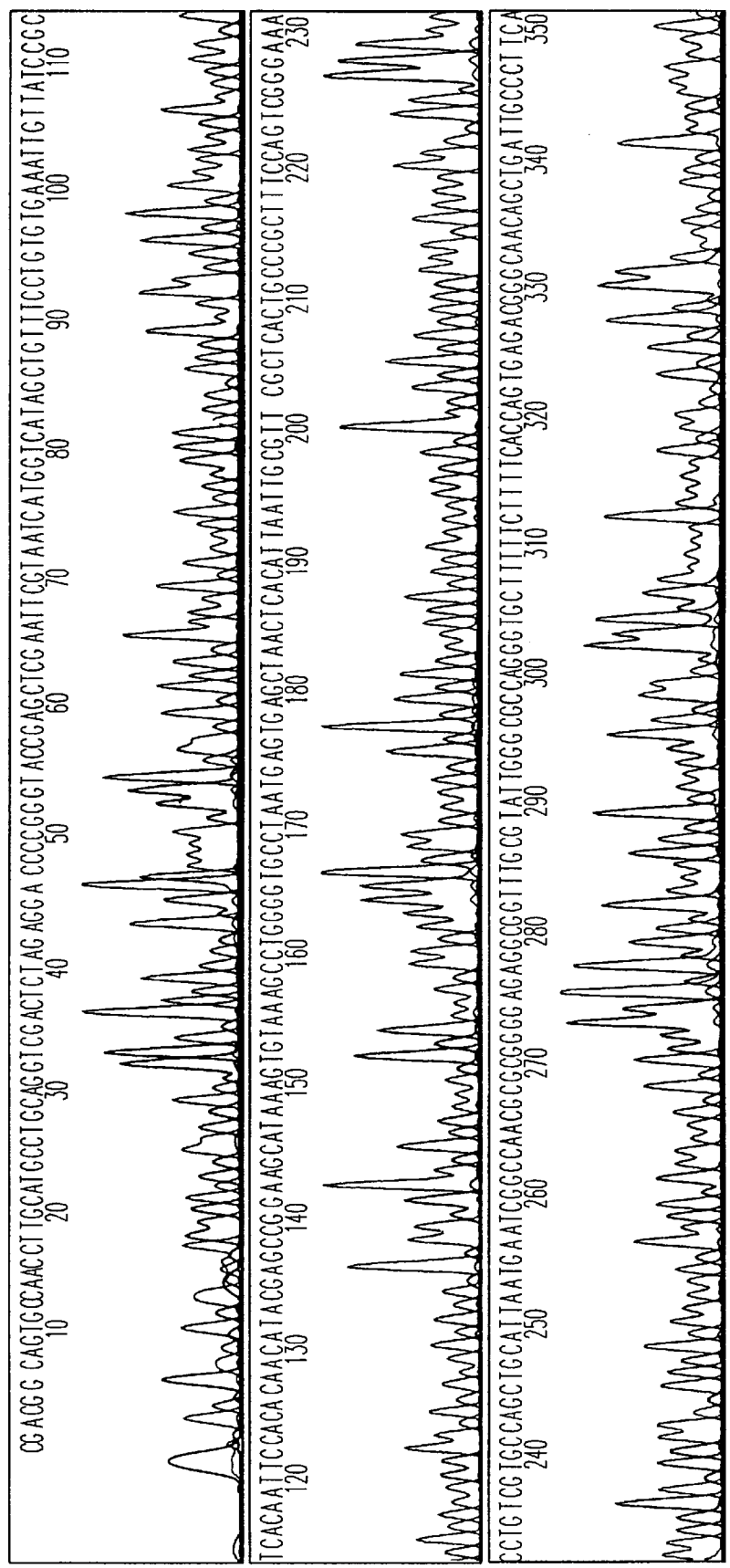
FIGS. 6–10 (SEQ ID Nos. 5–9, respectively) depict the effect of increasing salt concentration on the performance of Thermo Sequenase. At concentrations as low as 25 mM data quality is affected with the read length being decreased from at least 600 bases to about 450 bases. At 50 mM salt the read length is further decreased to about 350 bases, 75 mM to about 250 bases and at 100 mM the read length is negligible.
Figure 6B:
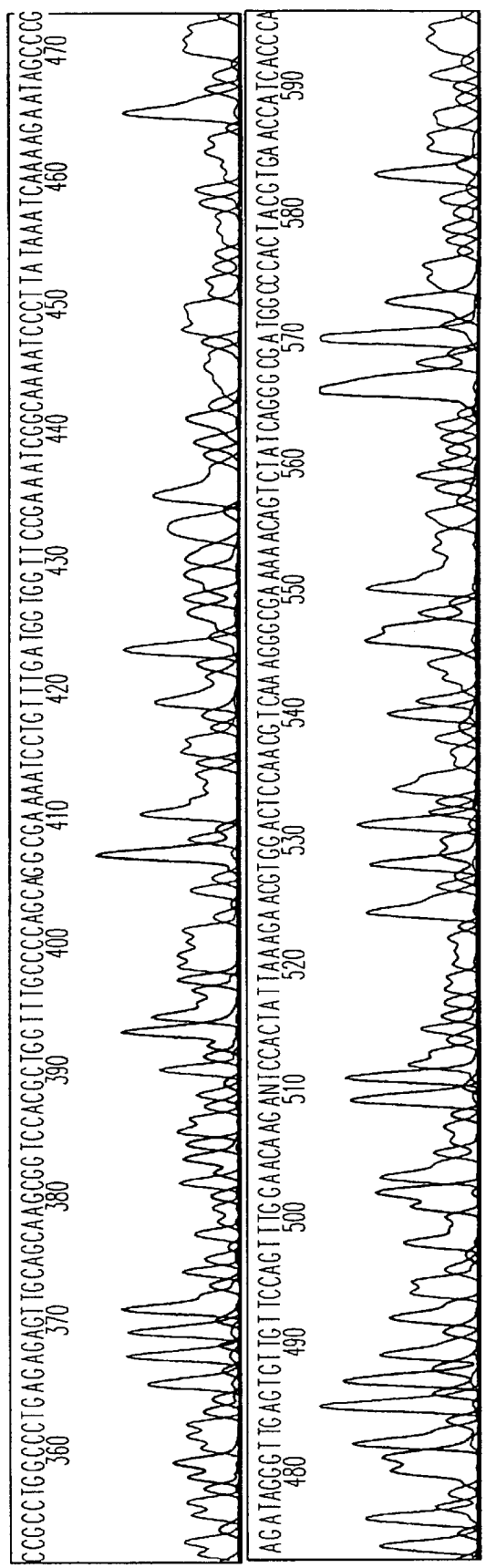
Figure 7A:
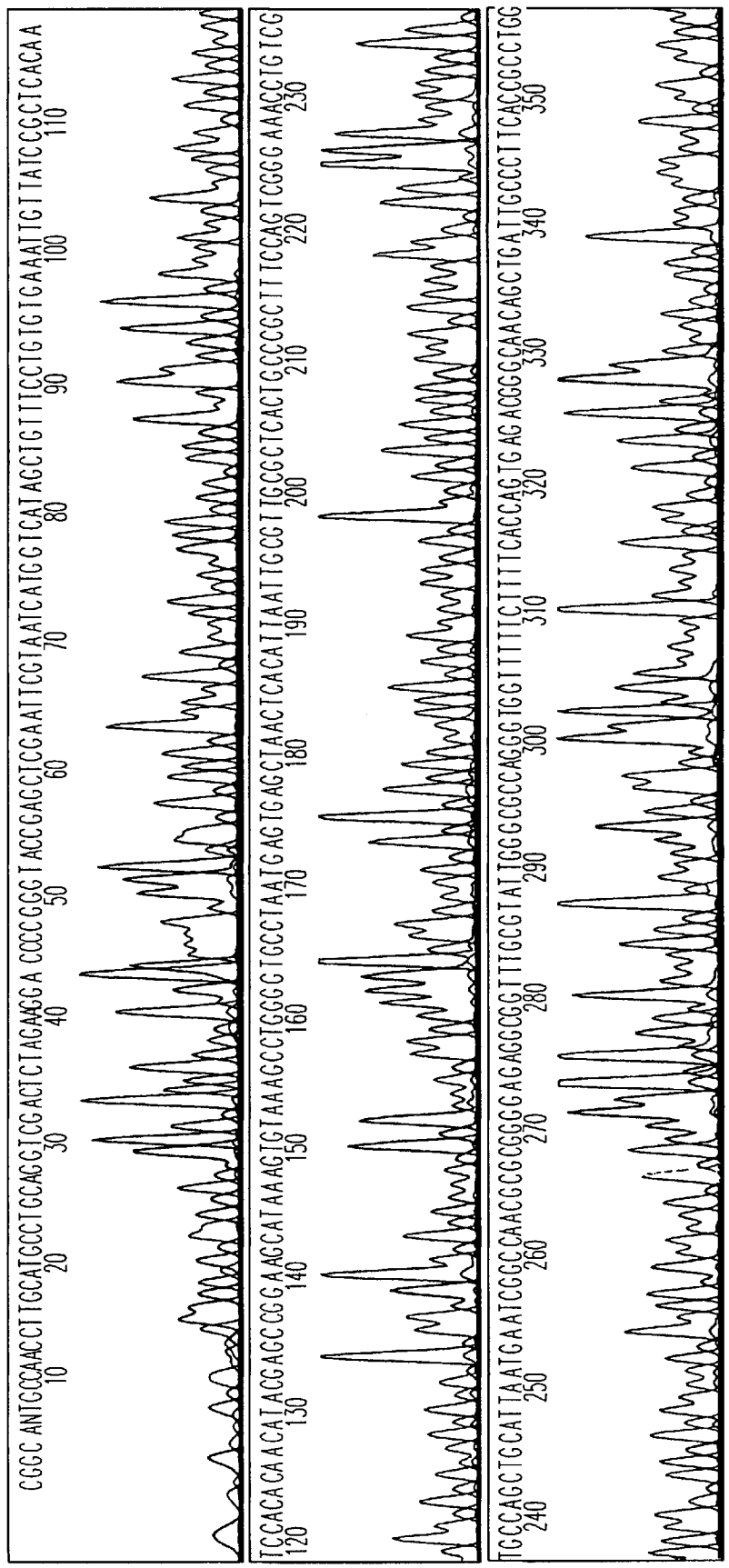
Figure 7B:
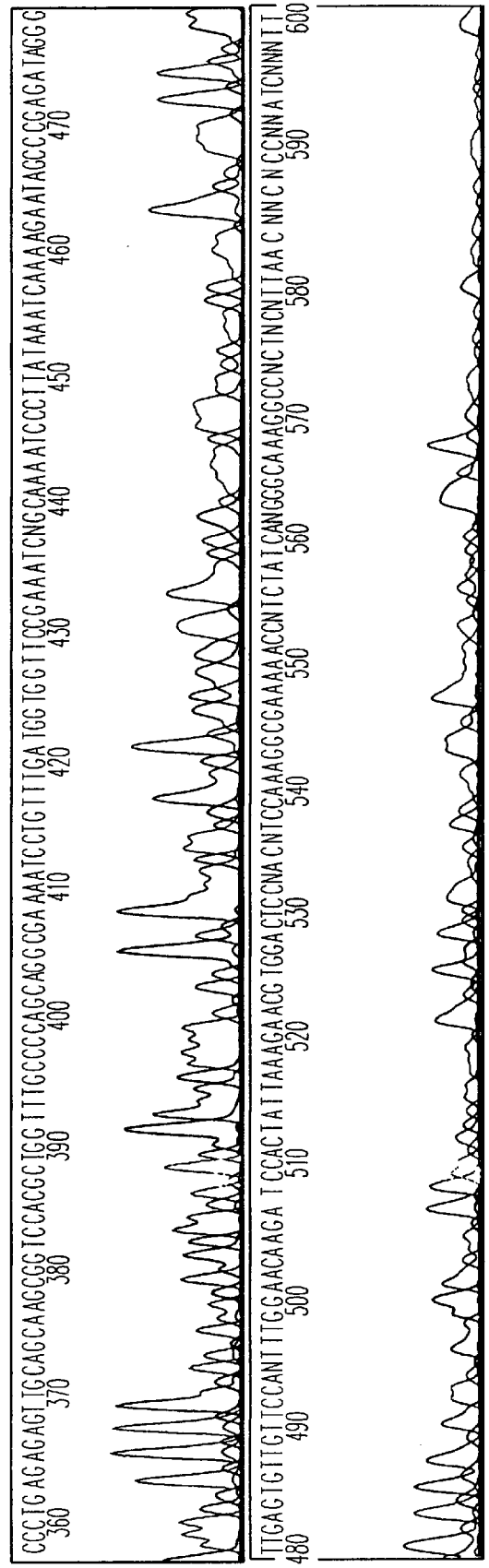
Figure 8A:
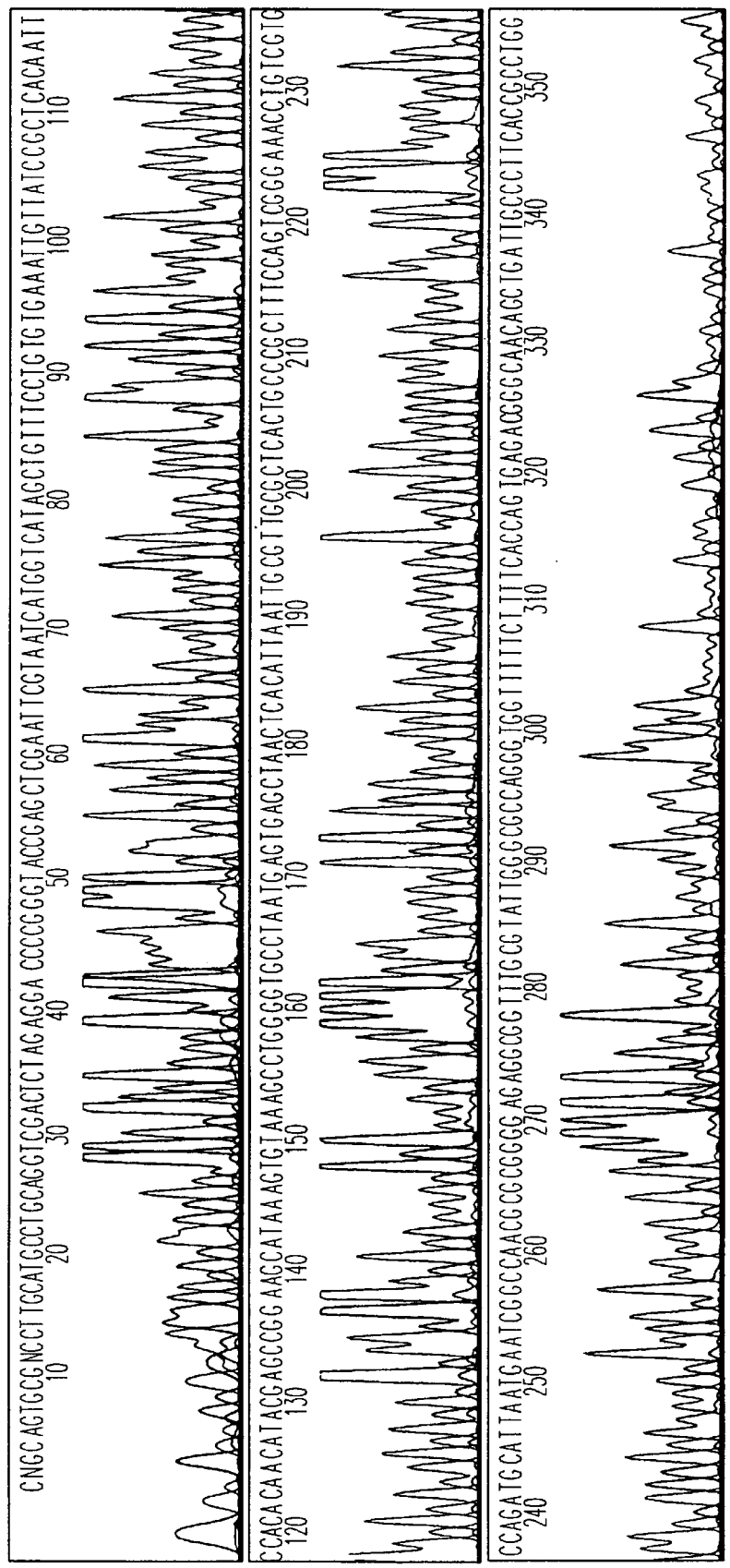
Figure 8B:
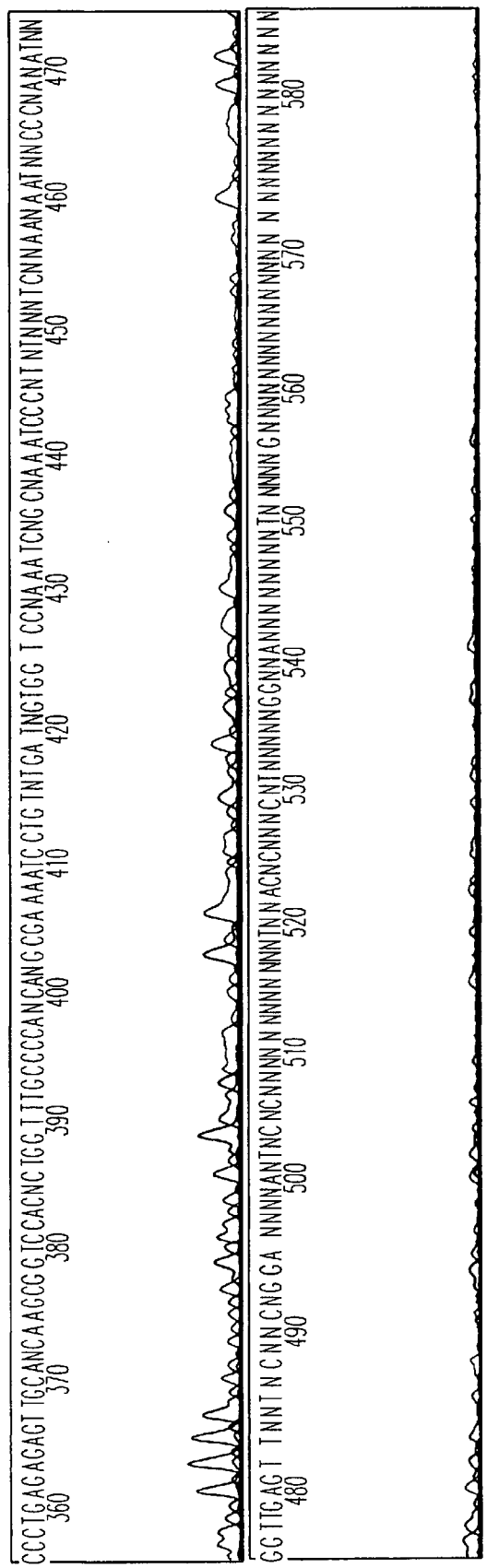
Figure 9A:
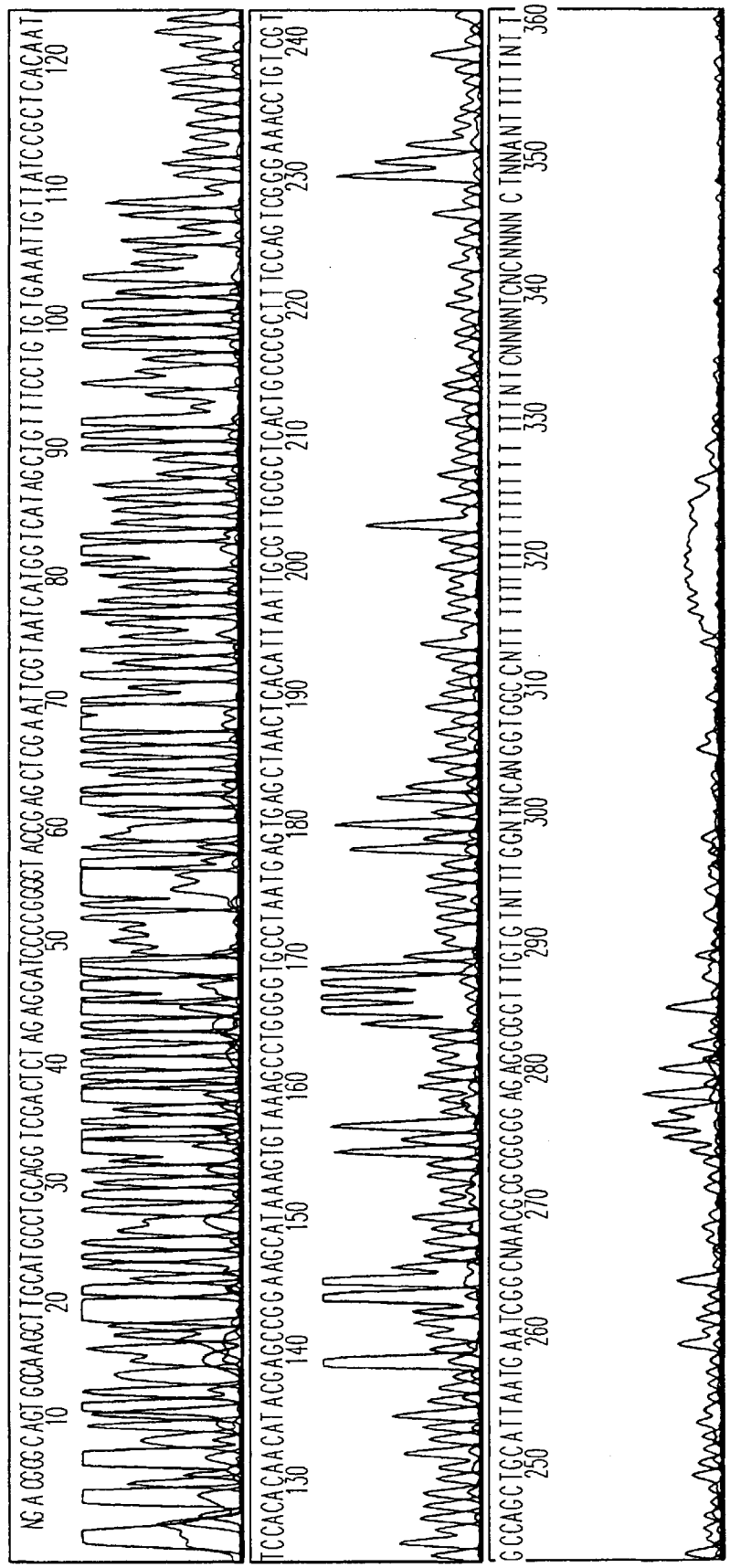
Figure 9B:
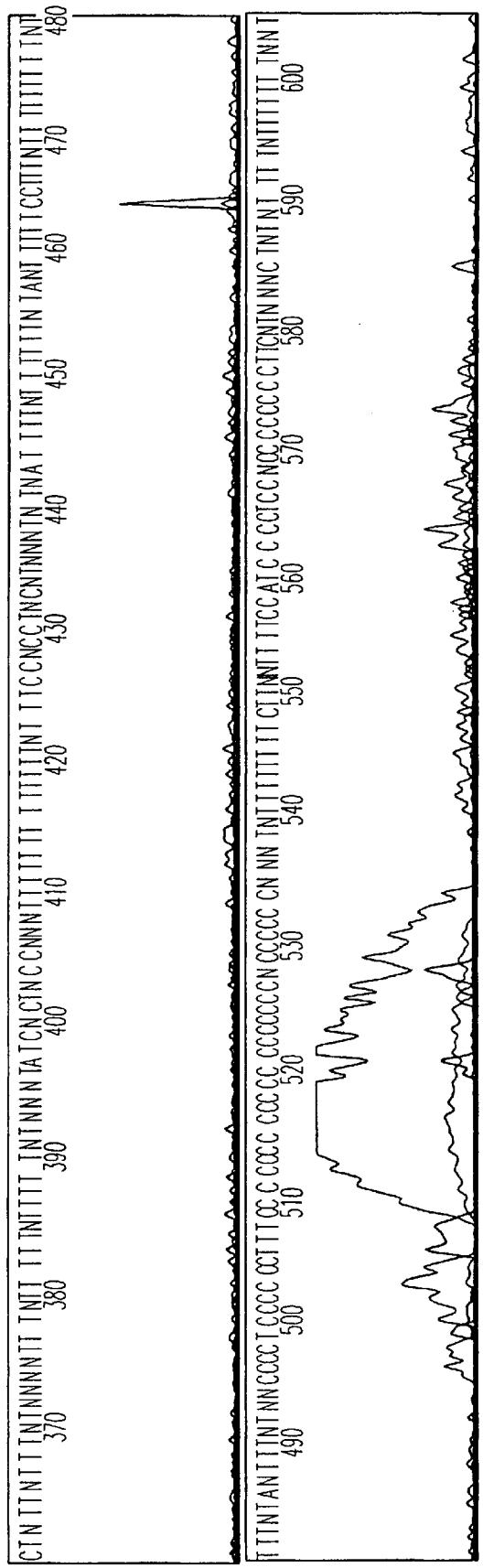
Figure 10A:
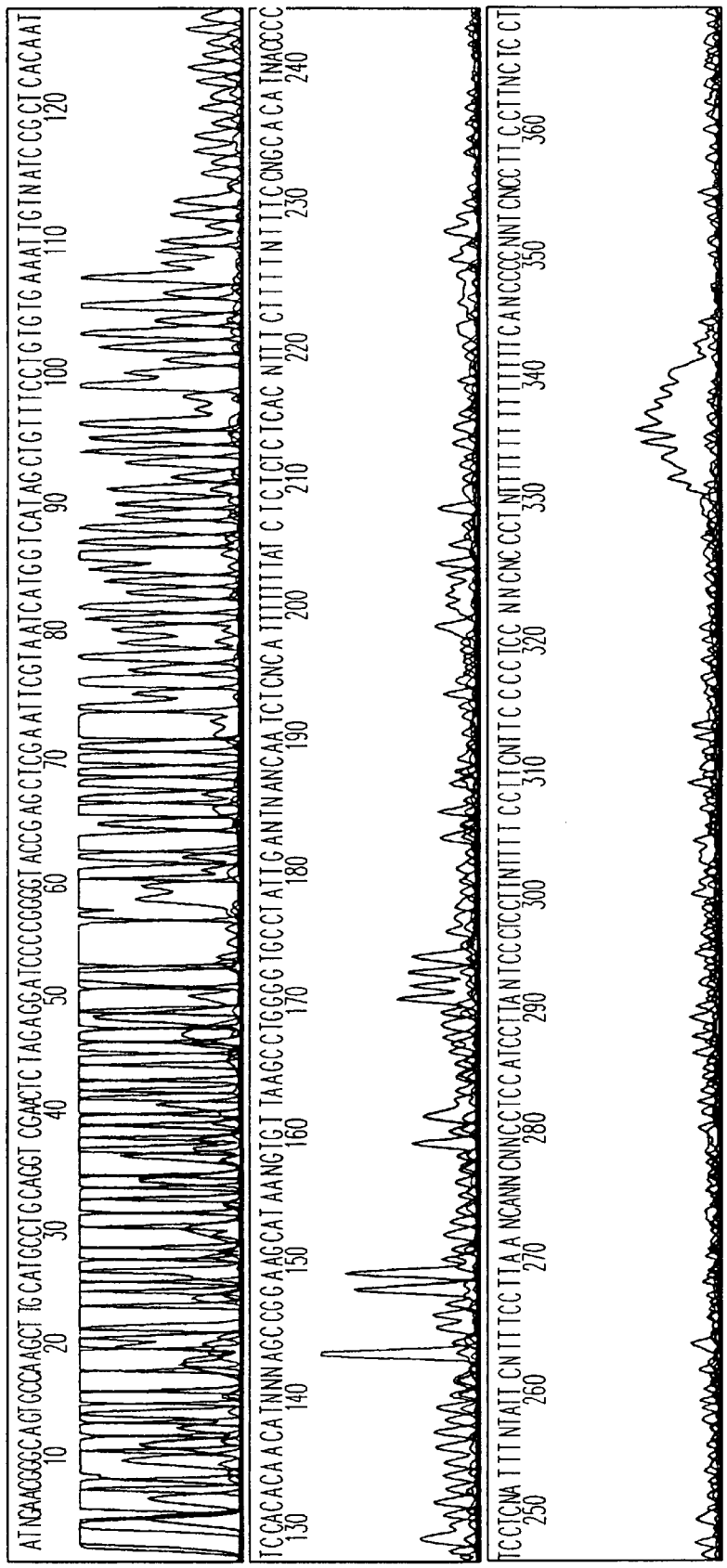
Figure 10B:
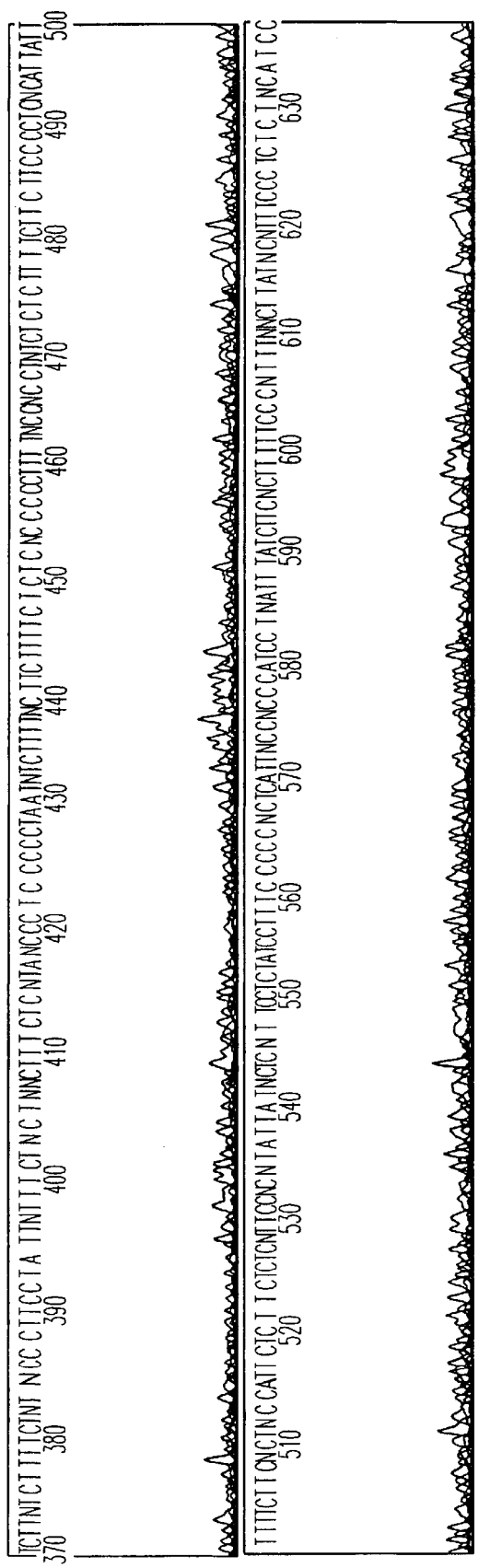
Figure 11A:
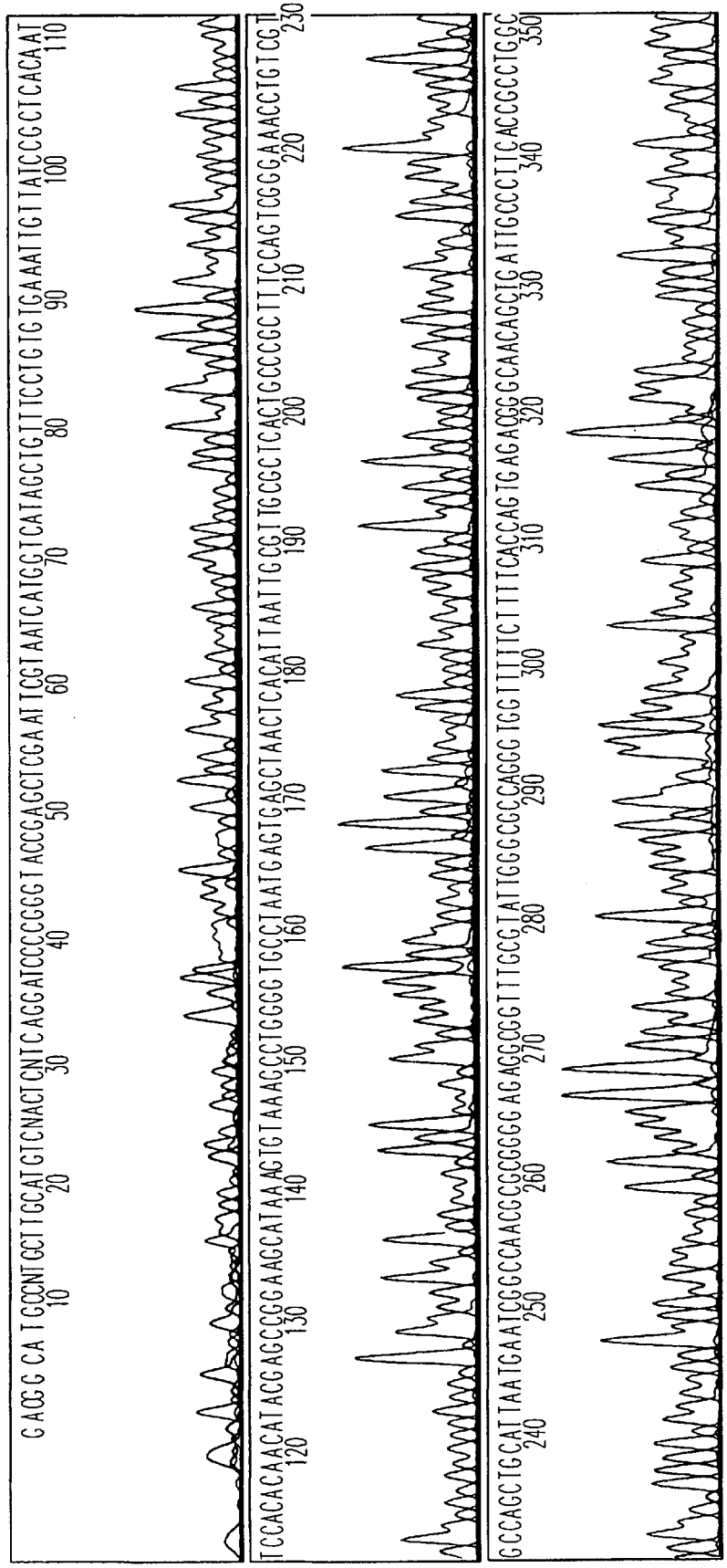
FIGS. 11–15 (SEQ ID Nos. 10–14, respectively) depict the effect of increasing salt concentration on the performance of FY7 DNA polymerase. There is no detrimental effect on performance to at least 75 mM KCl and only a slight decrease in data quality at 100 mM KCl.
Figure 11B:
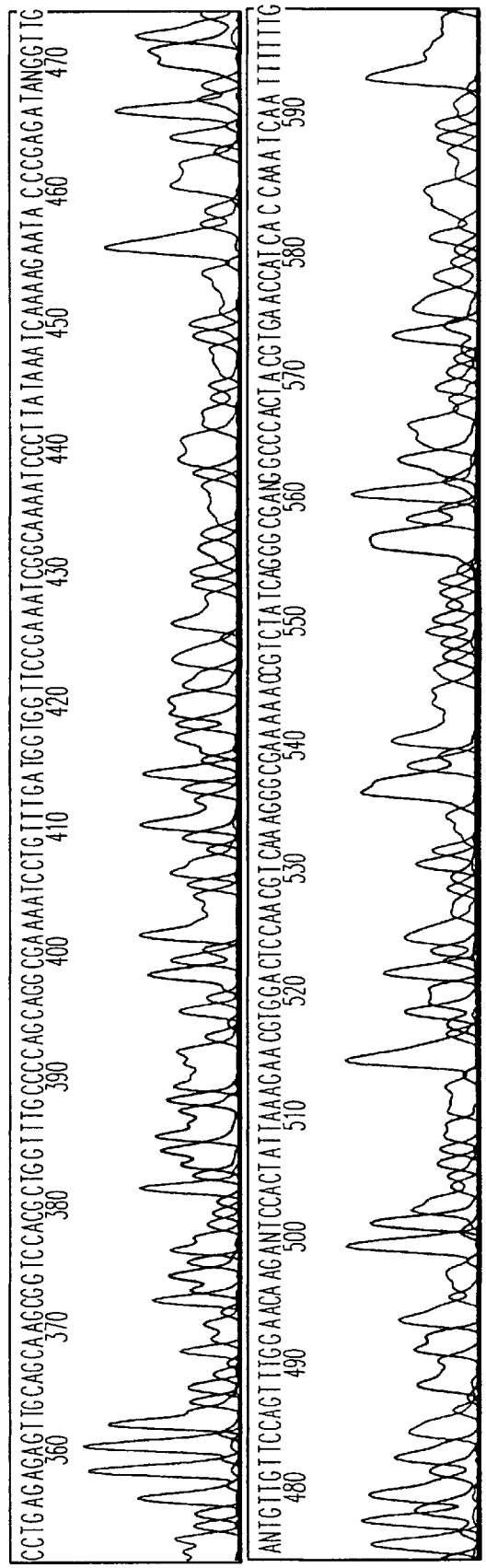
Figure 12A:
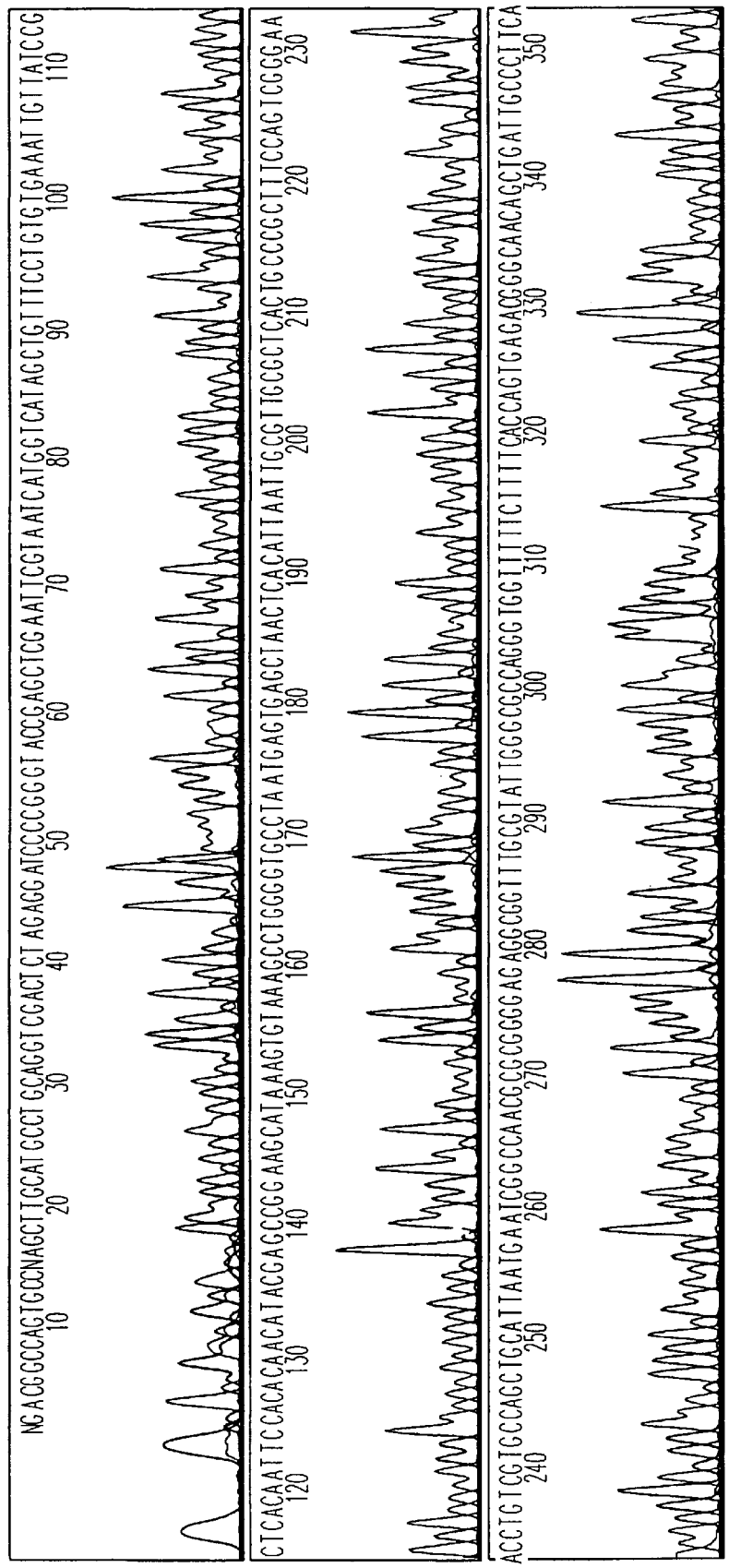
Figure 12B:
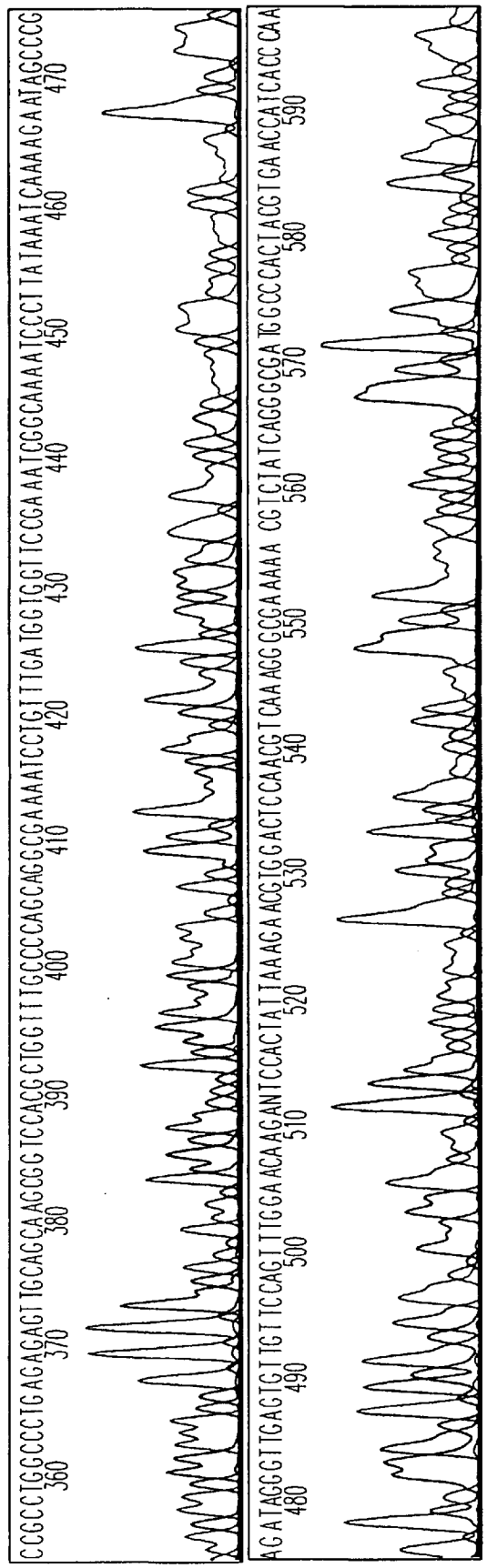
Figure 13A:
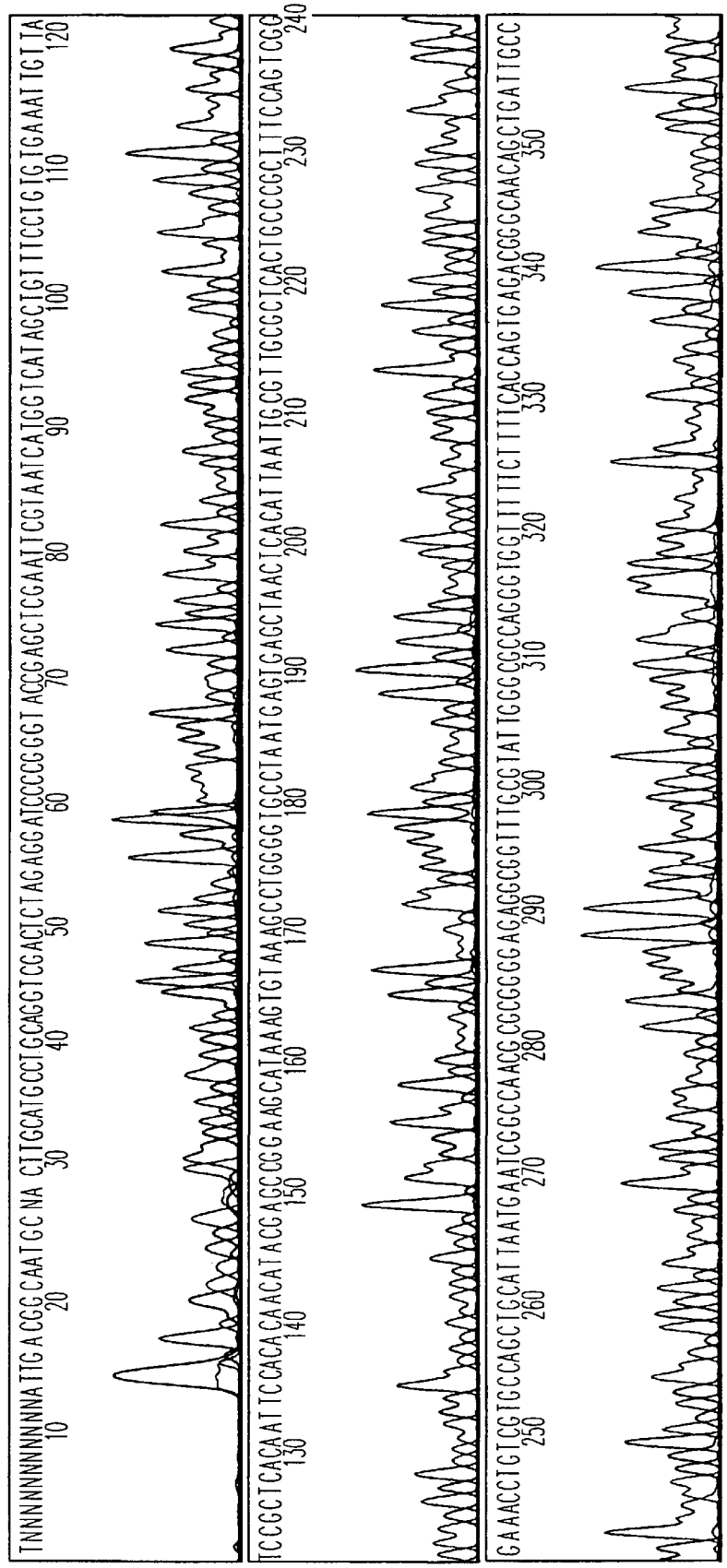
Figure 13B:
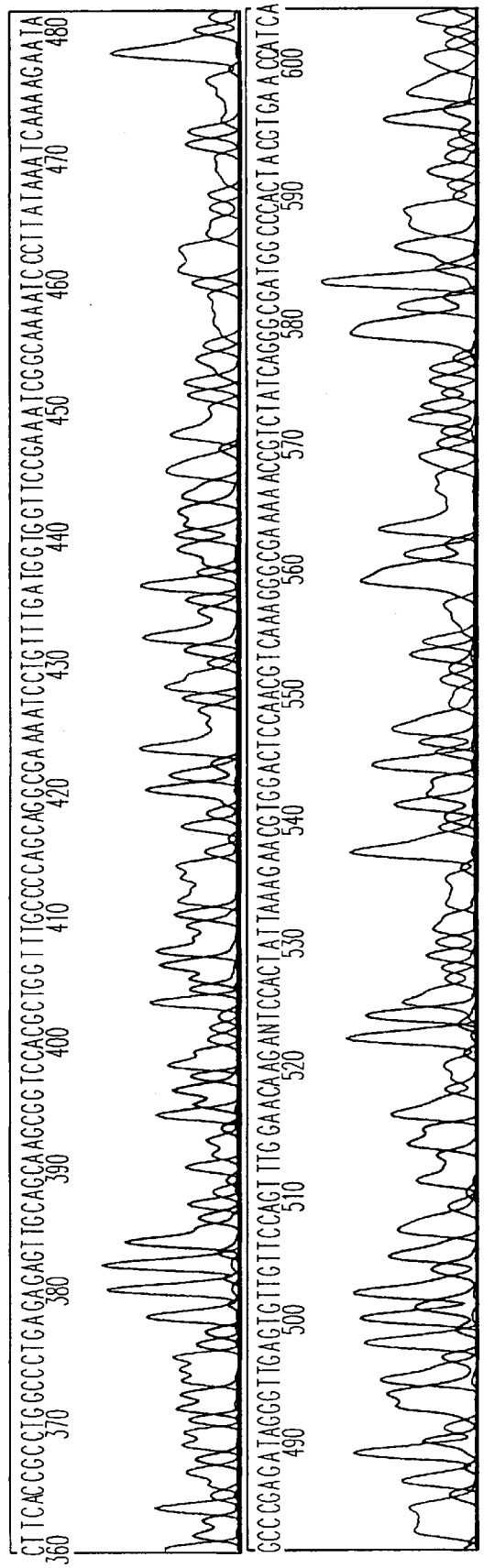
Figure 14A:
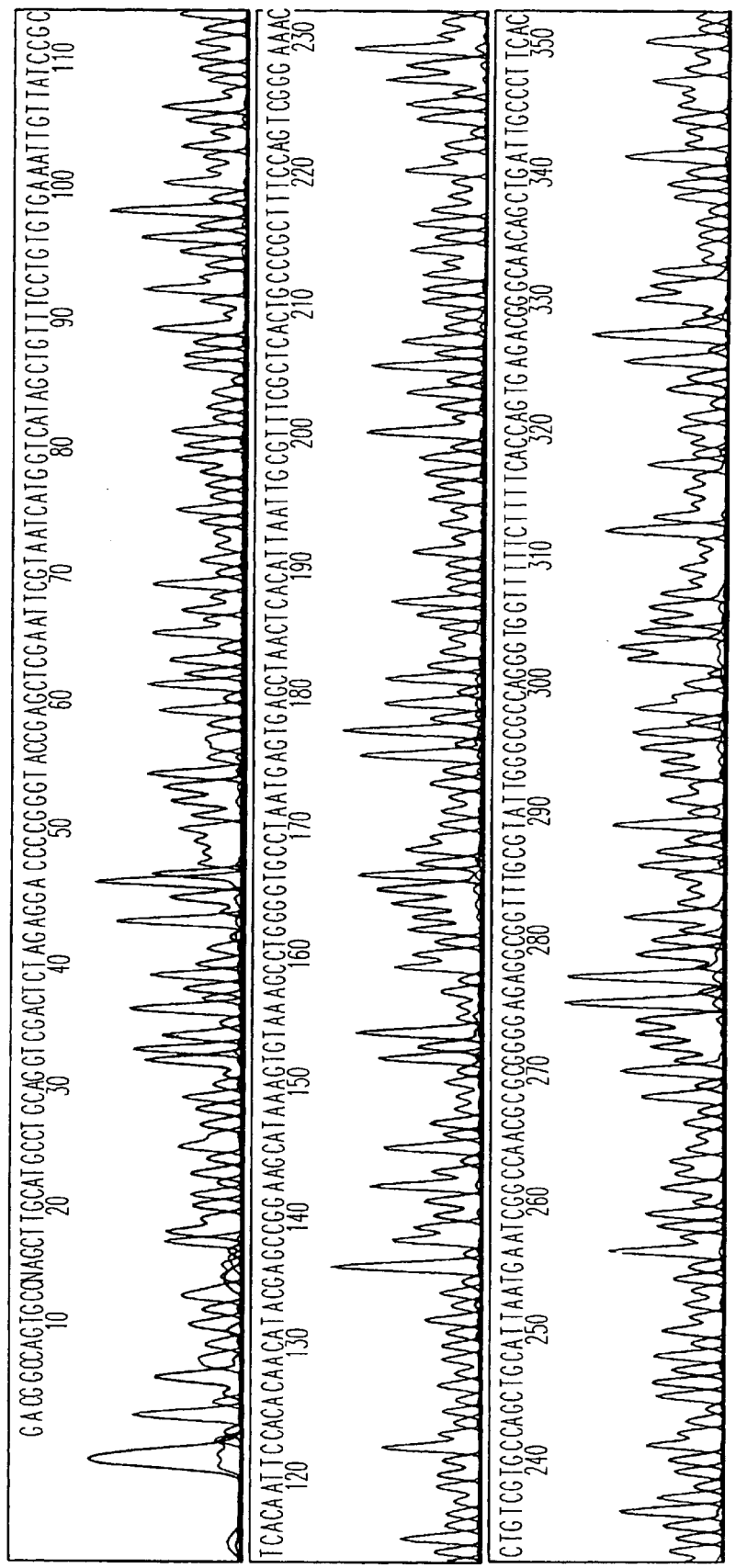
Figure 14B:
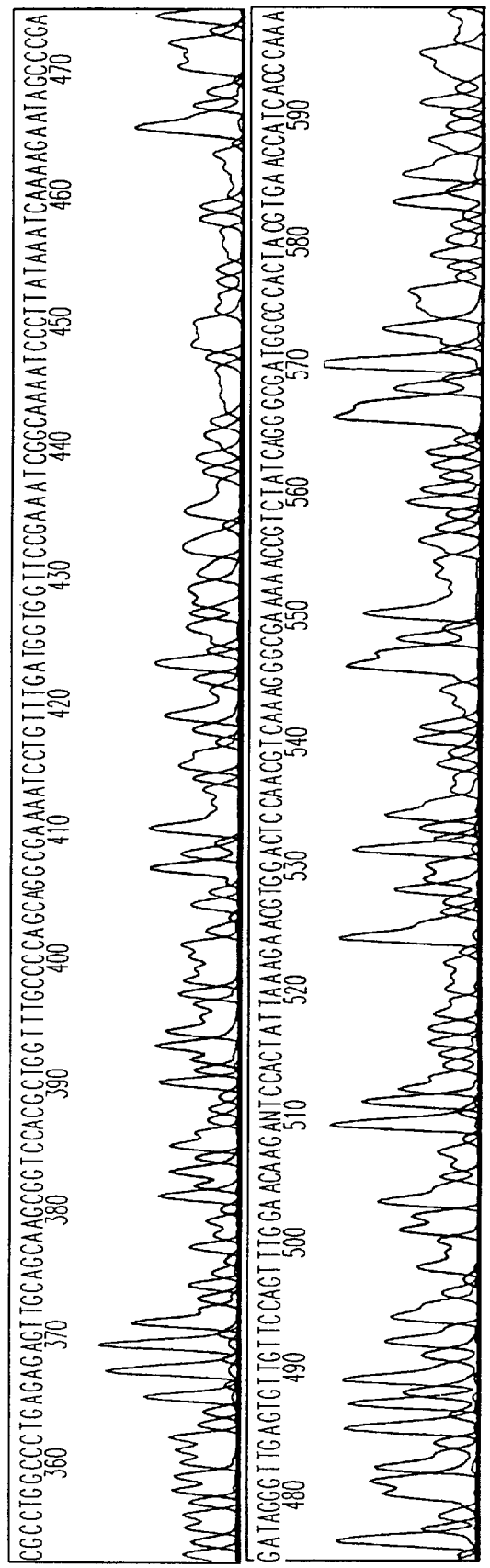
Figure 15A:
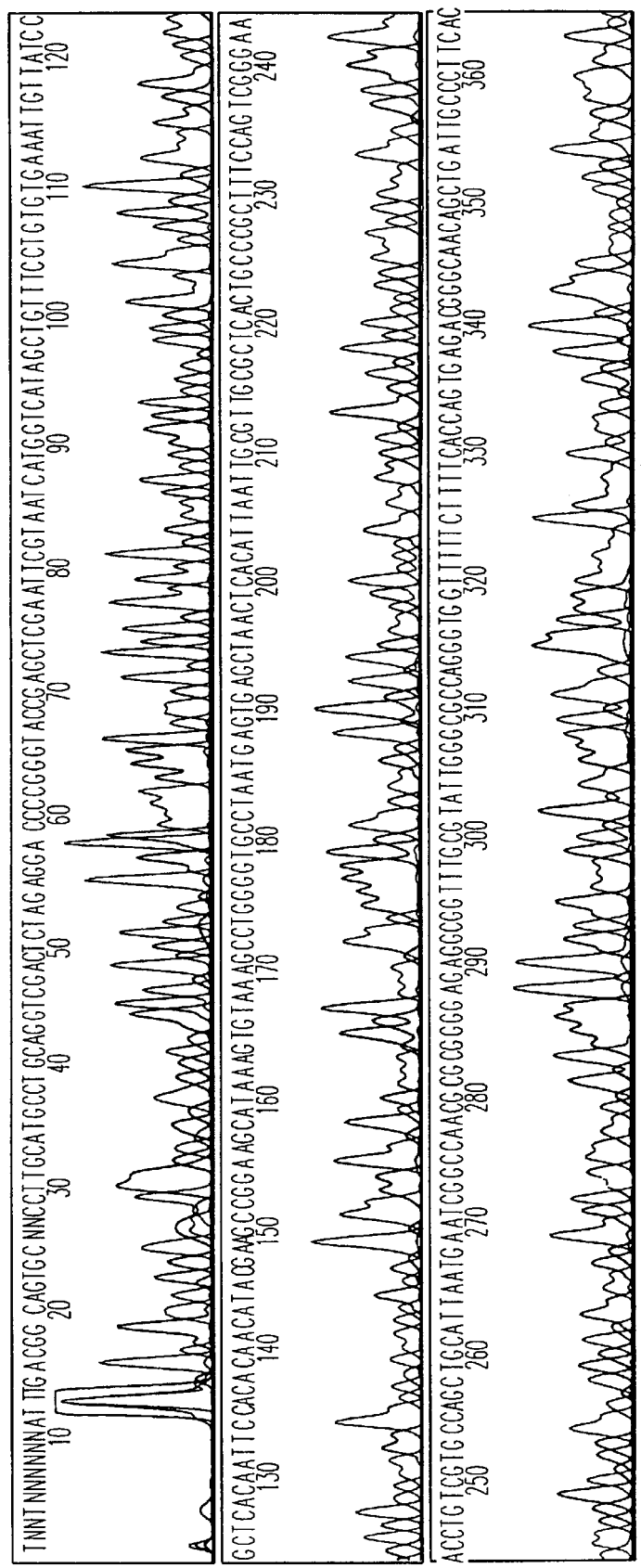
Figure 15B:
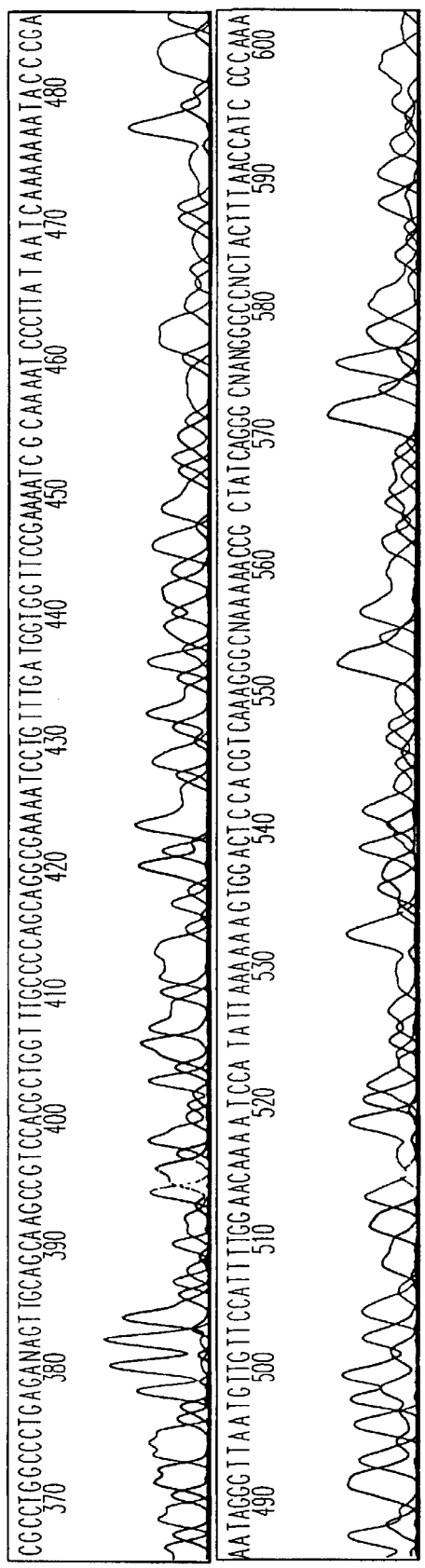

The effect of high salt concentrations on DNA sequencing ability in radioactively labeled DNA sequencing reactions was also examined. The results are presented in FIG. 5. At KCl concentrations of 50 mM or higher Thermo Sequenase™ polymerase performance degrades to levels at which usable data cannot be extracted. FY7 DNA polymerase, however, is able to give quite good sequencing data at concentrations of KCl of 100 mM.

Example 6

Fluorescent Sequencing Salt Tolerance

These experiments examined the effect of the above-demonstrated polymerase activity in high salt concentrations on DNA sequencing ability in fluorescently labeled terminator DNA sequencing reactions. The results are presented in FIGS. 6–15.

FIGS. 6–10 show the effect of increasing salt concentration on the performance of Thermo Sequenase. At concentrations as low as 25 mM data quality is affected with the read length being decreased from at least 600 bases to about 450 bases. At 50 mM salt the read length is further decreased to about 350 bases, 75 mM to about 250 bases and at 100 mM the read length is negligible.

FIGS. 11–15 show the effect of increasing salt concentration on the performance of FY7 DNA polymerase. There is no detrimental effect on performance to at least 75 mM KCl and only a slight decrease in data quality at 100 mM KCl.

As it is recognized that some types of DNA preparations may be contaminated with salt (which is detrimental to DNA sequencing data quality), the use of FY7 DNA polymerase allows for a more robust sequencing reaction over a broader range of template conditions.

Example 7

Polymerase Processivity

The processivity (number of nucleotides incorporated per DNA polymerase binding event) has been measured, for different DNA sequencing polymerases. The results are presented in FIG. 16. Thermo Sequenase DNA polymerase has a processivity of only ~4 nucleotides per binding event. AmpliTaq FS DNA polymerase has a processivity of ~15 nucleotides per binding event. FY7 DNA polymerase has a processivity more than seven-fold greater than Thermo Sequenase DNA polymerase and ~two-fold greater than AmpliTaq FS DNA polymerase at ~30 nucleotides per binding event.

Example 8

Polymerase Extension with dITP at 72° C.

Figure 17:
FIG. 17 depicts the improved read length obtained when using FY7 polymerase versus Thermo Sequenase DNA polymerase in radioactively labeled sequencing reactions incorporating the dGTP (Guanosine triphosphate) analog dITP (Inosine triphosphate) at 72° C.
Figure 18A:
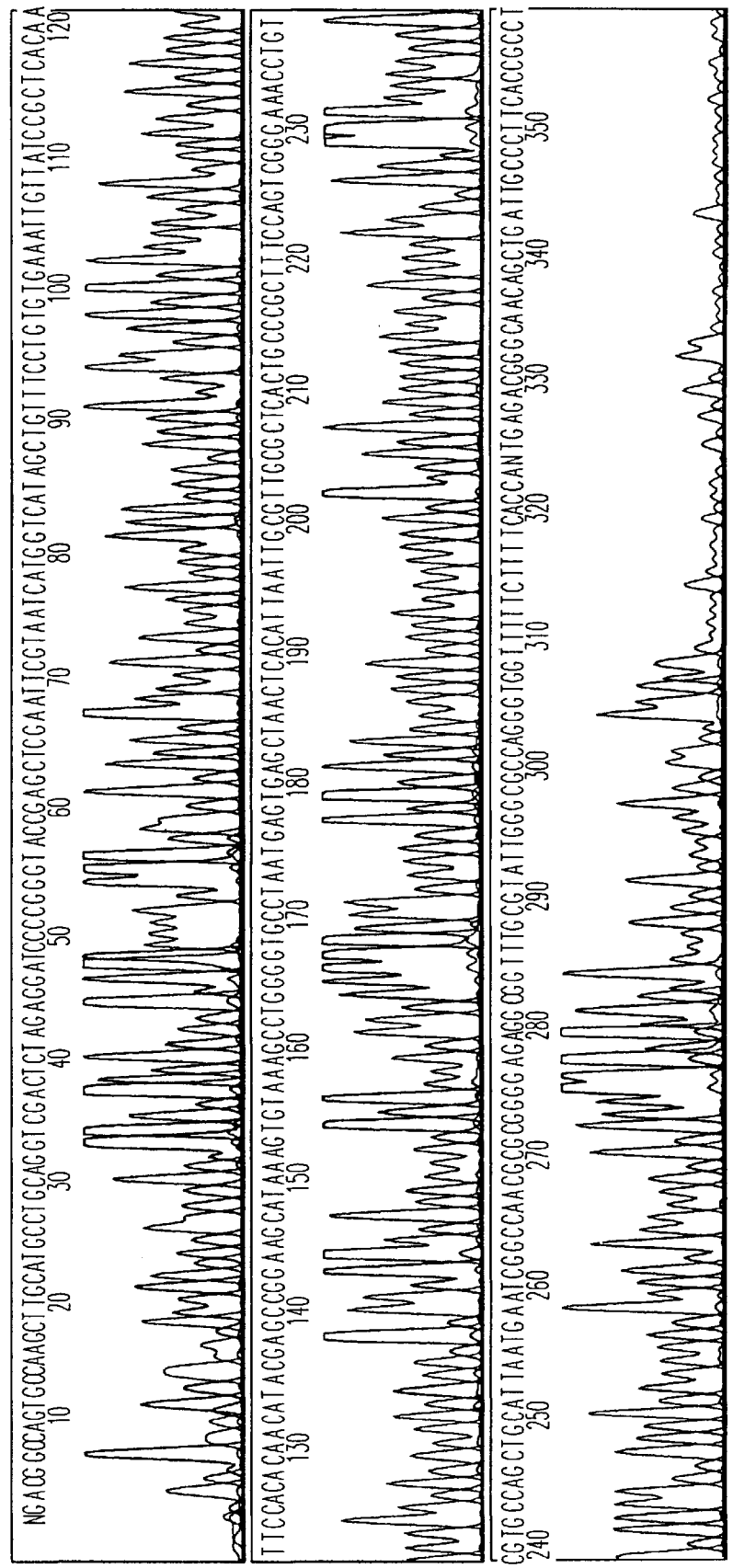
FIGS. 18–22 (SEQ ID Nos. 15–19, respectively) show the effect of increasing extension step time on the read length and data quality produced by Thermo Sequenase DNA polymerase in fluorescently labeled terminator DNA sequencing reactions FIGS. 23–27 (SEQ ID Nos. 20–24, respectively) show the effect of increasing extension step time on the read length and data quality produced by FY7 DNA polymerase in fluorescently labeled terminator DNA sequencing reactions.
Figure 18B:
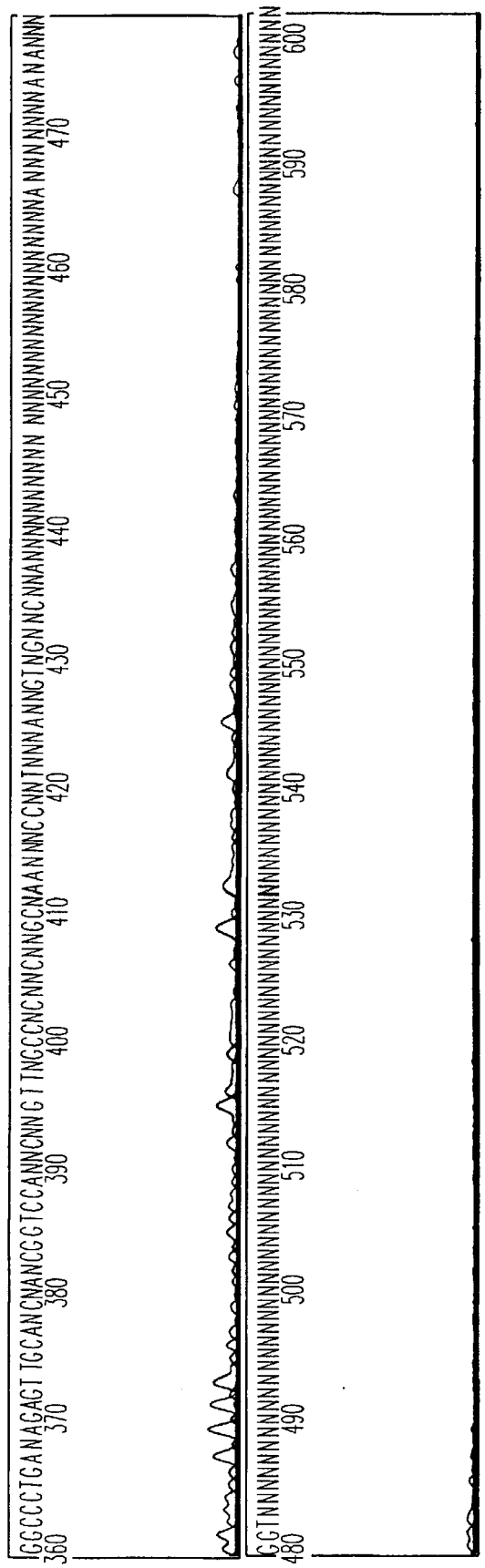
Figure 19A:
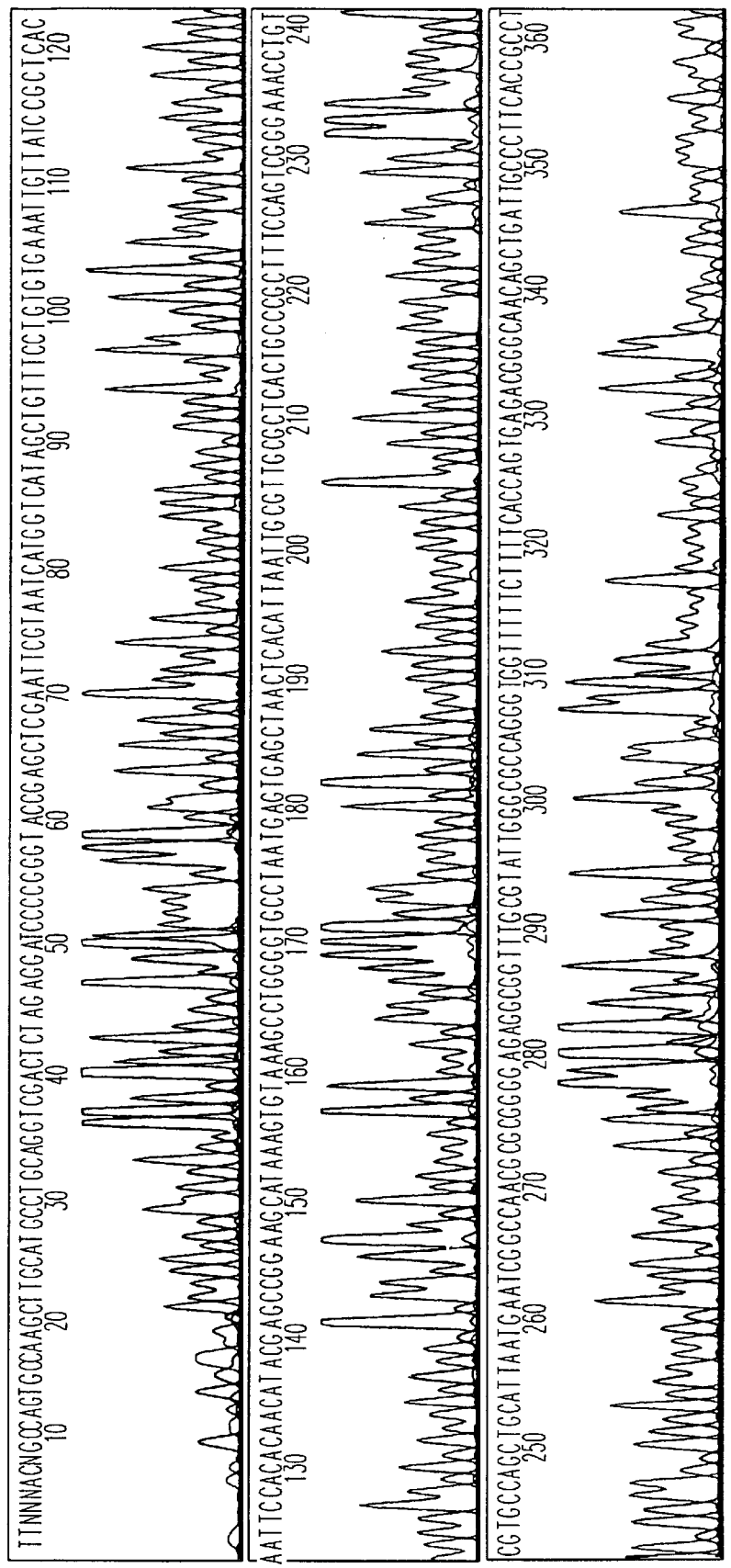
Figure 19B:
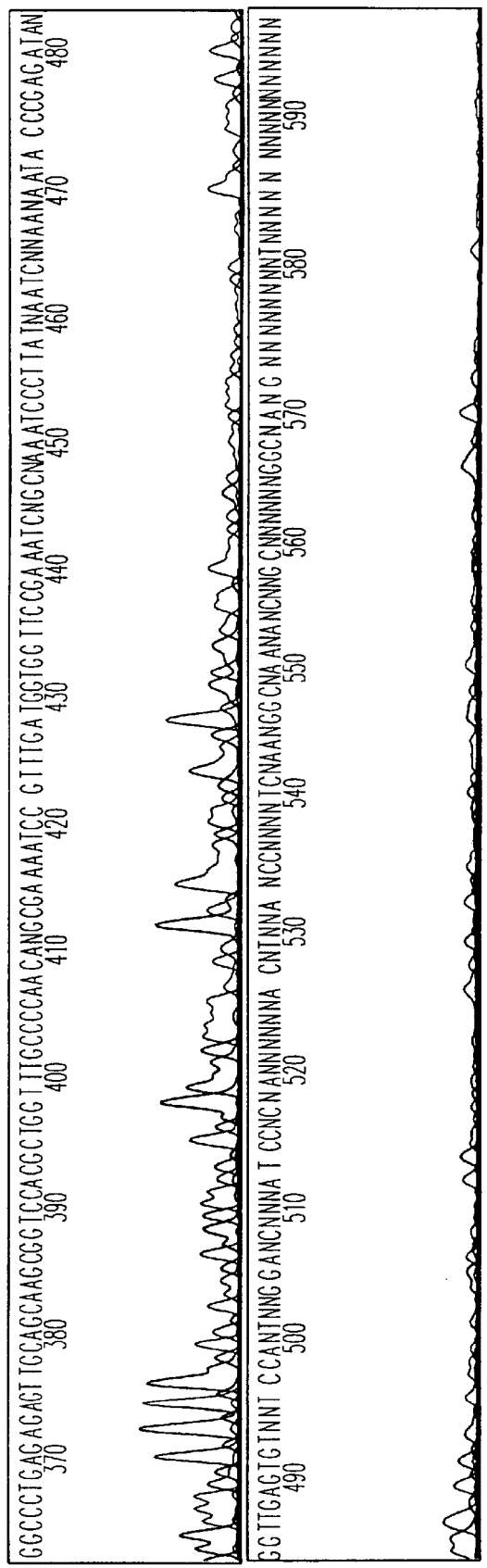
Figure 20A:
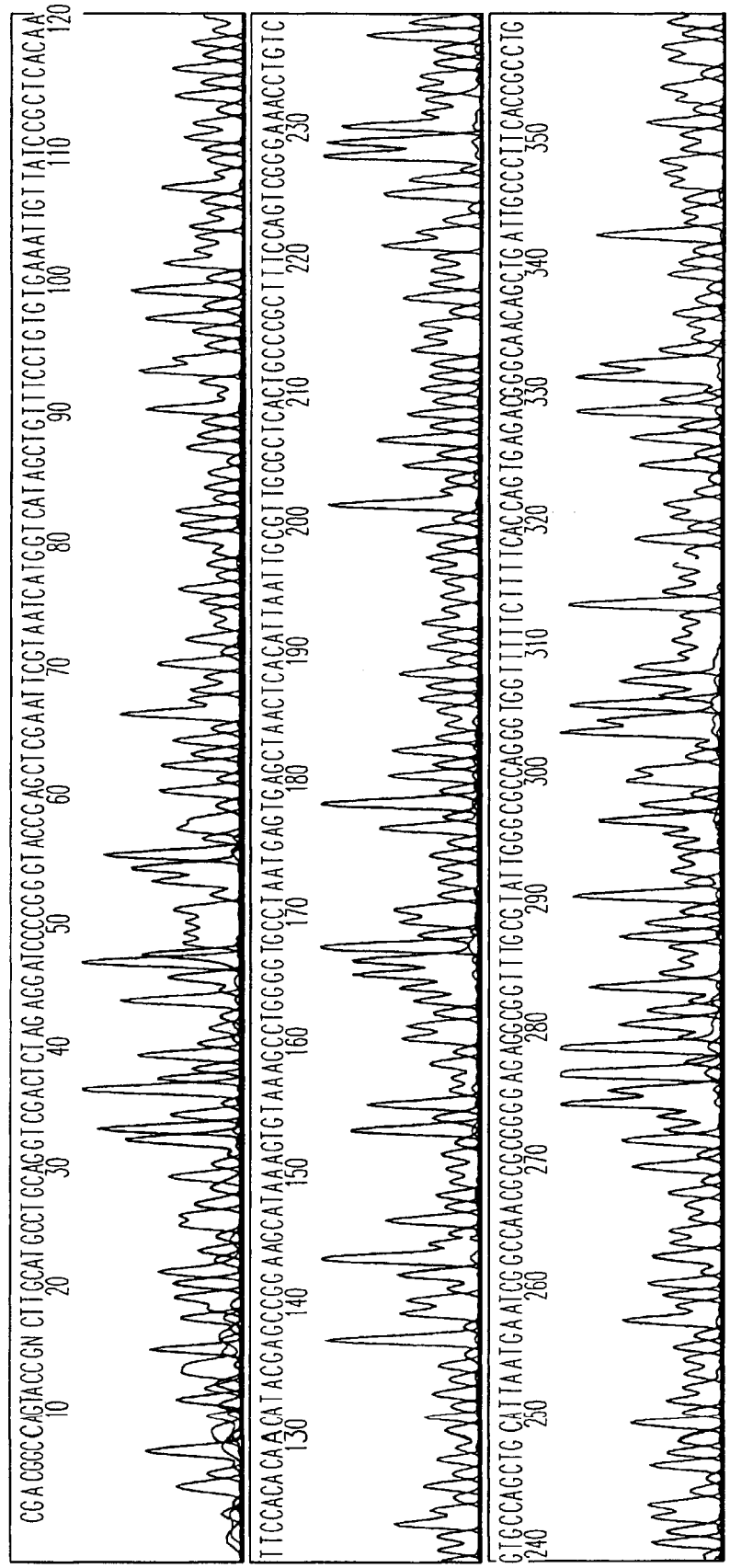
Figure 20B:
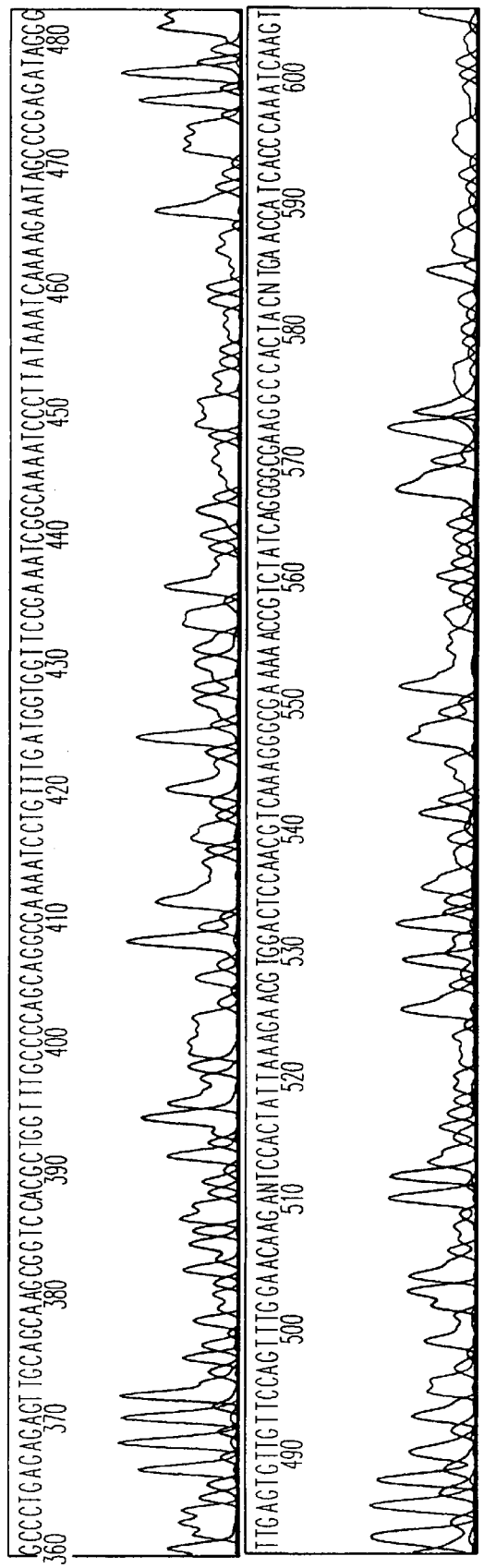
Figure 21A:
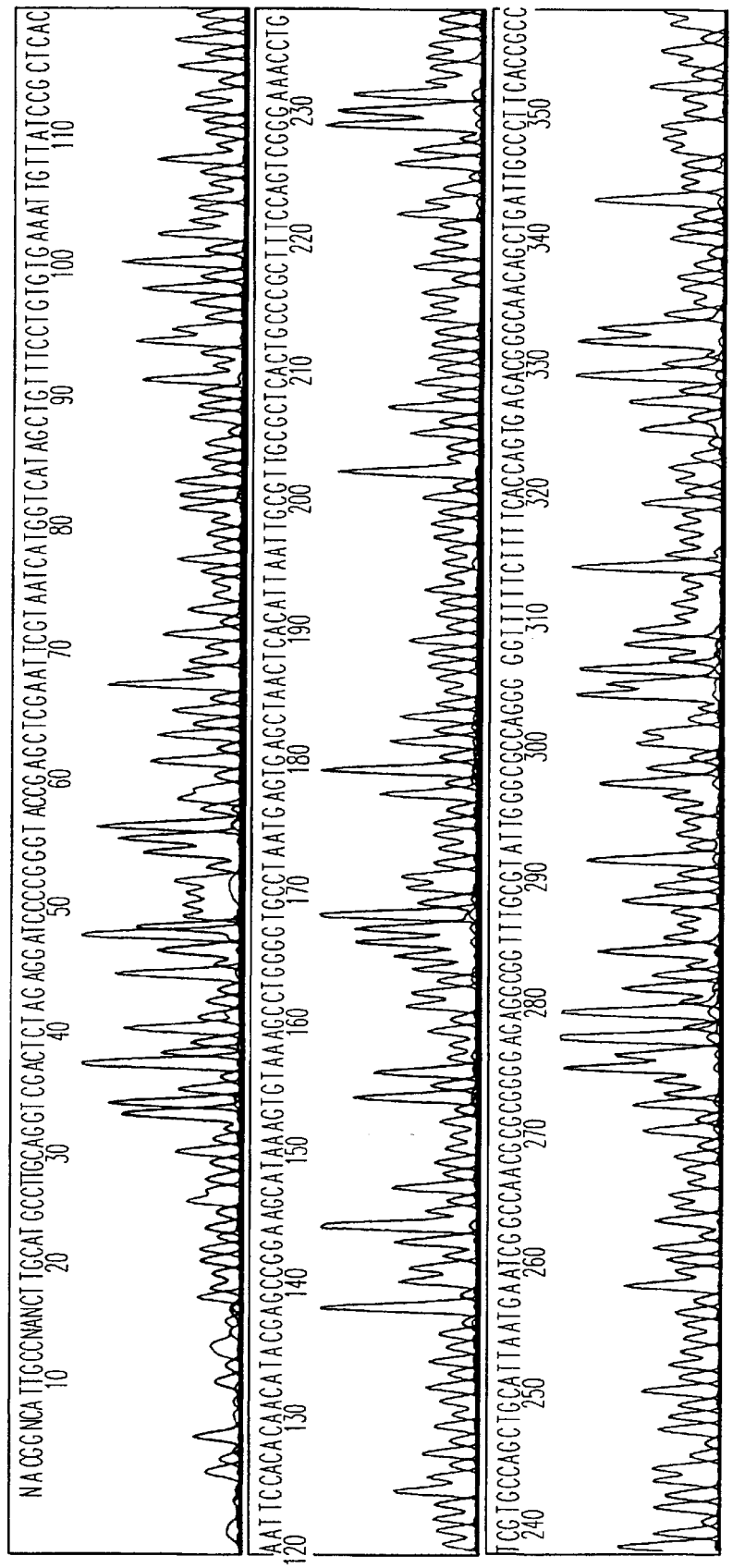
Figure 21B:
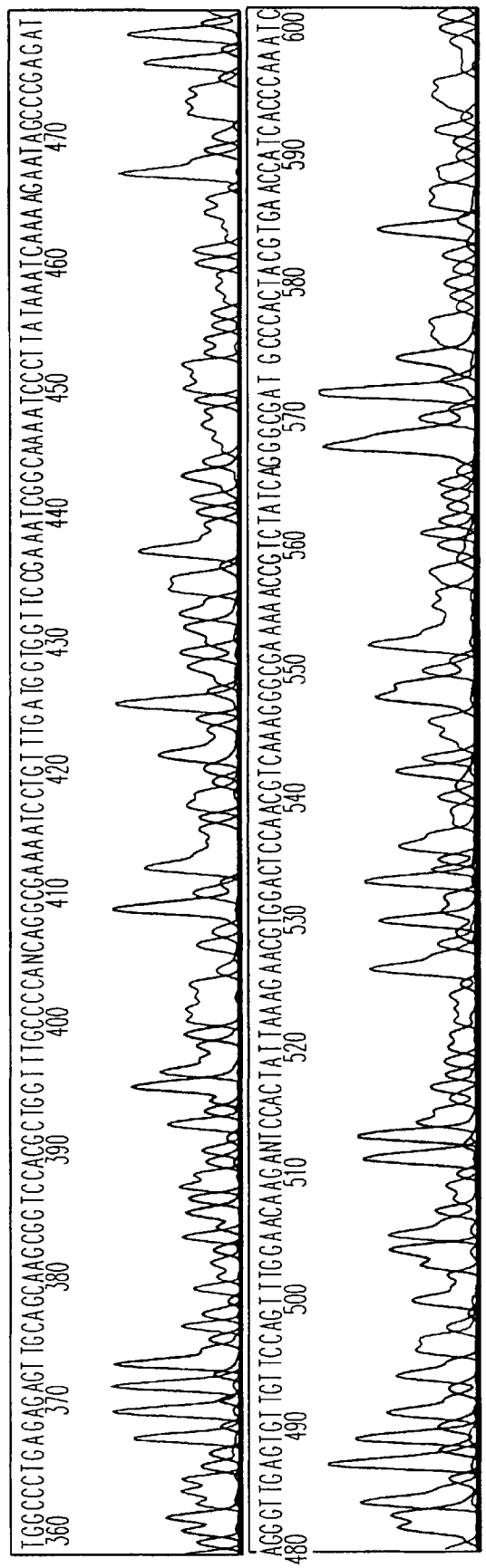
Figure 22A:
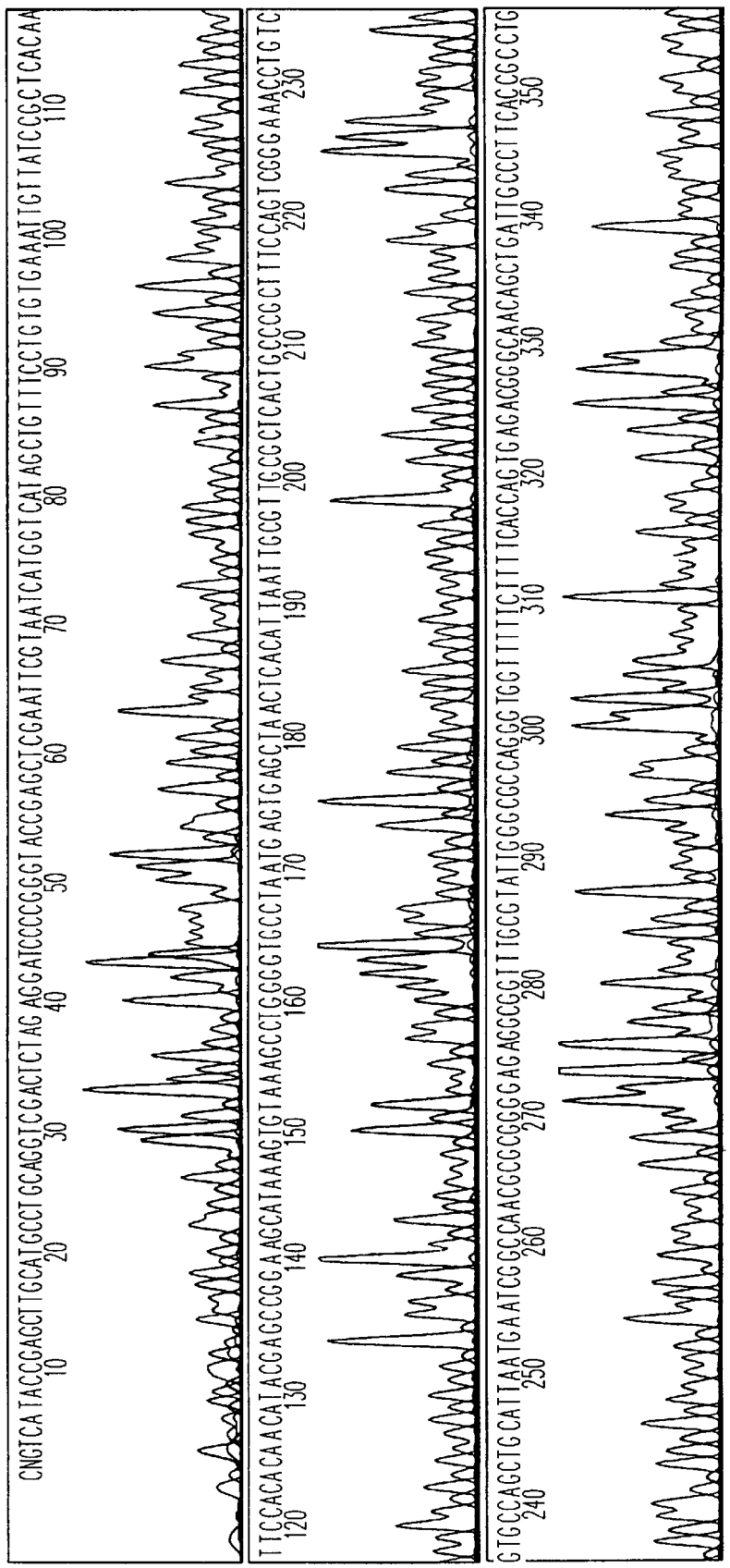
Figure 22B:
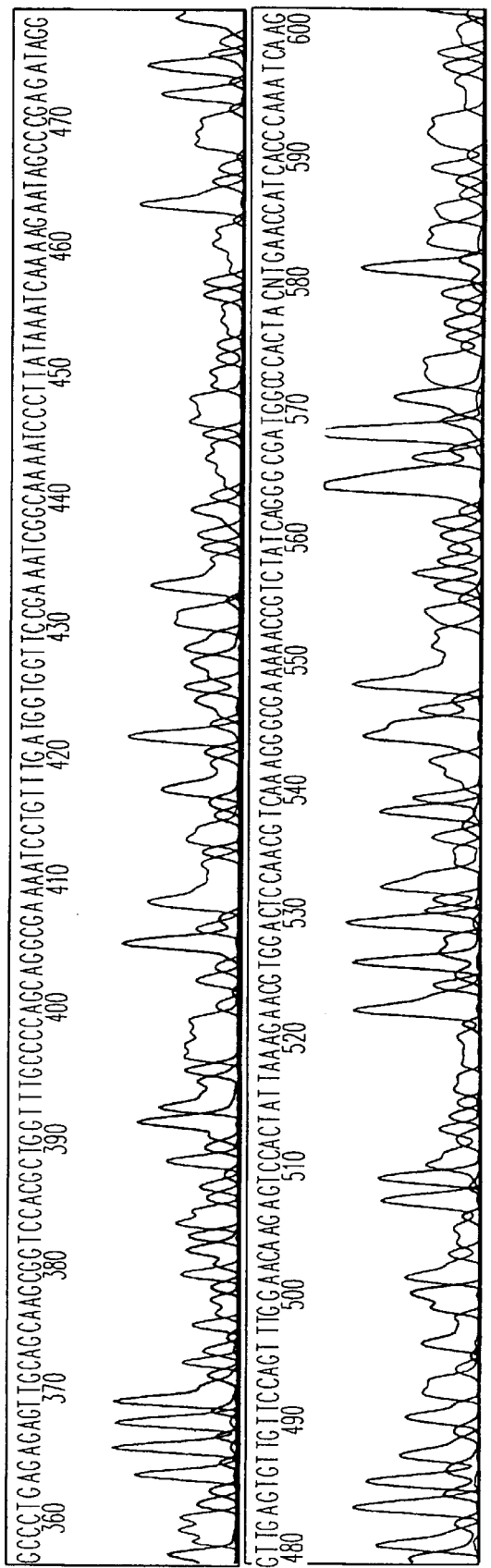
Figure 23A:
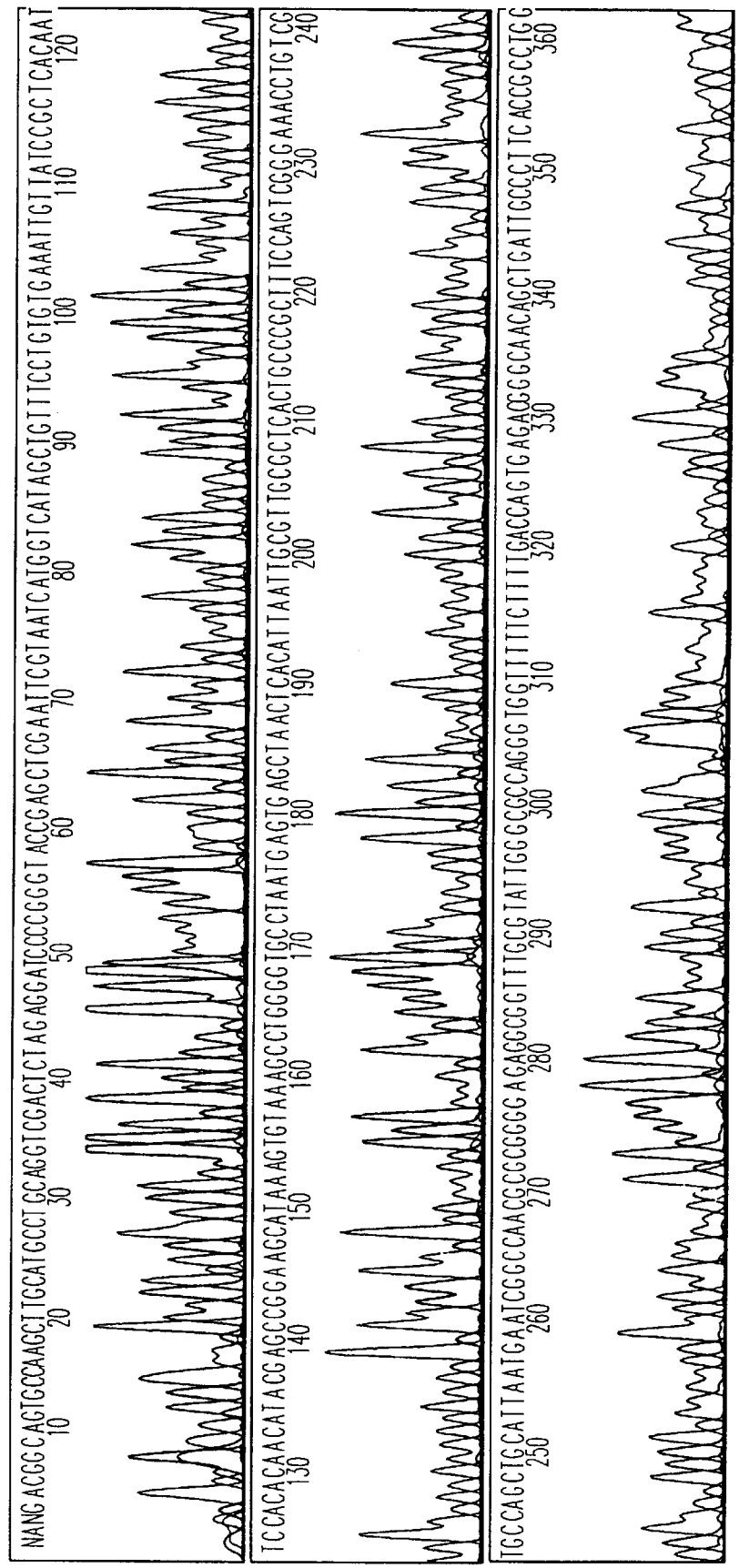
Figure 23B:
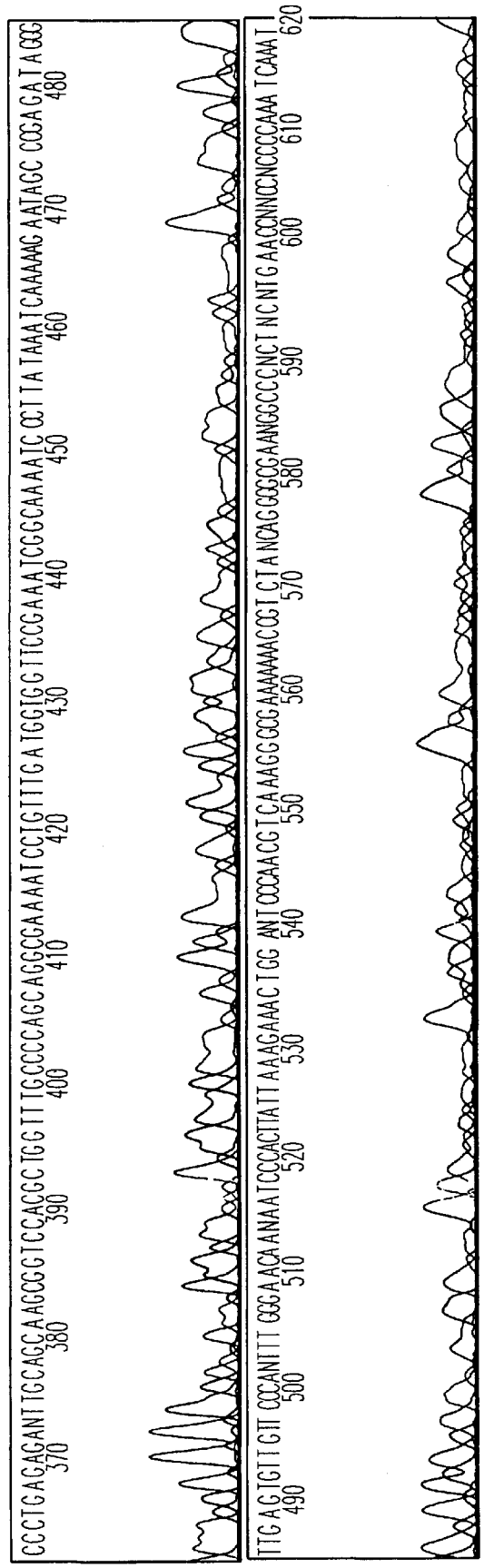
Figure 24A:
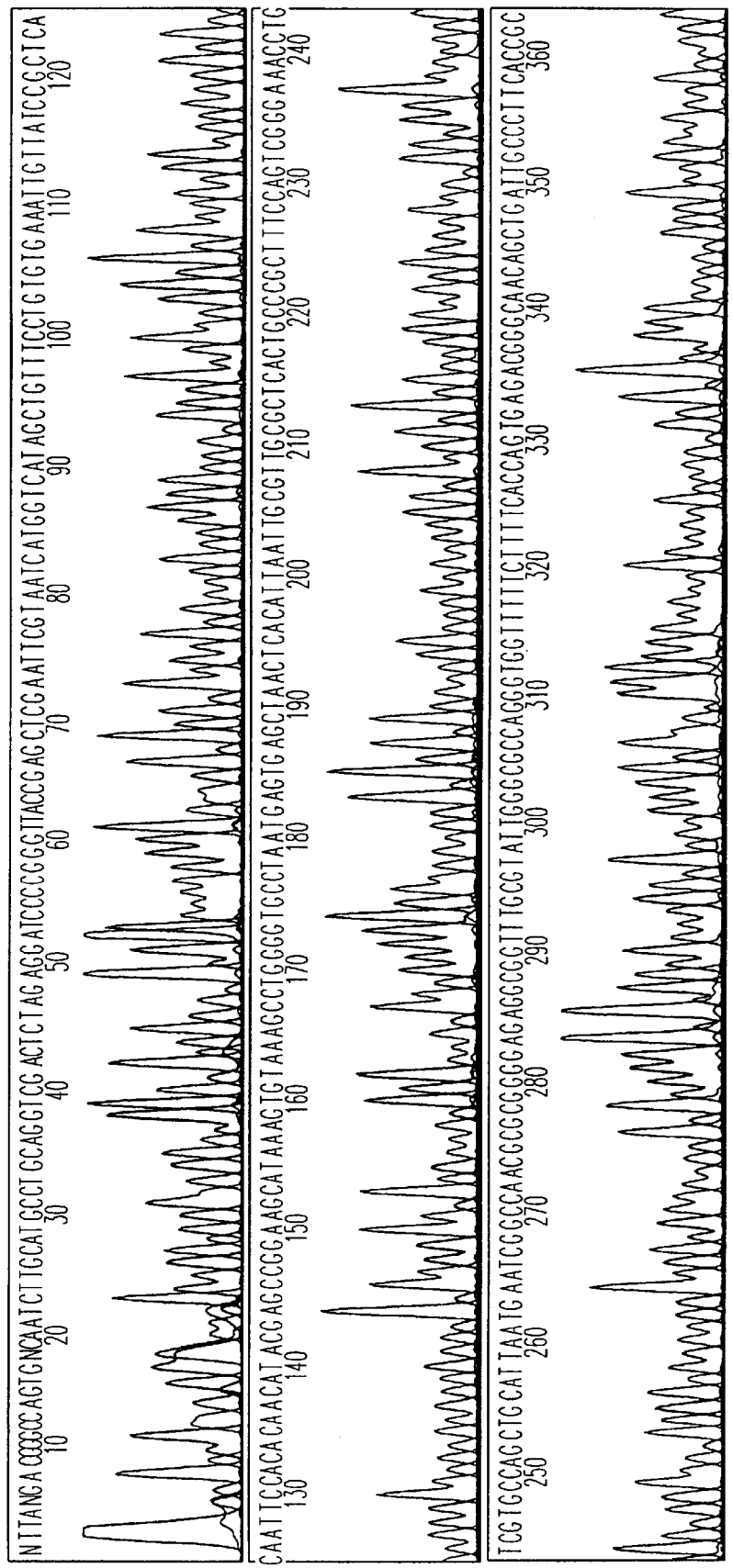
Figure 24B:
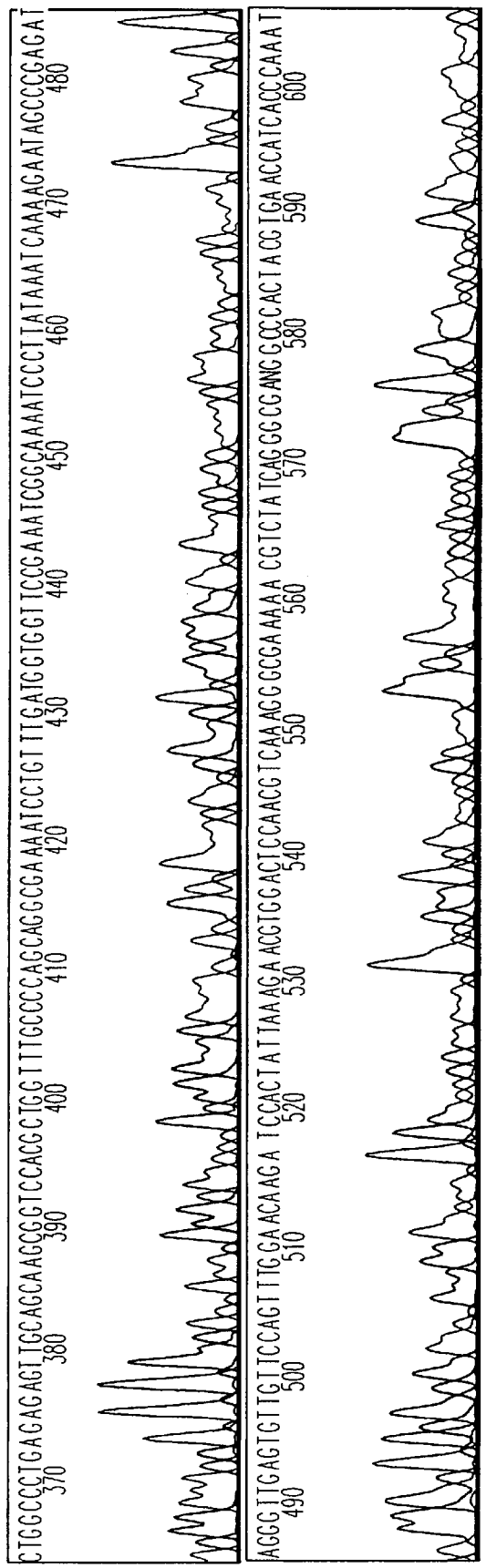
Figure 25A:
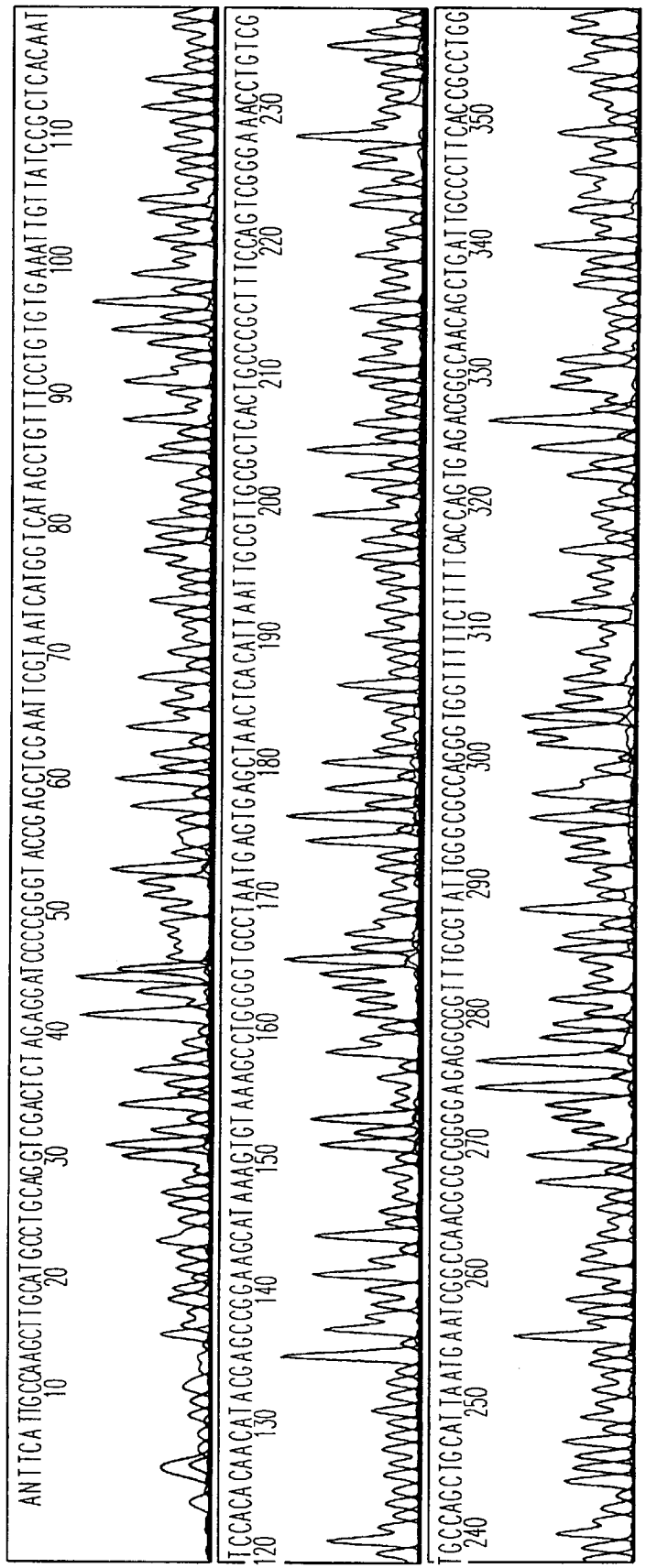
Figure 25B:
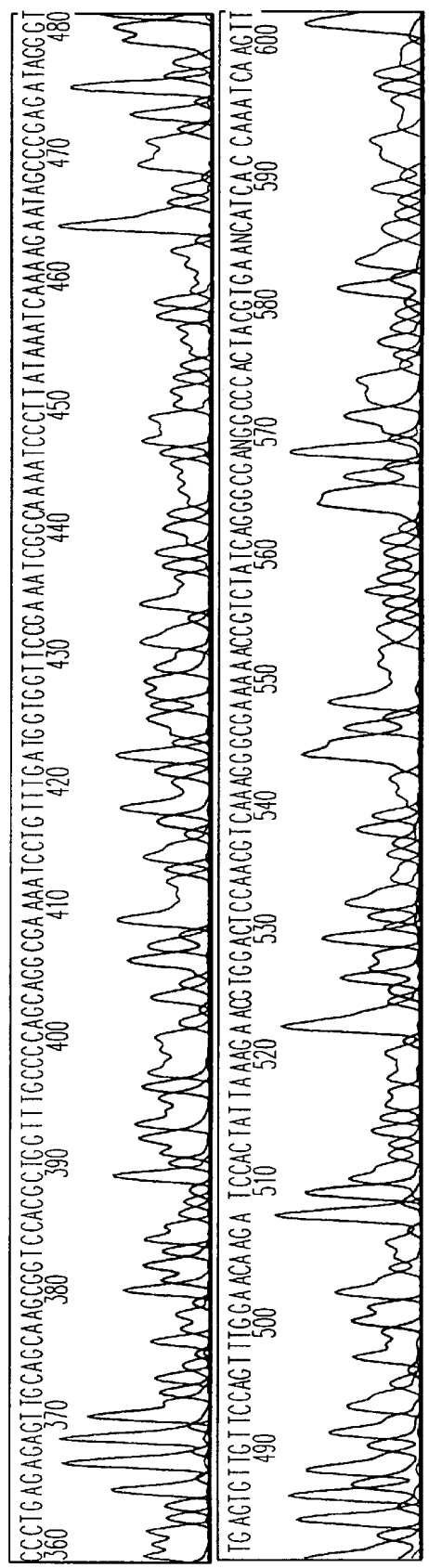
Figure 26A:
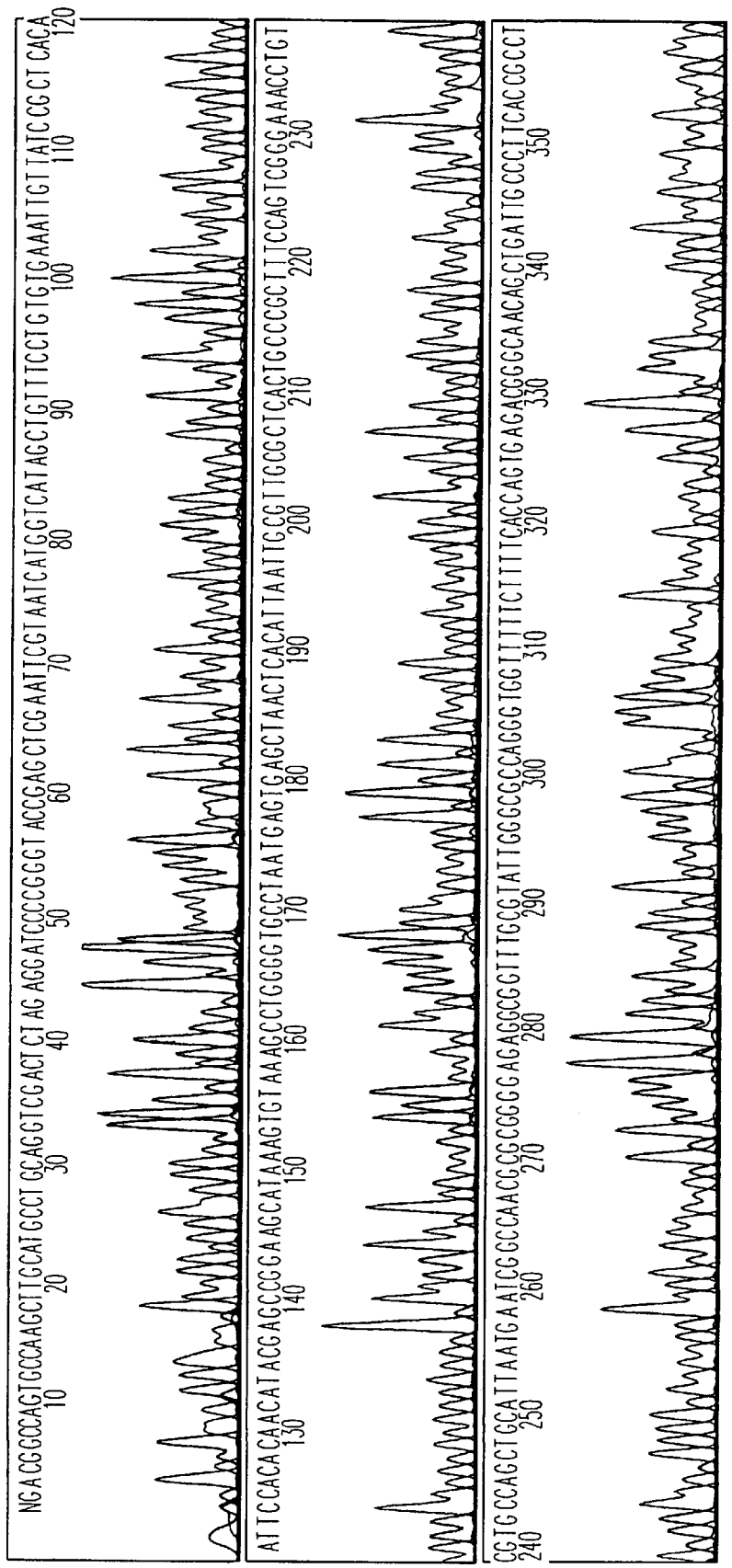
Figure 26B:
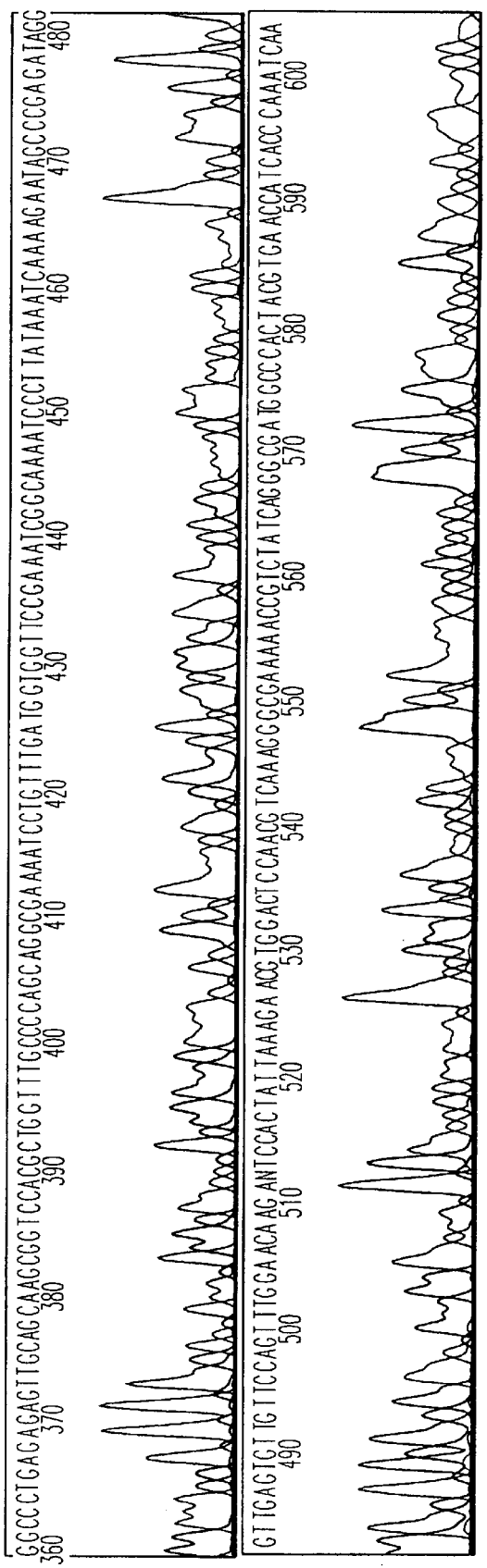
Figure 27A:
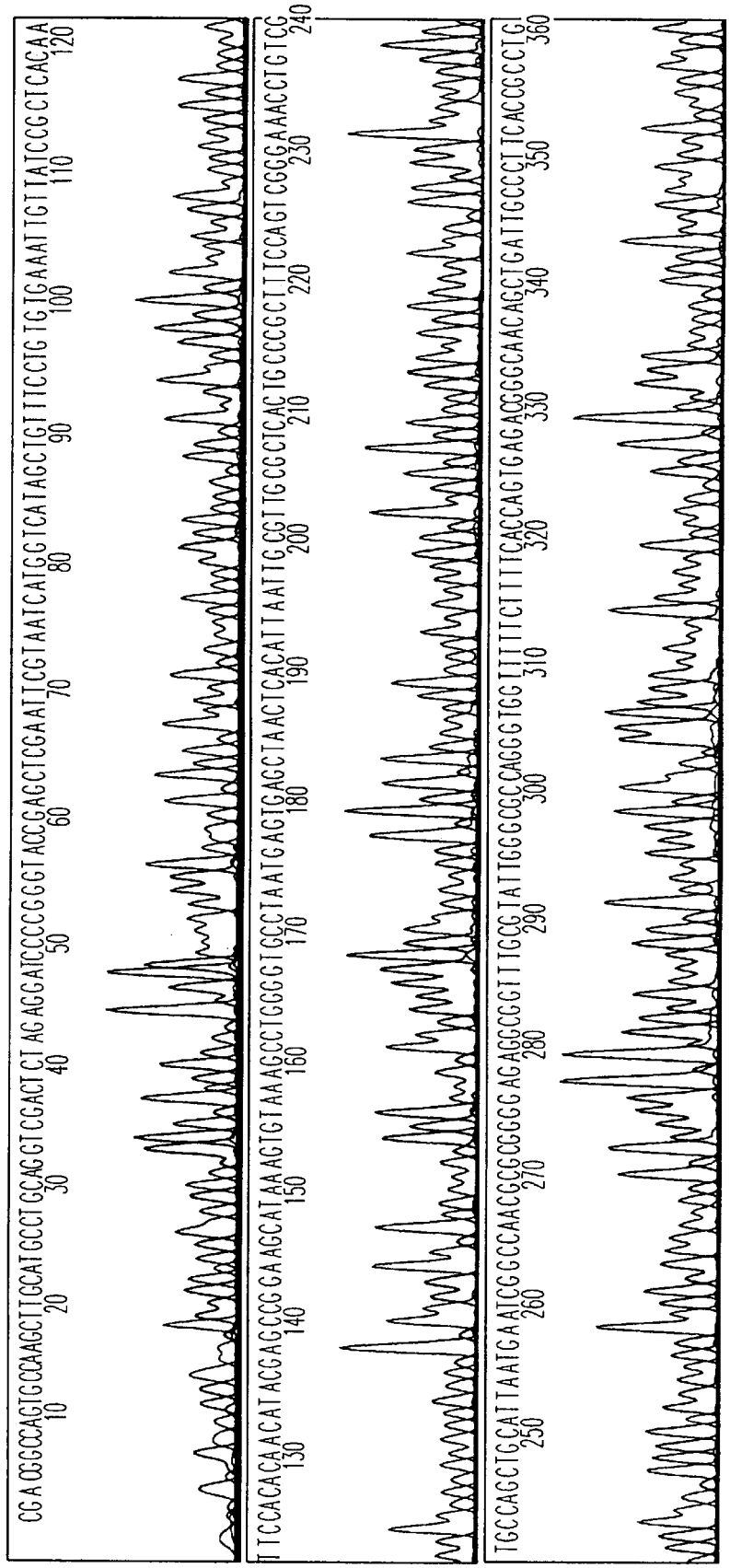
Figure 27B:
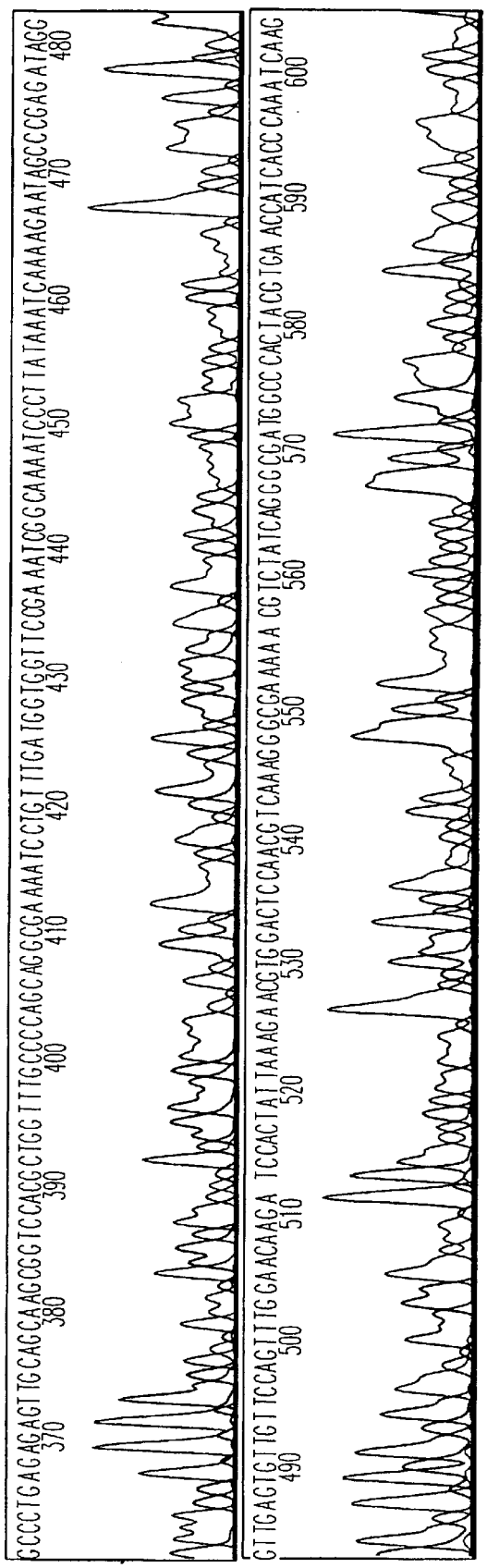

The series examined improved read length obtained when using FY7 polymerase versus Thermo Sequenase DNA polymerase in radioactively labeled sequencing reactions incorporating the dGTP (Guanosine triphosphate) analog dITP (Inosine triphosphate) at 72° C. The results are presented in FIG. 17. FY7 is able to incorporate >50–100 more nucleotides under standard $^{33}$P[α-dATP] sequencing conditions than Thermo Sequenase.

Example 9

Effect of Extension Step Time on Length of Read

These series of experiments examined the effect of increasing extension step time of the read length and data quality of Thermo Sequenase and FY7 DNA polymerases in fluorescently labeled terminator DNA sequencing reactions. The results are presented in FIGS. 18–27.

FIGS. 18–22 show the effect of increasing extension step time on the read length and data quality produced by Thermo Sequenase DNA polymerase. This data shows that a minimum of a two minutes extension step is required by Thermo Sequenase in order to achieve a quality read of at least 600 bases. Signal strength generally increases to a maximum at a four minute extension (the time specified in the commercial product utilizing this enzyme and method).

FIGS. 23–27 show the effect of increasing extension step time on the read length and data quality produced by FY7 DNA polymerase. This data shows that a minimum of a 30 second extension step is required by FY7 in order to achieve a quality read of at least 600 bases. Signal strengths plateau at about one minute extension time. The FY7 DNA polymerase can produce data of equivalent quality to Thermo Sequenase in one-quarter to one-half the time of extension reaction.

Although the above examples describe various embodiments of the invention in detail, many variations will be apparent to those of ordinary skill in the art. Accordingly, the above examples are intended for illustration purposes and should not be used in any way to restrict the scope of the appended claims.

What is claimed is:

1. A purified recombinant thermostable DNA polymerase comprising the amino acid sequence set forth in FIG. 1 (SEQ ID No. 2).

2. A kit for sequencing DNA comprising the DNA polymerase of claim 1.

* * * * *